(12) United States Patent
Armistead et al.

(10) Patent No.: US 7,282,504 B2
(45) Date of Patent: Oct. 16, 2007

(54) KINASE INHIBITORS

(75) Inventors: David M. Armistead, Sudbury, MA (US); Jean E Bemis, Arlington, MA (US); Lucian V DiPietro, Gloucester, MA (US); Stephanie D. Geuns-Meyer, Medford, MA (US); Gregory J. Habgood, Merrimac, MA (US); Joseph L. Kim, Wayland, MA (US); Joseph J. Nunes, Andover, MA (US); Vinod F. Patel, Acton, MA (US); Leticia M. Toledo-Sherman, Venice, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 11/125,614

(22) Filed: May 9, 2005

(65) Prior Publication Data

US 2005/0203114 A1 Sep. 15, 2005

Related U.S. Application Data

(63) Continuation of application No. 10/353,507, filed on Jan. 28, 2003, now abandoned, which is a continuation of application No. 09/785,599, filed on Feb. 16, 2001, now abandoned.

(60) Provisional application No. 60/183,256, filed on Feb. 17, 2000.

(51) Int. Cl.
    *C07D 403/04* (2006.01)
    *A61K 31/404* (2006.01)

(52) U.S. Cl. .................. 514/275; 544/122; 544/323; 544/324

(58) Field of Classification Search ............ 544/323, 544/324, 122; 514/275
    See application file for complete search history.

(56) References Cited

U.S. PATENT DOCUMENTS

| | | | |
|---|---|---|---|
| 4,983,608 A | 1/1991 | Effland et al. | |
| 5,043,317 A | 8/1991 | Chapman et al. | |
| 5,935,966 A | 8/1999 | Suto et al. | |
| 5,958,935 A | 9/1999 | Davis et al. | |
| 6,080,858 A | 6/2000 | Schumacher | |
| 6,107,301 A | 8/2000 | Aldrich et al. | |
| 6,716,831 B1 * | 4/2004 | Breault et al. | 514/183 |
| 2004/0171630 A1 * | 9/2004 | Kim et al. | 514/275 |

FOREIGN PATENT DOCUMENTS

| | | |
|---|---|---|
| EP | 0 002 341 | 6/1979 |
| EP | 0 379 806 B1 | 4/1996 |
| EP | 0 945 443 | 9/1999 |
| EP | 0 945 443 A1 | 9/1999 |
| EP | 1 040 831 A2 | 4/2000 |
| WO | WO94/26733 | 11/1994 |
| WO | WO95/33750 | 12/1995 |
| WO | WO96/05177 | 2/1996 |
| WO | WO97/19065 | 5/1997 |
| WO | WO98/18782 | 5/1998 |
| WO | WO99/31073 | 6/1999 |
| WO | WO99/41253 | 8/1999 |
| WO | WO99/50250 | 10/1999 |
| WO | WO 00/12485 | 3/2000 |
| WO | WO 00/27825 | 5/2000 |
| WO | WO 00/39101 | 7/2000 |
| WO | WO 00/43373 | 7/2000 |
| WO | WO 00/53595 | 9/2000 |
| WO | WO 00/59892 | 10/2000 |
| WO | WO 00/63204 | 10/2000 |
| WO | WO 00/78731 | 12/2000 |
| WO | WO 01/00213 | 1/2001 |
| WO | WO 01/22938 | 4/2001 |
| WO | WO 01/29009 | 4/2001 |
| WO | WO 01/40218 | 6/2001 |

OTHER PUBLICATIONS

Amemiya et al., "Synthesis and α-adrenergic activities of 2- and 4-substituted imidazoline and imidazole analogues", Journal of Medicinal Chemistry, 35:750-755 (1992).

Amemiya et al., "Dehydrogenation of imidazolines to imidazoles with palladium-carbon", Synthetic Communications, 20(16): 2483-2490 (1990).

Arutyunyan et al., "Reaction of uracils with Phosphoric acid amides", Abstract IZV. AKAD. NAUK SSR, SER. KHIM (4):904-909 (1970).

Bairoch, *The Enzyme Database*, Nucleic Acids Research, 28 (1): 304-305 (2000).

Braunwalder, et al., *A solid-phase assay for the determination of protein tyrosine kinase activity of c-src using scintillating microtitration plates*, Analytical Biochemistry 234 (1): 23-26 (1996).

Brunet et al., *Akt promotes cell survival by phosphorylating and inhibiting a forkhead transcription factor*, Cell 96: 857-868 (1999).

Buchdunger et al., *Inhibition of the Abl protein -tyrosine kinase* in vitro and in vivo *by a 2-Phenylaminopyrimidine Derivative*, Cancer Research, 56, 100-104 (1996).

Cleaveland et al., *A microtiter-based assay for the detection of protein tyrosine kinase activity*, Anal Biochem 190 (2): 249-253 (1990).

Czarnik, *Encoding methods for combinatorial chemistry*, Current Opinions Chemical Bio., 1: 60-66 (1997).

(Continued)

*Primary Examiner*—Deepak Rao
(74) *Attorney, Agent, or Firm*—Joseph W. Bulock

(57) ABSTRACT

The invention relates to inhibitors of kinases, compositions comprising the inhibitors, and methods of using the inhibitors and inhibitor compositions. The inhibitors and compositions comprising them are useful for treating disease or disease symptoms. The invention also provides for methods of making kinase inhibitor compounds, methods of inhibiting kinase activity, and methods for treating disease or disease symptoms.

11 Claims, No Drawings

OTHER PUBLICATIONS

El-Kerdawy et al., "Synthesis of certain esters of pteroyl glutamic acid analogues structurally related to antimetabolite anticancer compounds", Journal of Pharmaceutical Sciences or the United Arab Republic, 9:1-6 (1968).
Fieser et al., *Fieser & Fieser's Reagents for Organic Synthesis*, John Wiley & Sons (1994).
Garcia-Bustos et al., *PIK1, an essential phosphatidylinositol 4-Kinase associated with the yeast nucleus*, The EMBO Journal, 13 (10): 2352-2361 (1994).
Gish et al., *Bacterial expression, purification and preliminary kinetic description of the kinase domain of v-fps*, Protein Engineering, 8 (6): 609-614 (1995).
Ghosh et al., "2,4-Bis (p-chloroanillino) pyrimidine, an uncoupler of oxidative phosphorylation", Abstract, FEBS Lett., 4(3):157-159 (1969).
Ghosh et al., "2,4-Bis (arylamino)-6-methylpyrimidines as antimicrobial agents", Abstract, J. Indian Chem. Soc., 48(5):512-513 (1981).
Greene, *Protective Groups in Organic Synthesis*, 2nd Ed., John Wiley & Sons (1991).
Grigor'eva et al., Catalytic activity of complexes of copper (II) with carboxyphenylaminopyrimidines antiinflammatory drugs in model reactions of oxidase and catalase type, Chemical Abstracts, 89:36533 (1978).
Hanks et al., *The eukaryotic protein kinase superfamily: kinase (catalytic) domain structure and classification* FASEB Journal, 9: 576-596 (1995).
Hardie, *The Protein Kinase Facts Book, I & II*, Academic Press, San Diego, CA (1995).
Hiles et al., *Phosphatidylinositol 3-Kinase: Structure and Expression of the 110 kd Catalytic Subunit*, Cell, 70: 419-429 (1992).
Hoffmann et al., *The PROSITE database, its status in 1999*, Nucleic Acids, Res. 27 (1): 215-219 (1999).
Kaga, Shuji, et al., *Activation of p21-CDC42/RAC-activated kinases by CD28 signaling: p21-activated kinase (PAK) and MEK kinase 1 (MEKK1) may mediate the interplay between CD3 and CD28 signals*, Journal of Immunology 160: 4182-4189 (1998).
Karp et al., "Synthesis and antiinflammatory properties of o-carboxyphenylaminopyrimidines", Abstract, KHIM.—Farm. Zh. 17(11):1304-1307 (1983).
Kirk, *Facile Synthesis of 2 Substituted Imidazoles*, J. Org. Chem 43 (22), 4381-4383 (1978).
Knighton et al., *Crystal Structure of the Catalytic Subunit of Cyclic Adenosine Monophosphate-Dependent Protein Kinase* Science, 253: 407-414 (1991).
Koguro et al., "Novel synthesis of 5-substituted tetrazoles from nitriles", Synthesis, 910-914 (1997).
Kolb et al., *Tyrosine kinase assays adapted to homogeneous time-resolved fluorescence*, Drug Discovery Today, 3 (7):333-342, (1998).
Kume et al., "Orally active cephalosporins. II. Synthesis and structure-activity relationships of new 7 beta-[(Z)-2-(2-aminothiazol-4-yl)-2-hydroxyiminoacetamido]-caphalosporins with 1,2,3-triazole in C-3 side chain", Journal of Antibiotics, 46(1):177-192 (1993).
Kunz et al, *Target of Rapamycin in yeast, TOR2 is an essential phosphatidylinositol kinase homolog required for G, progression*, Cell, 73: 585-596 (1993).
Larock, *Comprehensive Organic Transformations*, VCH Publishers (1989).
Lehr et al., *Production, purification and characterization of non-myristylated human T-cell protein tyrosine kinase in a baculovirus expression system*, Gene 169; 275-279 (1996).
Liu et al., *Janus kinases in interleukin-2-mediated signaling: JAK1 and JAK3 are differentially regulated by tyrosine phosphorylation*, Current Biology, 7 (11): 817-826 (1997).
Nagata et al., "Tricyclic quinoxalinediones: 5,6-dihydro-1H-pyrrolo[1,2,3-de]quinoxaline-2,3-diones and 6,7-dihydro-1H,5H-pyrido[1,2,3-de]quinoxaline-2,3-diones as potent antagonists for the glycine binding site of the NMDA receptor", Journal of Medicinal Chemistry, 37:3956-3968 (1994).
Obrecht et al., *Solid-Supported Combinatorial and Parallel Synthesis of Small-Molecula- Weight Compound Libraries*, Pergamon-Elsevier Science Limited (1998).
Olayioye et al., *ErB-1 and ErbB-2 acquire distinct signaling properties dependent upon their dimerization partner*, Molecular & Cellular Biology, 18 (9): 5042-5051 (1998).
Paquette, *Encyclopedia Of Reagents For Organic Synthesis*, John Wiley & Sons (1995).
Pozdnev, "Activation of carboxylic acids by pyrocarbonates. Application of di-tert-butyl pyrocarbonate as condensing reagent in the synthesis of amides of protected amino acids and peptides", Tetrahedron Letters, 36(39):7115-7118 (1995).
Satterthwaite, *Independent and opposing roles for Btk and Lyn in B cell and myeloid signaling pathways*, J. of Exp. Med. 188 (5): 833-844 (1998).
Seethala et al., *A fluorescence polarization competition immunoassay for tyrosine kinases*, Anal. Biochem., 255 (2): 257-262 (1998).
Stephan et al., *FcεR1-induced protein tyrosine phosphorylation of pp72 in rat basophilic leukemia cells (RBL-2H3)*, Journal of Biological Chemistry, 267 (8): 5434-5441, (1992).
Tepe et al., "Inhibition of DNA topoisomerase II by azaelliptitoxins functionalized in the variable substituent domain", Journal of Medicinal Chemistry, 39:2188-2196 (1996).
Wu et al., *Measurement of Cdk4 kinase activity using an affinity peptide-tagging technology*, Comb. Chem. High Throughput Screen. 3: 27-36 (2000).
Yoshida et al., *Differential endothelial migration and proliferation to basic fibroblast growth factor and vascular endothelial growth factor*, Growth Factors 13: 57-64 (1996).

\* cited by examiner

KINASE INHIBITORS

This application is a continuation of U.S. application Ser. No. 10/353,507 filed on Jan. 28, 2003, which is a continuation of U.S. application Ser. No. 09/785,599 filed on Feb. 16, 2001, which claims priority benefit under Title 35 USC §119(e) of U.S. Provisional Application No. 60/183,256 filed Feb. 17, 2000 and entitled Kinase Inhibitors, the entire contents of which are incorporated herein by reference.

BACKGROUND OF THE INVENTION

The invention relates to inhibitors of enzymes that catalyze phosphoryl transfer and/or that bind ATP/GTP nucleotides, compositions comprising the inhibitors, and methods of using the inhibitors and inhibitor compositions. The inhibitors and compositions comprising them are useful for treating or modulating disease in which phosphoryl transferases, including kinases, may be involved, symptoms of such disease, or the effect of other physiological events mediated by phosphoryl transferases, including kinases. The invention also provides for methods of making the inhibitor compounds and methods for treating diseases in which one or more phosphoryl transferase, including kinase, activities is involved.

Phosphoryl transferases are a large family of enzymes that transfer phosphorous-containing groups from one substrate to another. By the conventions set forth by the Nomenclature Committee of the International Union of Biochemistry and Molecular Biology (IUBMB) enzymes of this type have Enzyme Commission (EC) numbers starting with 2.7.—.— (See, Bairoch A., The ENZYME database in Nucleic Acids Re.s 28:304-305(2000)). Kinases are a class of enzymes that function in the catalysis of phosphoryl transfer. The protein kinases constitute the largest subfamily of structurally related phosphoryl transferases and are responsible for the control of a wide variety of signal transduction processes within the cell. (See, Hardie, G. and Hanks, S. (1995) The Protein Kinase Facts Book, I and II, Academic Press, San Diego, Calif.). Protein kinases are thought to have evolved from a common ancestral gene due to the conservation of their structure and catalytic function. Almost all kinases contain a similar 250-300 amino acid catalytic domain. The protein kinases may be categorized into families by the substrates they phosphorylate (e.g., protein-tyrosine, protein-serine/threonine, histidine, etc.). Protein kinase sequence motifs have been identified that generally correspond to each of these kinase families (See, for example, Hanks, S. K., Hunter, T., FASEB J., 9:576-596 (1995); Knighton et al., Science, 253:407-414 (1991); Hiles et al., Cell, 70:419-429 (1992); Kunz et al., Cell, 73:585-596 (1993); Garcia-Bustos et al., EMBO J., 13:2352-2361 (1994)). Lipid kinases (e.g. PI3K) constitute a separate group of kinases with structural similarity to protein kinases.

Since the X-ray structure of the catalytic subunit of cAMP-dependent protein kinase (cAPK) was elucidated, approximately two dozen additional protein kinase structures and one lipid kinase structure have been solved as either apo enzymes or binary and ternary complexes (with ATP, ATP analogs, metal ions, ADP, ATP competitive inhibitors in the absence or presence of peptide substrate or peptide inhibitors). These proteins share structurally conserved catalytic domains (kinase domains) comprising two lobes that can be further subdivided into twelve subdomains. The N-terminal portion forms the small lobe (including subdomains I-IV) whose architecture is composed of an antiparallel five-strand β-sheet and one α-helix, while the lower C-terminal domain forms another lobe (including subdomains VIA-XI) containing mostly α-helical architecture. Subdomain V spans the two lobes. The N-terminal domain is thought to participate in orienting the nucleotide (or other binding entity), while the C-terminal domain is thought to be responsible for binding peptide substrate and initiating phosphotransfer to the hydroxyl group of a serine, threonine, or tyrosine residue.

The N- and C-terminal domains are connected through a single peptide strand, to which the adenine moiety of ATP and/or GTP binds via an eleven membered hydrogen bond cycle, involving the N1 and the N6 amino group, and the backbone carbonyl and NH functions of two nonconsecutive residues. This linker acts as a hinge about which the domains can rotate with respect to each other without disruption of the secondary architecture of the kinase. Several torsion angle changes in the linker backbone allow this movement to occur. The ribose group of ATP is anchored to the enzyme via hydrogen bonds with residues within the ribose-binding pocket. The triphosphate group is held in position via various polar interactions with several variable residues from the glycine rich loop, the conserved DFG motif and the catalytic loop.

The "kinase domain" appears in a number of polypeptides which serve a variety of functions. Such polypeptides include, for example, transmembrane receptors, intracellular receptor associated polypeptides, cytoplasmic located polypeptides, nuclear located polypeptides and subcellular located polypeptides. The activity of protein kinases can be regulated by a variety of mechanisms. It must be noted, however, that an individual protein kinase may be regulated by more than one mechanism. These mechanisms include, for example, autophosphorylation, transphosphorylation by other kinases, protein-protein interactions, protein-lipid interactions, protein-polynucleotide interactions, ligand binding, and post-translational modification.

Protein and lipid kinases regulate many different cell processes including, but not limited to, proliferation, growth, differentiation, metabolism, cell cycle events, apoptosis, motility, transcription, translation and other signaling processes, by adding phosphate groups to targets such as proteins or lipids. Phosphorylation events catalyzed by kinases act as molecular on/off switches that can modulate or regulate the biological function of the target protein. Phosphorylation of target proteins occurs in response to a variety of extracellular signals (hormones, neurotransmitters, growth and differentiation factors, etc.), cell cycle events, environmental or nutritional stresses, etc. Protein and lipid kinases can function in signaling pathways to activate or inactivate, or modulate the activity of (either directly or indirectly) the targets. These targets may include, for example, metabolic enzymes, regulatory proteins, receptors, cytoskeletal proteins, ion channels or pumps, or transcription factors. Uncontrolled signaling due to defective control of protein phosphorylation has been implicated in a number of diseases and disease conditions, including, for example, inflammation, cancer, allergy/asthma, disease and conditions of the immune system, disease and conditions of the central nervous system (CNS), cardiovascular disease, dermatology, and angiogenesis.

Initial interest in protein kinases as pharmacological targets was stimulated by the findings that many viral oncogenes encode structurally modified cellular protein kinases with constitutive enzyme activity. These findings pointed to the potential involvement of oncogene related protein kinases in human proliferative disorders. Subsequently, deregulated protein kinase activity, resulting from a variety of more subtle mechanisms, has been implicated in the pathophysiology of a number of important human disorders including, for example, cancer, CNS conditions, and immunologically related diseases. The development of selective protein kinase inhibitors that can block the disease pathologies and/or symptoms resulting from aberrant protein kinase activity has therefore generated much interest.

SUMMARY OF THE INVENTION

The invention relates to compounds of the formula:

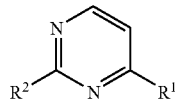

wherein,

Each $R^1$ and $R^2$ is independently $R^3$; $R^8$; $NHR^3$; $NHR^5$; $NHR^6$; $NR^5R^5$; $NR^5R^6$; $SR^5$; $SR^6$; $OR^5$; $OR^6$; $C(O)R^3$; heterocyclyl optionally substituted with 1-4 independent $R^4$ on each ring; or C1-C10 alkyl substituted with 1-4 independent $R^4$;

Each $R^3$ is independently aryl; phenyl optionally substituted with 1-4 independent $R^4$; or heteroaryl optionally substituted with 1-4 independent $R^4$ on each ring; and the remaining variables are as defined herein.

The invention also relates to compositions comprising these compounds, methods of making these compounds, methods of inhibiting enzyme activity, particularly kinase activity, through use of these compounds, and methods of treating disease or disease symptoms in a mammal, particularly where modulation of enzyme activity, and more particularly kinase activity, can affect disease outcome.

DETAILED DESCRIPTION OF THE INVENTION

The invention provides compounds useful in inhibiting kinase activity and inhibiting kinases or other polypeptides having sequences or subsequences homologous to kinase sequences or subsequences. In one embodiment, the inhibitory compound has the formula:

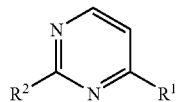

wherein,

Each $R^1$ and $R^2$ is independently $R^3$; $R^8$; $NHR^3$; $NHR^5$; $NHR^6$; $NR^5R^5$; $NR^5R^6$; $SR^5$; $SR^6$; $OR^5$; $OR^6$; $C(O)R^3$; heterocyclyl optionally substituted with 1-4 independent $R^4$ on each ring; or C1-C10 alkyl substituted with 1-4 independent $R^4$;

Each $R^3$ is independently aryl; phenyl optionally substituted with 1-4 independent $R^4$; or heteroaryl optionally substituted with 1-4 independent $R^4$ on each ring;

Each m is independently 0, 1, 2 or 3;

Each n is independently 1 or 2;

Each X is O or S;

Each $R^4$ is independently selected from H, C1-C10 alkyl; C2-C10 alkenyl; C2-C10 alkynyl; C3-C10 cycloalkyl; C4-C10 cycloalkenyl; aryl; $R^8$; halo; haloalkyl; $CF_3$; $SR^5$; $OR^5$; $OC(O)R^5$; $NR^5R^5$; $NR^5R^6$; $COOR^5$; $NO_2$; CN; $C(O)R^5$; $C(O)C(O)R^5$; $C(O)NR^5R^5$; $S(O)_nR^5$; $S(O)_nNR^5R^5$; $NR^5C(O)NR^5R^5$; $NR^5C(O)R^5$; $NR^5C(O)R^5$; $NR^5(COOR^5)$; $NR^5C(O)R^8$; $NR^5S(O)_n NR^5R^5$; $NR^5S(O)_nR^5$; $NR^5S(O)_nR^8$; $NR^5C(O)C(O)NR^5R^5$; $NR^5C(O)C(O)NR^5R^6$; C1-C10 alkyl substituted with 1-3 independent aryl, $R^7$ or $R^8$; or C2-C10 alkenyl substituted with 1-3 independent aryl, $R^7$ or $R^8$;

Each $R^5$ is independently H; C1-C10 alkyl; C2-C10 alkenyl; C2-C10 alkynyl; C3-C10 cycloalkyl; C4-C10 cycloalkenyl; aryl; $R^9$; haloalkyl; C1-C10 alkyl substituted with 1-3 independent aryl, $R^7$ or $R^9$ groups; C3-C10 cycloalkyl substituted with 1-3 independent aryl, $R^7$ or $R^9$ groups; or C2-C10 alkenyl substituted with 1-3 independent aryl, $R^7$ or $R^9$;

Each $R^6$ is independently $C(O)R^5$, $COOR^5$, $C(O)NR^5R^5$, or $S(O)_nR^5$;

Each $R^7$ is independently halo, $CF_3$, $SR^{10}$, $OR^{10}$, $OC(O)R^{10}$, $NR^{10}R^{10}$, $NR^{10}R^{11}$, $NR^{11}R^{11}$, $COOR^{10}$, $NO_2$, CN, $C(O)R^{10}$, $OC(O)NR^{10}R^{10}$, $C(O)NR^{10}R^{10}$, $N(R^{10})C(O)R^{10}$, $N(R^{10})(COOR^{10})$, $S(O)_nNR^{10}R^{10}$;

Each $R^8$ is independently a 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms independently selected from O, N, or S, which may be saturated or unsaturated, and wherein 0, 1, 2, 3 or 4 atoms of each ring may be substituted by a substituent independently selected from C1-C10 alkyl; C2-C10 alkenyl; C2-C10 alkynyl; C3-C10 cycloalkyl; C4-C10 cycloalkenyl; aryl; $R^9$; halo; sulfur; oxygen; $CF_3$; $SR^5$; $OR^5$; $OC(O)R^5$; $NR^5R^5$; $NR^5R^6$; $NR^6R^6$; $COOR^5$; $NO_2$; CN; $C(O)R^5$; $C(O)NR^5R^5$; $S(O)_nNR^5R^5$; $NR^5C(O)NR^5R^5$; $NR^5C(O)R^9$; $NR^5S(O)_nNR^5R^5$; $NR^5S(O)_nR^9$; C1-C10 alkyl substituted with 1-3 independent $R^7$, $R^9$ or aryl; or C2-C10 alkenyl substituted with 1-3 independent $R^7$, $R^9$ or aryl;

Each $R^9$ is independently a 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms independently selected from O, N, or S, which may be saturated or unsaturated, and wherein 0, 1, 2 or 3 atoms of each ring may be substituted by a substituent independently selected from C1-C10 alkyl; C2-C10 alkenyl; C2-C10 alkynyl; C3-C10 cycloalkyl; C4-C10 cycloalkenyl; halo; sulfur; oxygen; $CF_3$; $SR^{10}$; $OR^{10}$; $NR^{10}R^{10}$; $NR^{10}R^{11}$; $NR^{11}R^{11}$; $COOR^{10}$; $NO_2$; CN; $S(O)_nR^{10}$; $S(O)_nNR^{10}R^{10}$; $C(O)R^{10}$; or $C(O)NR^{10}R^{10}$;

Each $R^{10}$ is independently H; C1-C10 alkyl; C2-C10 alkenyl; C2-C10 alkynyl; C3-C10 cycloalkyl; C4-C10 cycloalkenyl; haloalkyl; C1-C10 alkyl optionally substituted with 1-3 independent C1-C10 alkyl, C2-C10 alkenyl, C2-C10 alkynyl, C3-C10 cycloalkyl, C4-C10 cycloalkenyl, halo, $CF_3$, $OR^{12}$, $SR^{12}$, $NR^{12}R^{12}$, $COOR^{12}$, $NO_2$, CN, $C(O)R^{12}$, $C(O)NR^{12}R^{12}$, $NR^{12}C(O)R^{12}$, $N(R^{12})(COOR^{12})$, $S(O)_nNR^{12}R^{12}$, or $OC(O)R^{12}$; or phenyl optionally substituted with 1-3 independent C1-C10 alkyl, C2-C10 alkenyl, C2-C10 alkynyl, C3-C10 cycloalkyl, C4-C10 cycloalkenyl, halo, $CF_3$, $OR^{12}$, $SR^{12}$, $NR^{12}R^{12}$, $COOR^{12}$, $NO_2$, CN, $C(O)R^{12}$, $C(O)NR^{12}R^{12}$, $NR^{12}C(O)R^{12}$, $N(R^{12})(COOR^{12})$, $S(O)_n NR^{12}R^{12}$, or $OC(O)R^{12}$;

Each $R^{11}$ is independently $C(O)R^{10}$, $COOR^{10}$, $C(O)NR^{10}R^{10}$ or $S(O)_nR^{10}$;

Each $R^{12}$ is independently H; C1-C10 alkyl; C2-C10 alkenyl; C2-C10 alkynyl; C3-C10 cycloalkyl; C4-C10 cycloalkenyl; C1-$C_{10}$ alkyl substituted with 1-3 independent C2-C10 alkenyl, C2-C10 alkynyl, C3-C10 cycloalkyl, C4-C10 cycloalkenyl, halo, $CF_3$, $OR^{13}$, $SR^{13}$, $NR^{13}R^{13}$, $COOR^{13}$, $NO_2$, CN, $C(O)R^{13}$, $C(O)NR^{13}R^{13}$, $NR^{13}C(O)R^{13}$, or $OC(O)R^{13}$; or phenyl optionally substituted with 1-3 independent C1-$C_{10}$ alkyl, C2-C10 alkenyl, C2-C10 alkynyl, C3-C10 cycloalkyl, C4-C10 cycloalkenyl, halo, $CF_3$, $OR^{13}$, $SR^{13}$, $NR^{13}R^{13}$, $COOR^{13}$, $NO_2$, CN,$C(O)R^{13}$, $C(O)NR^{13}R^{13}$, $NR^{13}C(O)R^{13}$, or $OC(O)R^{13}$;

Each $R^{13}$ is independently H; C1-C10 alkyl; C2-C10 alkenyl; C2-C10 alkynyl; C3-C10 cycloalkyl; C4-C10 cycloalkenyl; C1-C10 alkyl optionally substituted with halo, $CF_3$, $OR^{14}$, $SR^{14}$, $NR^{14}R^{14}$, $COOR^{14}$, $NO_2$, CN; or phenyl optionally substituted with halo, $CF_3$, $OR^{14}$, $SR^{14}$, $NR^{14}R^{14}$, $COOR^{14}$, $NO_2$, CN;

Each $R^{14}$ is independently H; C1-C10 alkyl; C3-C10 cycloalkyl or phenyl;

Each $R^{15}$ is independently H; $CF_3$; CN; $COOR^5$; or C1-C10 alkyl substituted with 1-3 independent $OR^5$, $SR^5$, or $NR^5R^5$;

Each $R^{16}$ is independently H, C1-$C_{10}$ alkyl; C2-C10 alkenyl; C2-C10 alkynyl; C3-C10 cycloalkyl; C4-C10 cycloalkenyl; aryl; $R^8$; halo; haloalkyl; $CF_3$; $COOR^5$; $C(O)R^5$; $C(O)C(O)R^5$; $C(O)NR^5R^5$; $S(O)_nR^5$: $S(O)_n NR^5R^5$; C1-C10 alkyl substituted with 1-3 independent aryl, $R^7$ or $R^8$; or C2-C10 alkenyl substituted with 1-3 independent aryl, $R^7$ or $R^8$;

Each $R^{17}$ is independently H; C1-C10 alkyl; C2-C10 alkenyl; C2-C10 alkynyl; C3-C10 cycloalkyl; C4-C10 cycloalkenyl; aryl; $R^8$; halo; haloalkyl; $CF_3$; $SR^5$; $OR^{18}$; $OC(O)R^5$; $NR^5R^5$; $NR^5R^6$; $COOR^5$; $NO_2$; CN; $C(O)R^5$; $C(O)C(O)R^5$; $C(O)NR^5R^5$; $S(O)_nR^5$: $S(O)_n NR^5R^5$; $NR^5C(O)NR^5R^5$; $NR^5C(O)C(O)R^5$; $NR^5C(O)R^5$; $NR^5(COOR^5)$; $NR^5C(O)R^8$; $NR^5S(O)_n NR^5R^5$; $NR^5S(O)_nR^5$; $NR^5S(O)_nR^8$; $NR^5C(O)C(O)NR^5R^5$; $NR^5C(O)C(O)NR^5R^6$; C1-C10 alkyl substituted with 1-3 independent aryl, $R^7$ or $R^8$; or C1-C10 alkenyl substituted with 1-3 independent aryl, $R^7$ or $R^8$;

Each $R^{18}$ is independently aryl; $R^8$; C1-C10 alkyl substituted with 1-3 independent aryl, $CF_3$, $OC(O)R^{10}$, $NHR^{19}$, $NR^{10}R^{11}$, $NR^{11}R^{11}$, $COOR^{10}$, $NO_2$, CN, $C(O)R^{10}$, $OC(O)NR^{10}R^{10}$, $C(O)NR^{10}R^{10}$, $N(R^{10})C(O)R^{10}$, $N(R^{10})(COOR^{10})$, $S(O)_n NR^{10}R^{10}$, or $R^8$; or C2-C10 alkenyl substituted with 1-3 independent aryl, $CF_3$, $OC(O)R^{10}$, $NHR^{19}$, $NR^{10}R^{11}$, $NR^{11}R^{11}$, $COOR^{10}$, $NO_2$, CN, $C(O)R^{10}$, $OC(O)NR^{10}R^{10}$, $C(O)NR^{10}R^{10}$, $N(R^{10})C(O)R^{10}$, $N(R^{10})(COOR^{10})$, $S(O)_n NR^{10}R^{10}$, or $R^8$;

Each $R^{19}$ is independently C2-C10 alkenyl; C2-C10 alkynyl; C3-C10 cycloalkyl; C4-C10 cycloalkenyl; aryl; $R^9$; haloalkyl;

Each $R^{20}$ is independently $NR^5R^6$; $OR^5$; $SR^5$; or halo;

Each haloalkyl is independently a C1-C10 alkyl substituted with one or more halogen atoms, selected from F, Cl, Br, or I, wherein the number of halogen atoms may not exceed that number that results in a perhaloalkyl group;

Each aryl is independently a 6-carbon monocyclic, 10-carbon bicyclic or 14-carbon tricyclic aromatic ring system optionally substituted with 1-3 independent C1-C10 alkyl; C2-C10 alkenyl; C2-C10 alkynyl; C3-C10 cycloalkyl; C4-C10 cycloalkenyl; $R^9$; halo; haloalkyl; $CF_3$; $OR^{10}$; $SR^{10}$; $NR^{10}R^{10}$; $NR^{10}R^{11}$; $COOR^{10}$; $NO_2$; CN; $C(O)R^{10}$; $C(O)C(O)R^{10}$; $C(O)NR^{10}R^{10}$; $N(R^{10})C(O)NR^{10}R^{10}$; $N(R^{10})C(O)R^{10}$; $N(R^{10})S(O)_nR^{10}$; $N(R^{10})(COOR^{10})$; $NR^{10}C(O)C(O)R^{10}$; $NR^{10}C(O)R^9$; $NR^{10}S(O)_nR^{10}R^{10}$; $NR^{10}S(O)_nR^9$; $NR^{12}C(O)C(O)NR^{12}R^{12}$; $S(O)_nR^{10}$; $S(O)_n NR^{10}R^{10}$; $OC(O)R^{10}$; C1-C10 alkyl substituted with 1-3 independent $R^9$, halo, $CF_3$,$OR^{10}$, $SR^{10}$, $OC(O)R^{10}$, $NR^{11}R^{11}$, $NR^{10}R^{10}$, $NR^{10}R^{11}$, $COOR^{10}$, $NO_2$, CN, $C(O)R^{10}$, $OC(O)NR^{10}R^{10}$, $C(O)NR^{10}R^{10}$; $N(R^{10})C(O)R^{10}$, $N(R^{10})(COOR^{10})$, $S(O)_n NR^{10}R^{10}$; $R^{10}$; or C2-C10 alkenyl substituted with 1-3 independent $R^9$, halo, $CF_3$, $OR^{10}$, $SR^{10}$, $OC(O)R^{10}$, $NR^{11}R^{11}$, $NR^{10}R^{10}$, $NR^{10}R^{11}$, $COOR^{10}$, $NO_2$, CN, $C(O)R^{10}$, $OC(O)NR^{10}R^{10}$, $C(O)NR^{10}R^{10}$, $N(R^{10})C(O)R^{10}$, $N(R^{10})$ $(COOR^{10})$, $S(O)_n NR^{10}R^{10}$;

Each heterocyclyl is independently a 5-8 membered nonaromatic monocyclic, 8-12 membered nonaromatic bicyclic, or 11-14 membered nonaromatic tricyclic, ring system comprising 1-4 heteroatoms if monocyclic, 1-8 heteroatoms if bicyclic, or 1-10 heteroatoms if tricyclic, said heteroatoms independently selected from O, N, or S;

Each heteroaryl is independently a 5-8 membered aromatic monocyclic, 8-12 membered aromatic bicyclic, or 11-14 membered aromatic tricyclic ring system comprising 1-4 heteroatoms if monocyclic, 1-8 heteroatoms if bicyclic, or 1-10 heteroatoms if tricyclic, said heteroatoms independently selected from O, N, or S.

In alternate embodiments, the compounds are of the formula above, wherein each $R^1$ is independently $NHR^3$, and each $R^2$ is independently $NHR^3$; alternatively wherein each $R^1$ is independently $NHR^3$, and each $R^2$ is independently one of the formulae:

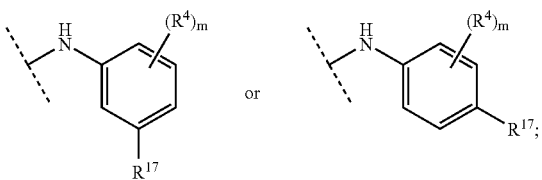

alternatively wherein each $R^1$ is independently $NHR^3$, wherein the $R^3$ group in $R^1$ is heteroaryl substituted with 1-4 independent $R^4$ on each ring, (and alternatively wherein at least one of said $R^4$ is not H), and each $R^2$ is independently one of the formulae:

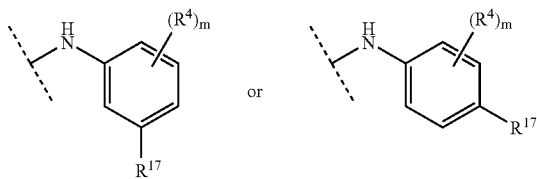

wherein m is 0-3, alternatively m is 1 or 2, alternatively m is 1;

alternatively wherein each $R^1$ is independently $NHR^3$; wherein the $R^3$ group in $R^1$ is pyrazolyl, triazolyl, imidazolyl, pyrrolyl, indolyl, or indazolyl, each substituted with 1-4 independent $R^4$ on each ring, (and alternatively wherein at least one of said $R^4$ is not H, and alternatively wherein at least one of said $R^4$ is not H and no $R^4$ may be methyl), and each $R^2$ is independently one of the formulae:

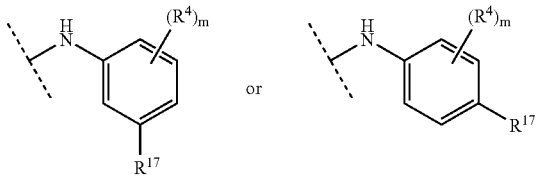

wherein m is 0-3, alternatively m is 1 or 2, alternatively m is 1;
alternatively wherein each $R^1$ is independently $R^3$, and each $R^2$ is independently $NHR^3$; alternatively wherein each $R^1$ is independently heterocyclyl substituted with 1-4 independent $R^4$ on each ring, (and alternatively wherein at least one of said $R^4$ is not H), and each $R^2$ is independently $NHR^3$, wherein each $R^1$ may not be 1-alkyl-1,2,3,4-tetrahydroisoquinolin-2-yl (wherein alkyl is defined as methyl, ethyl or propyl);
alternatively wherein each $R^1$ is independently heterocyclyl substituted with 1-4 independent $R^4$ on each ring, (and alternatively wherein at least one of said $R^4$ is not H), and each $R^2$ is independently one of the formulae:

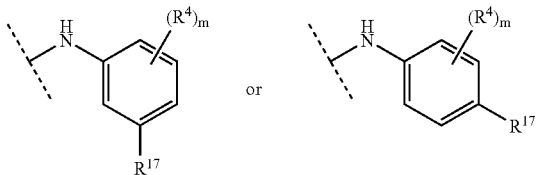

wherein each $R^1$ may not be 1-alkyl-1,2,3,4-tetrahydroisoquinolin-2-yl (wherein alkyl is defined as methyl, ethyl or propyl);
alternatively wherein each $R^1$ is independently heterocyclyl substituted with 1-4 independent $R^4$ on each ring, (and alternatively wherein at least one of said $R^4$ is not H), wherein said heterocyclyl comprises at least one nitrogen heteroatom and said heterocyclyl is attached at said nitrogen heteroatom;
alternatively wherein each $R^1$ is independently heterocyclyl substituted with 1-4 independent $R^4$ on each ring, (and alternatively wherein at least one of said $R^4$ is not H), wherein said heterocyclyl comprises at least one nitrogen heteroatom and said heterocyclyl is attached at said nitrogen heteroatom, and each $R^2$ is independently $NHR^3$, wherein each $R^1$ may not be 1-alkyl-1,2,3,4-tetrahydroisoquinolin-2-yl (wherein alkyl is defined as methyl, ethyl or propyl);
alternatively wherein each $R^1$ is independently pyrrolyl substituted with 1-4 independent $R^4$ on each ring, (and alternatively wherein at least one of said $R^4$ is not H), and each $R^2$ is independently $NHR^3$;
alternatively wherein each $R^1$ is independently pyrazolyl substituted with 1-4 independent $R^4$ on each ring, (and alternatively wherein at least one of said $R^4$ is not H), and each $R^2$ is independently $NHR^3$;
alternatively wherein each $R^1$ is independently benzimidazolyl substituted with 1-4 independent $R^4$ on each ring, (and alternatively wherein at least one of said $R^4$ is not H), and each $R^2$ is independently $NHR^3$;
alternatively wherein each $R^1$ is independently heteroaryl substituted with 1-4 independent $R^4$ on each ring, (and alternatively wherein at least one of said $R^4$ is not H), wherein said heteroaryl comprises at least one nitrogen heteroatom and said heteroaryl is attached at said nitrogen heteroatom, and said heteroaryl is not unsubstituted pyrrolyl;
alternatively wherein each $R^1$ is independently heteroaryl substituted with 1-4 independent $R^4$ on each ring, (and alternatively wherein at least one of said $R^4$ is not H), wherein said heteroaryl comprises at least one nitrogen heteroatom and said heteroaryl is attached at said nitrogen heteroatom, and said heteroaryl is not unsubstituted pyrrolyl, and each $R^2$ is independently $NHR^3$;
alternatively wherein each $R^1$ is independently heteroaryl substituted with 1-4 independent $R^4$ on each ring, (and alternatively wherein at least one of said $R^4$ is not H), wherein said heteroaryl comprises at least one nitrogen heteroatom and said heteroaryl is attached at said nitrogen heteroatom, and said heteroaryl is not unsubstituted pyrrolyl, and each $R^2$ is independently one of the formulae:

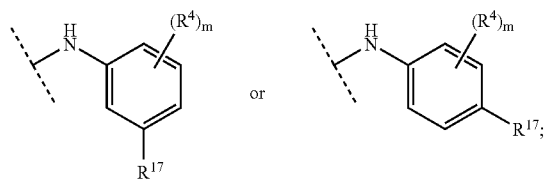

alternatively wherein each $R^2$ is independently $NHR^3$, and each $R^1$ is independently of the formula:

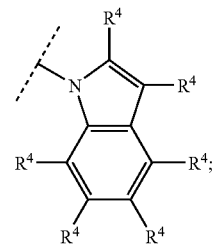

alternatively wherein each $R^2$ is independently $NHR^3$; and each $R^1$ is independently of the formula:

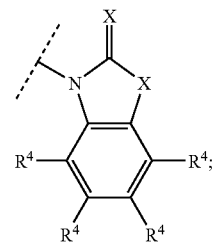

alternatively wherein each $R^2$ is independently $NHR^3$, and each $R^1$ is independently of the formula:

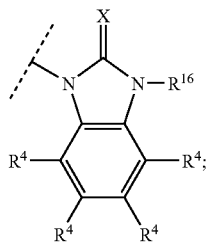

alternatively wherein each $R^2$ is independently $NHR^3$, and each $R^1$ is independently of the formula:

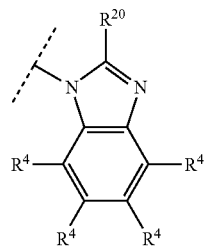

alternatively wherein $R^2$ is independently $NHR^5$;
alternatively wherein each $R^1$ is independently any one of following formulae:

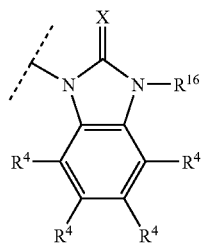 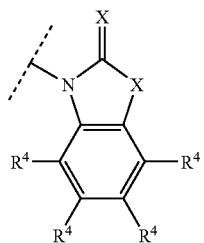

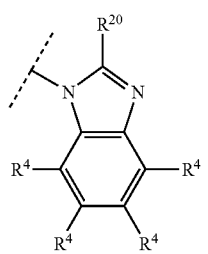 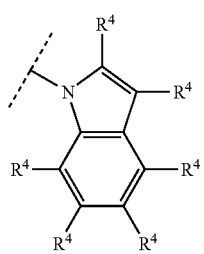

and alternatively wherein $R^1$ is independently any of formulae above and $R^2$ is independently $NHR^5$.

In an alternate embodiment, the compound is of any of the formulae herein, wherein $R^1$ is independently $NHR^3$ and $R^2$ is independently

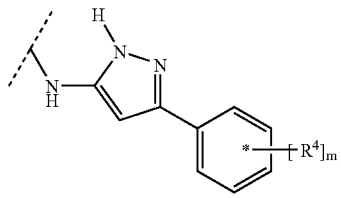

wherein $R^4$ is as defined herein and m is 0, 1, 2, or 3.

In an alternate embodiment, the compound is of any of the formulae herein, wherein $R^1$ is independently $NHR^3$ and $R^2$ is independently

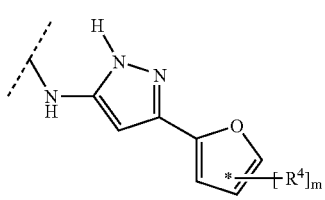

wherein $R^4$ is as defined herein and m is 0, 1, 2, or 3.

Alternate embodiments are those of any of the formulae herein wherein each $R^3$ is independently phenyl substituted with 1-4 independent $R^4$, wherein at least one $R^4$ is not H; and those of any of the formulae herein wherein each $R^3$ is independently heteroaryl substituted with 1-4 independent $R^4$, wherein at least one $R^4$ is not H.

Alternate embodiments are those of any of the formulae herein wherein each $R^1$ is independently phenyl substituted with 1-4 independent $R^4$, wherein at least one $R^4$ is not H; and those of any of the formulae herein wherein each $R^1$ is independently heteroaryl substituted with 1-4 independent $R^4$, wherein at least one $R^4$ is not H; and those of any of the formulae herein wherein each $R^1$ is independently heterocyclyl substituted with 1-4 independent $R^4$, wherein at least one $R^4$ is not H.

Alternate embodiments are those of any of the formulae herein wherein each $R^4$ is independently $C(O)NR^5R^5$; or C1-C10 alkyl substituted with 1-3 independent $C(O)NR^5R^5$.

Alternate embodiments are those of any of the formulae herein wherein each $R^4$ is independently $R^8$; alternatively wherein each $R^4$ is independently a 5-8 membered monocyclic saturated ring comprising 1-3 heteroatoms, said heteroatoms independently selected from O, N, or S; or alternatively wherein each $R^4$ is independently a 5-8 membered monocyclic saturated ring comprising 1-3 heteroatoms, said heteroatoms independently selected from O, N, or S, wherein 1, 2, or 3 atoms of each ring may be substituted by a substituent independently selected from C1-C10 alkyl; C2-C10 alkenyl; C2-C10 alkynyl; C3-C10 cycloalkyl; C4-C10 cycloalkenyl; aryl; $R^9$; halo; sulfur; oxygen; $CF_3$; $SR^5$; $OR^5$; $OC(O)R^5$; $NR^5R^5$; $NR^5R^6$; $NR^6R^6$; $COOR^5$; $NO_2$; CN; $(O)R^5$; $C(O)NR^5R^5$; $S(O)_nNR^5R^5$; $NR^5C(O)$ $NR^5R^5$; $NR^5C(O)R^9$; $NR^5S(O)_nNR^5R^5$; $NR^5S(O)_nR^9$;

C1-C10 alkyl substituted with 1-3 independent $R^7$, $R^9$ or aryl; or C2-C10 alkenyl substituted with 1-3 independent $R^7$, $R^9$ or aryl.

Alternate embodiments are those of any of the formulae herein wherein each $R^4$ is independently C1-C10 alkyl substituted with 1-3 independent $R^7$; alternatively C1-C10 alkyl substituted with 1-3 independent $R^8$; or alternatively $OR^5$ wherein each $R^5$ is independently C1-C6 alkyl substituted with 1 independent $R^7$ or $R^8$.

Alternate embodiments are those of any of the formulae herein wherein each $R^2$ is independently $NHR^3$.

Alternate embodiments are those of any of the formulae herein wherein each heteroaryl is independently a 5-6 membered monocylic ring; alternatively a 9-10 membered bicyclic ring; or alternatively a 13-14 membered tricyclic ring.

Alternate embodiments are those of any of the formulae herein wherein each heteroaryl is independently a 5-6 membered monocylic ring comprising 1-3 heteroatoms, alternatively 1-2 heteroatoms, or alternatively 1 heteroatom; alternatively a 9-10 membered bicyclic ring comprising 1-6 heteroatoms, alternatively 1-3 heteroatoms, alternatively 1-2 heteroatoms, or alternatively 1 heteroatom; or alternatively a 13-14 membered tricyclic ring comprising 1-6 heteroatoms, alternatively 1-3 heteroatoms, alternatively 1-2 heteroatoms, or alternatively 1 heteroatom.

Alternate embodiments are those of any of the formulae herein wherein each heterocyclyl is independently a 5-6 membered monocylic ring; alternatively a 9-10 membered bicyclic ring; or alternatively a 13-14 membered tricyclic ring.

Alternate embodiments are those of any of the formulae herein wherein each heterocyclyl is independently a 5-6 membered monocylic ring comprising 1-3 heteroatoms, alternatively 1-2 heteroatoms, or alternatively 1 heteroatom; alternatively a 9-10 membered bicyclic ring comprising 1-6 heteroatoms, alternatively 1-3 heteroatoms, alternatively 1-2 heteroatoms, or alternatively 1 heteroatom; or alternatively a 13-14 membered tricyclic ring comprising 1-6 heteroatoms, alternatively 1-3 heteroatoms, alternatively 1-2 heteroatoms, or alternatively 1 heteroatom.

Alternate embodiments are those of any of the formulae herein wherein each $R^{17}$ is independently C2-C10 alkenyl; C2-C10 alkynyl; C3-C10 cycloalkyl; C4-C10 cycloalkenyl; aryl; $R^8$; haloalkyl; $CF_3$; $SR^5$; $OR^{18}$; $OC(O)R^5$; $NR^5R^5$; $NR^5R^6$; $COOR^5$; $NO_2$; CN; $C(O)R^5$;$C(O)C(O)R^5$; $C(O)NR^5R^5$; $S(O)_nR^5$; $S(O)_nNR^5R^5$; $NR^5C(O)NR^5R^5$; $NR^5C(O)C(O)R^5$; $NR^5C(O)R^5$; $NR^5(COOR^5)$; $NR^5C(O)R^8$; $NR^5S(O)_nNR^5R^5$; $NR^5S(O)_nR^5$; $NR^5S(O)R_nR^8$;$NR^5C(O)C(O)NR^5R^5$; $NR^5C(O)C(O)NR^5R^6$; C1-$C_{10}$ alkyl substituted with 1-3 independent aryl, $R^7$ or $R^8$; or C1-C10 alkenyl substituted with 1-3 independent aryl, $R^7$ or $R^8$.

Alternate embodiments are those of any of the formulae herein wherein each $R^{18}$ is independently C1-C6 alkyl substituted with 1-3, alternatively 1-2, or alternatively 1 independent aryl, $CF_3$, $OC(O)R^{10}$, $NHR^{19}$, $NR^{10}R^{11}$, $NR^{11}R^{11}$, $COOR^{10}$, $NO_2$, CN, $C(O)R^{10}$, $OC(O)NR^{10}R^{10}$, $C(O)NR^{10}R^{10}$, $N(R^{10})C(O)R^{10}$, $N(R^{10})(COOR^{10})$, $S(O)_n NR^{10}R^{10}$, or $R^8$.

Alternate embodiments are those of any of the formulae herein wherein each m is 0-3, alternatively m is 1 or 2, or alternatively m is 1.

The invention also relates to methods of inhibiting enzyme or polypeptide activity, particularly of an enzyme or polypeptide described herein, such as a phosphoryl transferase, or alternatively a kinase, in a mammal comprising the step of administering to said mammal a compound of any of the formulae described herein or a composition comprising a compound of any of the formulae described herein. In one embodiment, the invention relates to a method of inhibiting phosphoryl transferase, alternatively kinase, activity in a mammal comprising the step of administering to said mammal a compound, or a composition comprising a compound, of any one of the formulae described herein. Preferably, the mammal is a human.

In another embodiment, the invention relates to a method of inhibiting enzyme activity in a mammal comprising the step of administering to said mammal a compound, or a composition comprising a compound, of any of the formulae described herein. Preferably, the mammal is a human.

The invention also relates to methods of treating disease and/or disease symptoms, particularly those mediated by an enzyme or polypeptide described herein, such as phosphoryl transferase mediated, or kinase mediated, disease or disease symptoms, in a mammal comprising the step of administering to said mammal a compound of any of the formulae described herein or a composition comprising a compound of any of the formulae described herein. Such diseases or disease symptoms are described herein. "Kinase mediated" disease or disease symptoms refers to disease or disease symptoms in which kinase activity is involved. In one embodiment, this invention relates to a method of treating disease or disease symptoms, particularly kinase mediated disease or disease symptoms, in a mammal comprising the step of administering to said mammal a compound, or a composition comprising a compound, of any of the formulae described herein. Preferably, the mammal is a human.

In an alternate embodiment, this invention relates to a method of treating disease or disease symptoms in a mammal comprising the step of administering to said mammal a compound, or a composition comprising a compound, of any of the formulae described herein. Preferably, the mammal is a human.

In the compounds described herein, the term "halo" refers to any radical of fluorine, chlorine, bromine or iodine. The terms "alkyl", "alkenyl" and "alkynyl" refer to hydrocarbon chains that may be straight-chain or branched-chain, containing the indicated number of carbon atoms. For example, C1-C10 indicates the group may have from 1 to 10 (inclusive) carbon atoms in it. The terms "ring" and "ring system" refer to a ring comprising the delineated number of atoms, said atoms being carbon or, where indicated, a heteroatom such as nitrogen, oxygen or sulfur. The ring itself, as well as any substitutents thereon, may be attached at any atom that allows a stable compound to be formed. The term "nonaromatic" ring or ring system refers to the fact that at least one, but not necessarily all, rings in a bicylic or tricyclic ring system is nonaromatic.

Leaving groups are species that may be detached from a molecule during a reaction and are known in the art. Examples of such groups include, but are not limited to, halogen groups (e.g., I, Br, F, Cl), sulfonate groups (e.g., mesylate, tosylate), sulfide groups (e.g., $SCH_3$), and the like. Nucleophiles are species that may be attached to a molecule during reaction and are known in the art. Examples of such groups include, but are not limited to, amines, Grignard reagents, anionic species (e.g., alkoxides, amides, carbanions) and the like.

In the methods described herein, said mammal is preferably a human. The inhibitors described herein, however, are useful in inhibiting kinase activity in human cells and useful in rodent (e.g., murine) and other species used as surrogates for investigating activity in vitro and in vivo in humans and against human kinases. The inhibitors described herein are also useful for investigating inhibition and activity of kinases originating from species other than humans.

The compounds and compositions described herein are useful for inhibition of kinase activity of one or more enzymes. Kinases include, for example, protein kinases (e.g., tyrosine, serone/threonine, histidine), lipid kinases (e.g., phosphatidylinositol kinases PI-3, PI-4) and carbohydrate kinases. Further information relating to kinase structure, function and and their role in disease or disease symptoms is available at the Protein Kinase Resource web site (http://www.sdsc.edu/Kinases/pk_home.html). Kinases may be of prokaryotic, eukaryotic, bacterial, viral, fungal or archaea origin. Specifically, the compounds described herein are useful as inhibitors of tyrosine, serine/threonine or histidine protein kinases, (including combinations or those of mixed specificity, that is for example, those that phosphorylate both tyrosine and serine/threonine residues) or lipid kinases. Examples of kinases that are inhibited by the compounds and compositions described herein and against which the methods described herein are useful include, but are not limited to, LCK, IRK (=INSR=Insulin receptor), IGF-1 receptor, SYK, ZAP-70, IRAK1, BLK, BMX, BTK, FRK, FGR, FYN, HCK, ITK, LYN, TEC, TXK, YES, ABL, SRC, EGF-R (=ErbB-1), ErbB-2 (=NEU=HER$^2$), ErbB-4, FAK, FGF1R (=FGR-1), FGF2R (=FGR-2), IKK-1 (=IKK-ALPHA=CHUK), IKK-2 (=IKK-BETA), MET (=c-MET), NIK, PDGF receptor ALPHA, PDGF receptor BETA, TIE1, TIE2 (=TEK), VEGFR1 (=FLT-1), VEGFR2 (=KDR), FLT-3, FLT-4, KIT, CSK, JAK1, JAK2, JAK3, TYK2, RIP, RIP-2, LOK, TAK1, RET, ALK, MLK3, COT, TRKA, PYK2, Activin-like Kinases (Alk1-7), EPHA(1-8), EPHB (1-6), RON, GSK3(A and B), Ilk, PDK1, SGK, Fes, Fer, MatK, Ark(1-3), Plk(1-3), LimK(1 and 2), RhoK, Pak (1-3), Raf(A,B, and C), PknB, CDK(1-10), Chk(1 and 2), CamK (I-IV), CamKK, CK1, CK2, PKR, Jnk(1-3), EPHB4, UL13, ORF47, ATM, PKA ($\alpha,\beta$ and $\gamma$), P38($\alpha,\beta$, and $\gamma$), Erk(1-3), PKB (including all PKB subtypes) (=AKT-1, AKT-2, AKT-3), and PKC (including all PKC subtypes). and all subtypes of these kinases. The compounds and compositions of the invention are therefore also particularly suited for treatment of diseases and disease symptoms that involve one or more of the aforementioned protein kinases. In one embodiment, the compounds, compositions or methods of this invention are particularly suited for inhibition of or treatment of disease or disease symptoms mediated by LCK, ZAP, LYN, EGFR, ERB-B2, KDR, c-MET or SYK. In another embodiment, the compounds, compositions or methods of this invention are particularly suited for inhibition of or treatment of disease or disease symptoms mediated by src-family kinases. In another embodiment, the compounds, compositions or methods of this invention are particularly suited for inhibition of or treatment of disease or disease symptoms mediated by kinases involved in angiogenesis. In another embodiment, the compounds, compositions or methods of this invention are particularly suited for inhibition of or treatment of disease or disease symptoms mediated by kinases in one of the kinase families defined by Hardie & Hanks, ed. supra., as in the Src family (PTK-I), Syk/Zap family (PTK-VI), EGFR family (PTK-X), HGF Family (PTK-XXI), Insulin receptor family (PTK-XVI), Tie/Tek family (PTK-XIII), Platelet-derived growth factor receptor family (PTK-XIV), or Fibroblast growth factor receptor family (PTK-XV). The compounds and compositions are also suited for regulating or modulating signal transduction in signal transduction pathways that involve one or more kinases, thus affecting events in a cell, and are therefor useful in methods for regulating or modulating signal transduction.

The inhibitors described herein are also useful for inhibiting the biological activity of any enzyme comprising greater than 90%, alternatively greater than 85%, or alternatively greater than 70% sequence homology with a phosphoryl transferase sequence, or alternatively a kinase sequence, including the kinases mentioned herein. The inhibitors described herein are also useful for inhibiting the biological activity of any enzyme comprising a subsequence, or variant thereof, of any enzyme that comprises greater than 90%, alternatively greater than 85%, or alternatively greater than 70% sequence homology with a phosphoryl transferase subsequence, or alternatively kinase subsequence, including subsequences of the kinases mentioned herein. Such subsequence preferably comprises greater than 90%, alternatively greater than 85%, or alternatively greater than 70% sequence homology with the sequence of an active site or subdomain of a phosphoryl transferase, or alternatively kinase, enzyme. The subsequences, or variants thereof, comprise at least about 300, or alternatively at least about 200, amino acids.

The inhibitors described herein are useful for inhibiting the biological activity of any enzyme that binds ATP and/or GTP and thus for treating disease or disease symptoms mediated by any enzyme that binds ATP and/or GTP. The inhibitors described herein are also useful for inhibiting the biological activity of any enzyme that binds adenine or guanine nucleotides. The inhibitors described herein are also useful for inhibiting the biological activity of any enzyme that is involved in phosphotransfer and thus for treating disease or disease symptoms mediated by any enzyme that is involved in phosphotransfer. The inhibitors described herein are also useful for inhibiting the biological activity of a polypeptide or enzyme having sequence homology with a phosphoryl transferase, or alternatively kinase, sequence and thus for treating disease or disease symptoms mediated by such polypeptide or enzyme. Such polypeptides or enzymes may be identified by comparison of their sequence with phosphoryl transferase, alternatively kinase, sequences and phosphoryl transferase, alternatively kinase, catalytic domain sequences. Such sequences may be found, for example, in databases such as GENEBANK, EMBO, or other similar databases known in the art. For example, one method of comparison involves the database PROSITE (http://expasy.hcuge.ch) (See, Hofmann K., Bucher P., Falquet L., Bairoch A., The PROSITE database, its status in 1999, Nucleic Acids Res. 27:215-219(1999)), containing "signatures" or sequence patterns (or motifs) or profiles of protein families or domains. Thus, the inhibitors described herein are useful for inhibiting the biological activity of a polypeptide or enzyme comprising a sequence that comprises a "signature" or sequence pattern or profile derived for, and identified in PROSITE as relating to kinases, and for treating disease or disease symptoms mediated by such polypeptide or enzyme. Examples of such PROSITE motifs or consensus patterns identified as relating to kinases include PS00107, PS00108, PS00109, PS0012, PS00583, PS00584, PS50011, PS50290, PS00915, and PS00916.

The inhibitors described herein are also useful for inhibiting the biological activity of ATP/GTP binding proteins. Many ATP/GTP binding proteins have consensus motifs that can be used to identify them. For example, PROSITE entry PDOC00017 titled "ATP/GTP-binding site motif A (P-loop)" describes a consensus pattern (called the A consensus sequence or the P-loop) for a large group of nucleotide binding proteins including ATP synthases, DNA and RNA helicases, ABC transporters, Kinesin and kinesin-like proteins, among many others. Other nucleotide binding proteins have motifs similar to this P-loop, but take slightly different forms. Examples of these include tubulins, lipid kinases and protein kinases. The ATP binding motif of protein kinases have also been defined within PROSITE entry PS00107. Yet other AGBPs have nothing similar to the P-loop motif. Examples of these include E1-E2 ATPases and the glycolytic kinases.

The compounds, compositions and methods described herein are useful in inhibiting kinase activity. As such, the compounds, compositions and methods of this invention are useful in treating kinase-mediated disease or disease symptoms in a mammal, particularly a human. Kinase mediated diseases are those wherein a protein kinase is involved in signaling, mediation, modulation, or regulation of the disease process or symptoms. Kinase mediated diseases are exemplified by the following disease classes: cancer, autoimmunological, metabolic, inflammatory, infection (bacterial, viral, yeast, fungal, etc.), diseases of the central nervous system, degenerative neural disease, allergy/asthma, dermatology, angiogenesis, neovascularization, vasculogenesis, cardiovascular, and the like.

The compounds, compositions and methods described herein are useful in treating or preventing diseases or their symptoms, including, transplant rejection (e.g., kidney, liver, heart, lung, pancreas (islet cells), bone marrow, cornea, small bowel, skin allografts or xenografts), graft versus host disease, osteoarthritis, rheumatoid arthritis, multiple sclerosis, diabetes, diabetic retinopathy, asthma, inflammatory bowel disease (Crohn's disease, ulcerative colitis), renal disease, cachexia, septic shock, lupus, diabetes mellitus, myasthenia gravis, psoriasis, dermatitis, eczema, seborrhea, Alzheimer's disease, Parkinson's disease, stem cell protection during chemotherapy, ex vivo selection or ex vivo purging for autologous or allogeneic bone marrow transplantation, leukemia (acute myeloid, chronic myeloid, acute lymphoblastic, etc.), cancer (breast, lung, colorectal, ovary, prostate, renal, squamous cell, prostate, glioblastoma, melanoma, pancreatic, Kaposi's sarcoma, etc.), ocular disease, retinopathies, (e.g., macular degeneration, diabetic retinopathy), corneal disease, glaucoma, bacterial infections, viral infections, fungal infections and heart disease, including but not limited to, restenosis. In one embodiment, the compositions and methods described herein are useful in treating preventing cancer, ocular disease, or retinopathies. In another embodiment, the compositions and methods described herein are useful in treating or preventing rheumatoid arthritis, transplant rejection, asthma or allergy, or their symptoms. In other embodiments, the compositions and methods described herein are useful in treating or preventing disease or disease symptoms involving hyperproliferative disorders, or alternatively, involving angiogenesis.

Another embodiment envisioned by this invention relates to the use of the kinase inhibitory compounds described herein for use as reagents that effectively bind to kinases. As reagents, the compounds of this invention, and their derivatives, may be derivatized to bind to a stable resin as a tethered substrate for affinity chromatography applications. Such derivatives may be used in purification of enzymes, including phosphoryl transferases and kinases. The compounds of this invention, and their derivatives, may also be modified (e.g., radiolabelled or affinity labelled, etc.) in order to utilize them in the investigation of enzyme or polypeptide characterization, structure, and/or function.

Additionally, the compounds described herein are useful as reagents for chemical validation of drug targets. These and other uses that characterize kinase inhibitors will be evident to those of ordinary skill in the art.

In another embodiment, the inhibitors described herein are useful for crystallizing or co-crystallizing with a protein kinase. Such crystals or crystal complexes may additionally comprise additional peptides and or metal ions. The crystals or crystal complexes may be used for investigation and determination of enzyme characteristics including, for example, structure of the kinase enzyme, enzyme active site domains, and inhibitor-enzyme interactions. This information is useful in developing inhibitor compounds with modified characteristics and for understanding structure-function relationships of the enzymes and their enzyme-inhibitor interactions.

In an alternate embodiment, the inhibitory compounds described herein may be used as platforms or scaffolds which may be utilized in combinatorial chemistry techniques for preparation of derivatives and/or chemical libraries of compounds. Such derivatives and libraries of compounds have kinase inhibitory activity and are useful for identifying and designing compounds possessing kinase inhibitory activity. Combinatorial techniques suitable for utilizing the compounds described herein are known in the art as exemplified by Obrecht, D. and Villalgrodo, J. M., Solid-Supported Combinatorial and Parallel Synthesis of Small-Molecular-Weight Compound Libraries, Pergamon-Elsevier Science Limited (1998), and include those such as the "split and pool" or "parallel" synthesis techniques, solid-phase and solution-phase techniques, and encoding techniques (see, for example, Czarnik, A. W., Curr. Opin. Chem. Bio., (1997) 1, 60. Thus, one embodiment relates to a method of using the compounds described in the formulae herein for generating derivatives or chemical libraries comprising: 1) providing a body comprising a plurality of wells; 2) providing one more compounds of the formulae described herein in each well; 3) providing an additional one or more chemicals in each well; 4) isolating the resulting one or more products from each well. An alternate embodiment relates to a method of using the compounds described in the formulae herein for generating derivatives or chemical libraries comprising: 1) providing one or more compounds of the formulae described herein attached to a solid support; 2) treating the one or more compounds of the formulae described herein attached to a solid support with one or more additional chemicals; 3) isolating the resulting one or more products from the solid support. In the methods described above, "tags" or identifier or labeling moieties may be attached to and/or detached from the compounds of the formulae herein or their derivatives, to facilitate tracking, identification or isolation of the desired products or their intermediates. Such moieties are known in the art. The chemicals used in the aforementioned methods may include, for example, solvents, reagents, catalysts, protecting group and deprotecting group reagents and the like. Examples of such chemicals are those that appear in the various synthetic and protecting group chemistry texts and treatises referenced herein.

The compounds of the formulae herein may be used to study the mechanism and role of enzymes in biological pathways and processes involving kinases. The compounds of the formulae herein may also be used as probes to identify new kinase enzymes or polypeptides with sequence homology to kinases. The inhibitor compounds may be tethered to a support or modified (e.g., tagged, radiolabeled or other identifiable detection method) such that the compound may be detected and isolated in the presence of the kinase enzyme or polypeptide. Thus, another embodiment relates to a method of identifying and/or isolating a kinase enzyme or polypeptide with sequence homology to a kinase enzyme sequence or subsequence, comprising, contacting a tethered or modified compound of any of the formulae herein with one or more polypeptides, isolating a polypeptide/inhibitor complex, and identifying or isolating the sequence of the polypeptide in the polypeptide/inhibitor complex. The identification of the polypeptide sequence may be performed while in the polypeptide/inhibitor complex or after the polypeptide is decomplexed from the tethered or modified compound of any of the formulae herein.

The compounds are also useful in inhibiting enzymes, including kinases, that play a role in plant metabolism regulation, plant growth or growth inhibition. As such the compounds and compositions of the invention are useful as plant growth regulators, and as herbicides. Such compositions comprise the compounds of the invention as well as any agricultural or other acceptable carrier for dispersal of the active compound, such carriers and their use are known in the art.

Table 1 lists representative individual compounds of the invention and compounds employed in the compositions and methods of this invention.

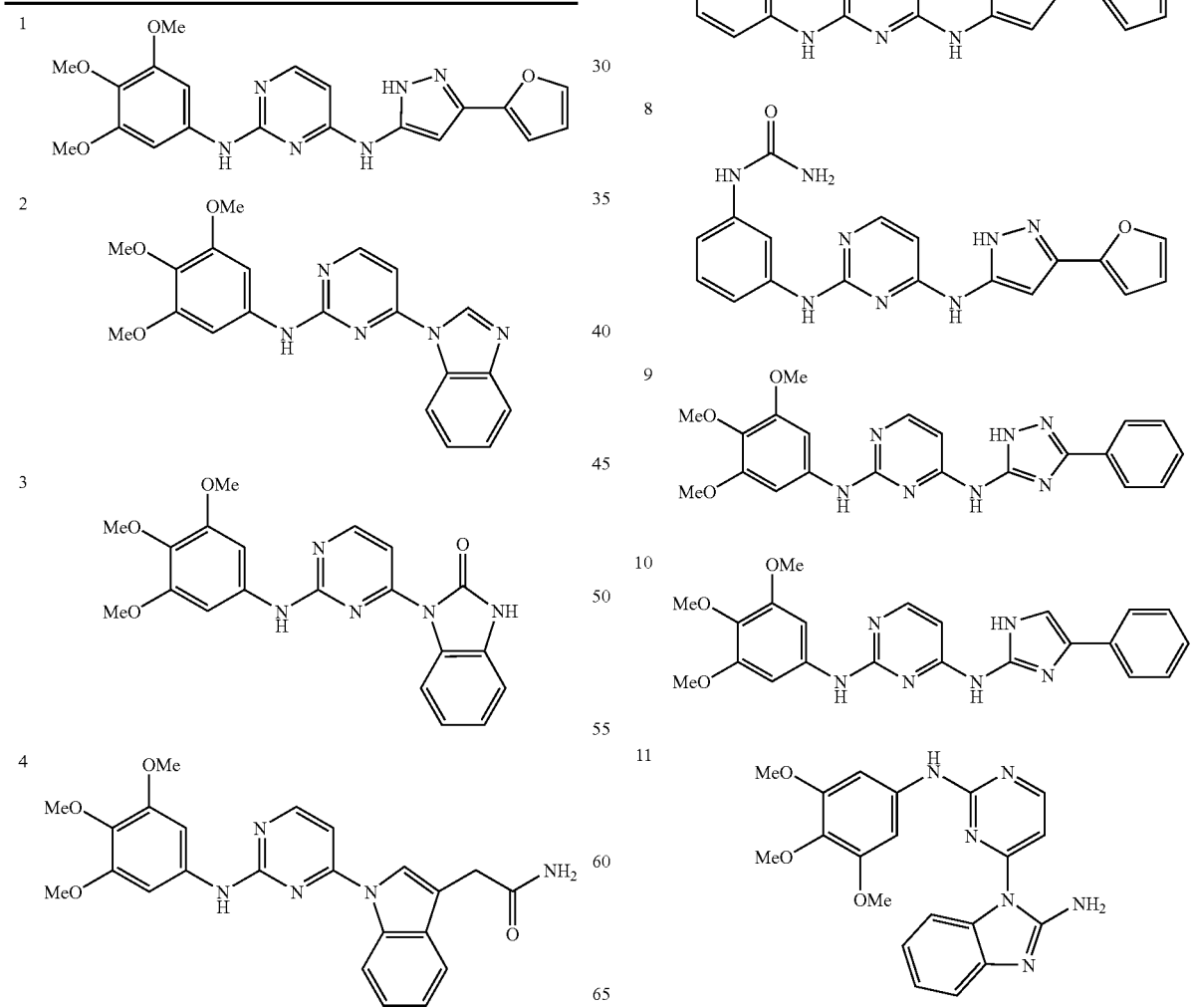

TABLE 1-continued
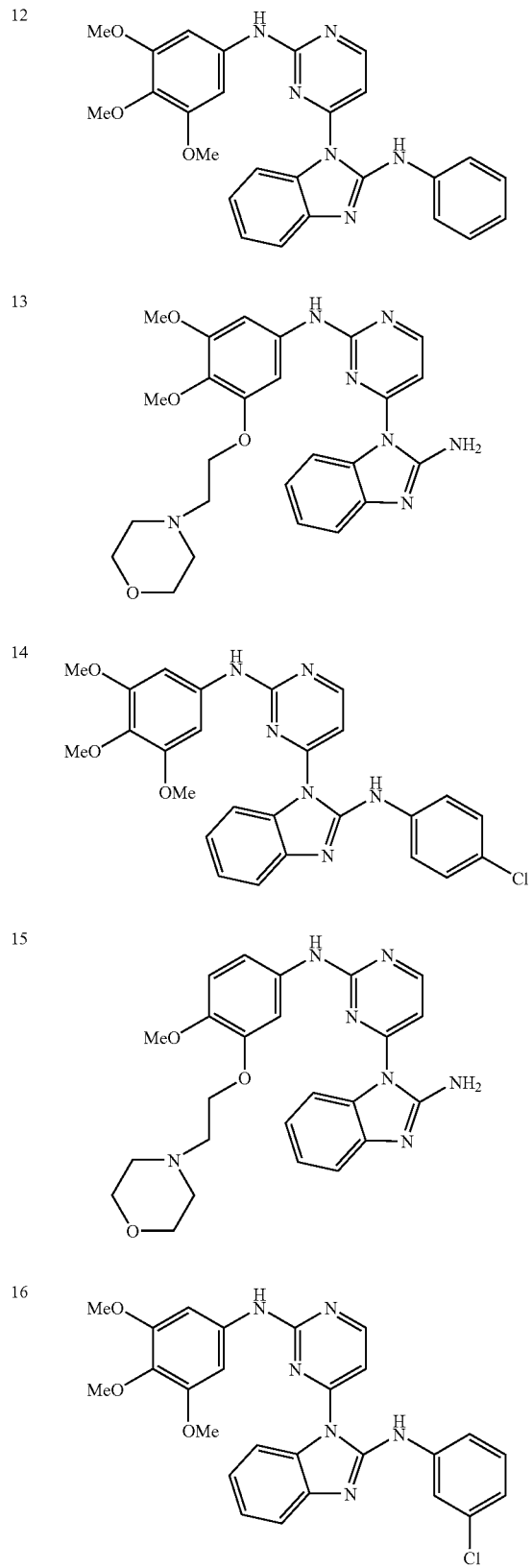
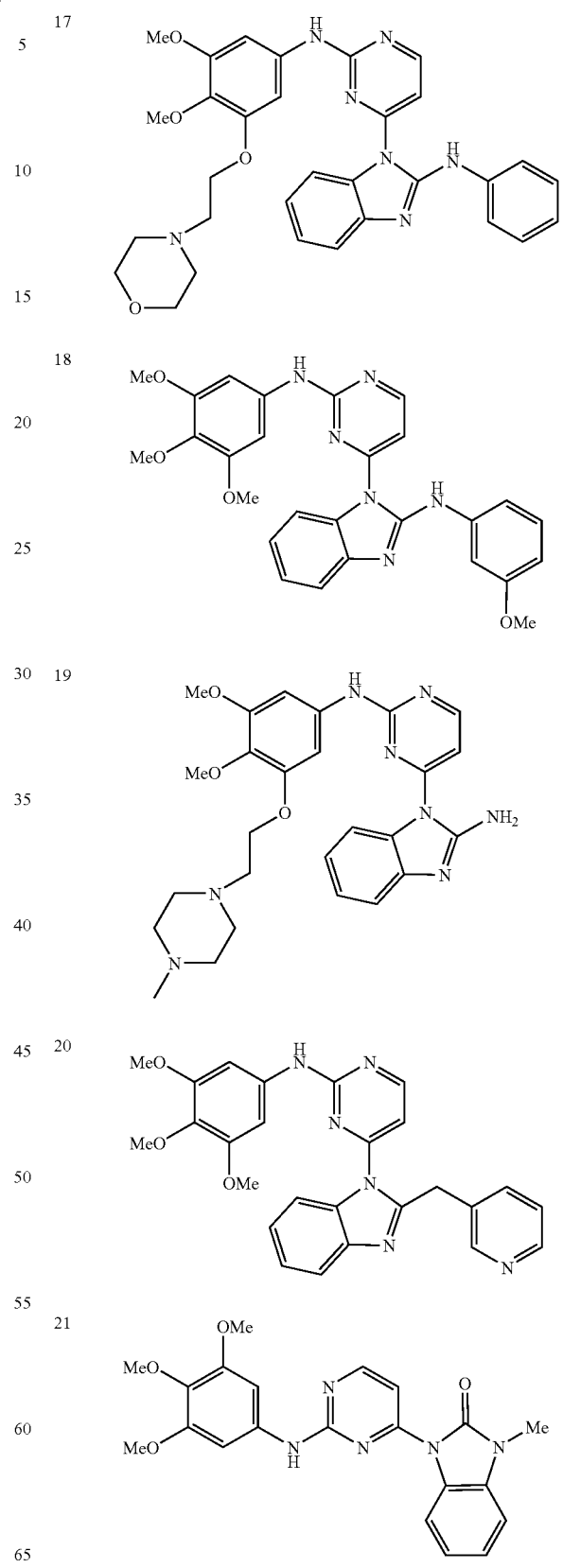

TABLE 1-continued
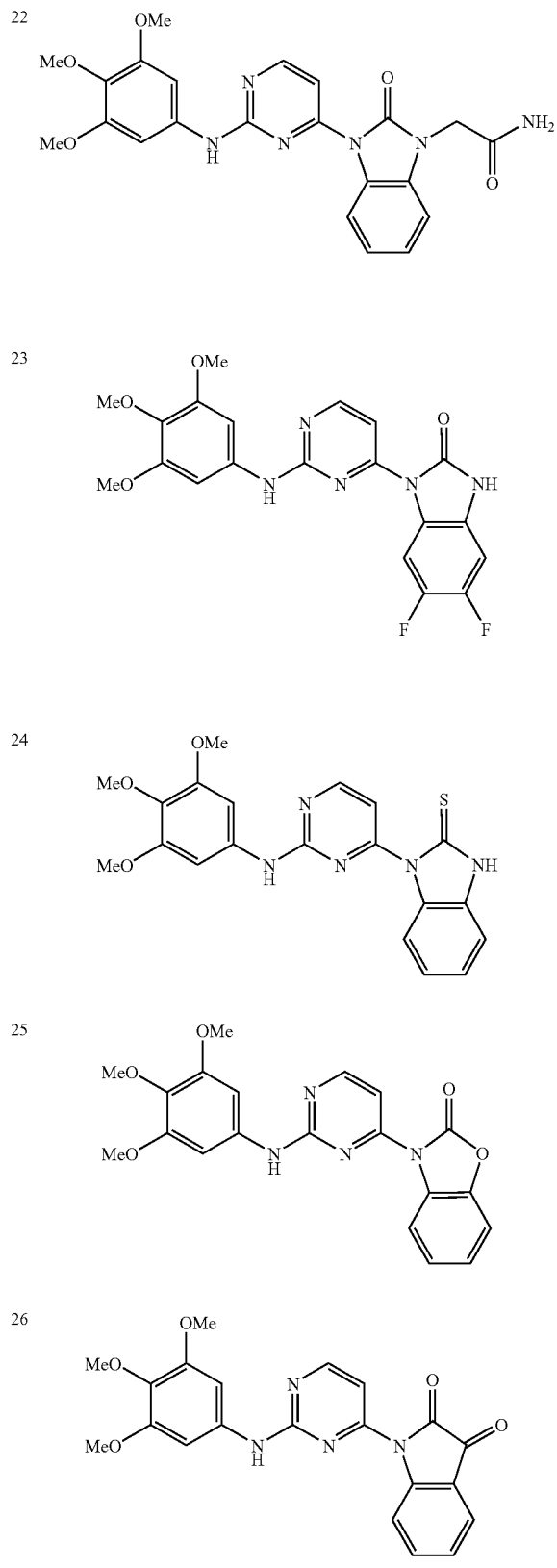
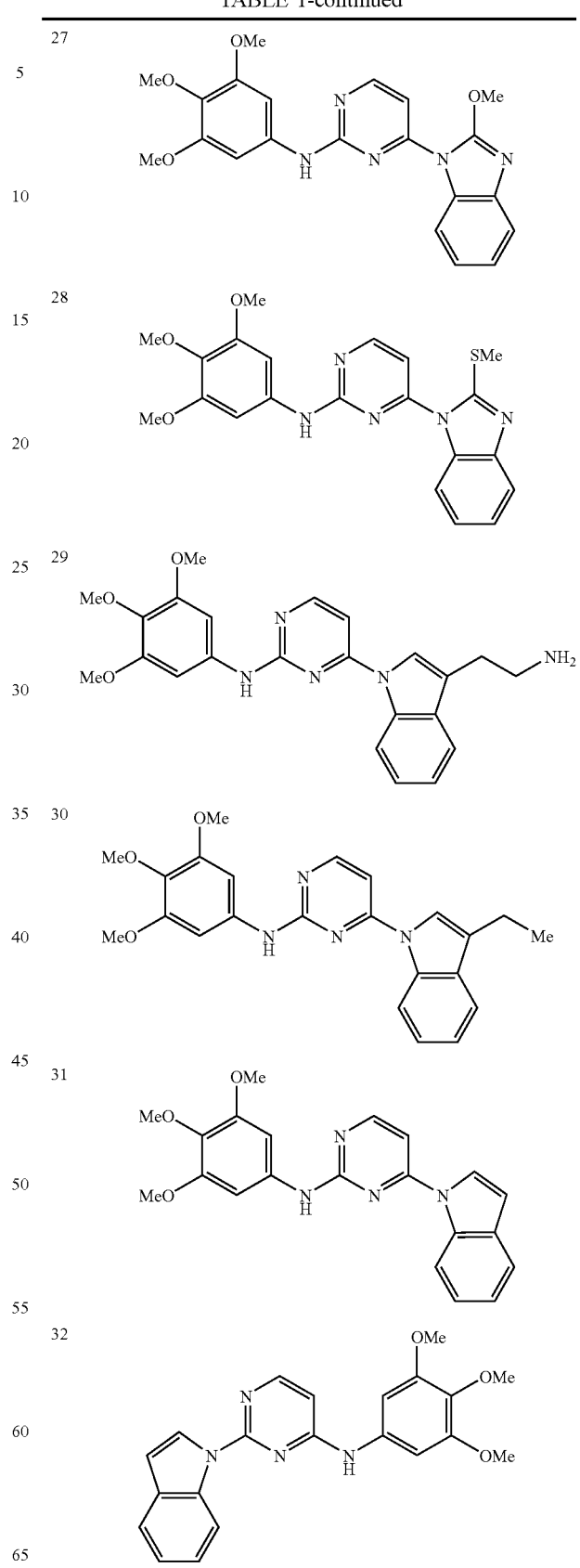

TABLE 1-continued
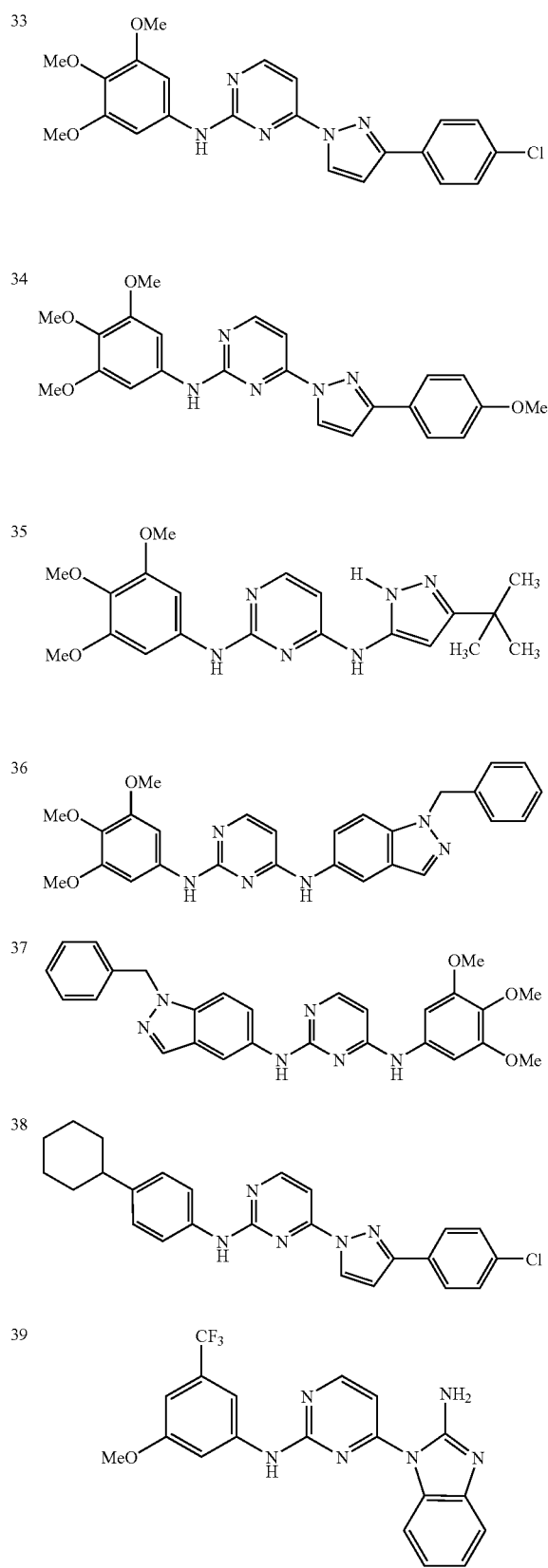
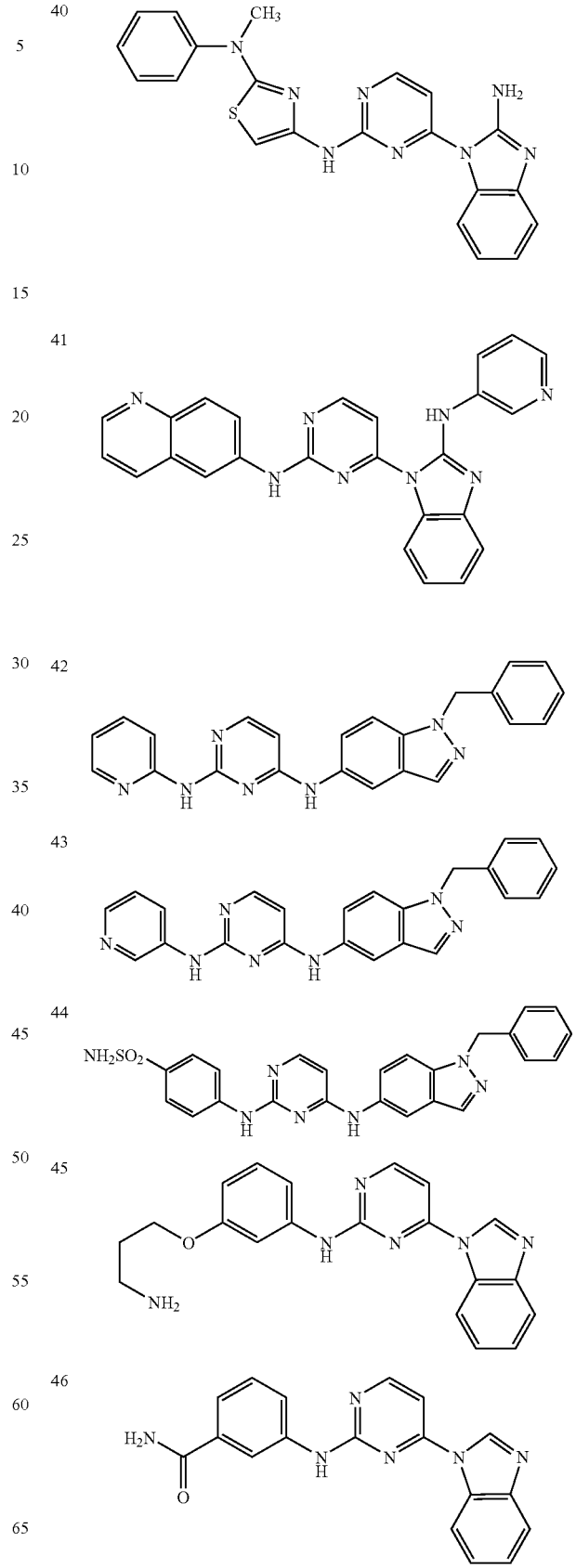

TABLE 1-continued
| 47 | 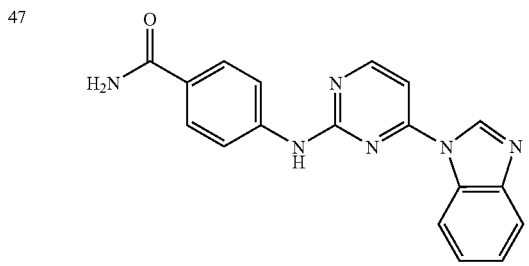 |
| --- | --- |
| 48 | 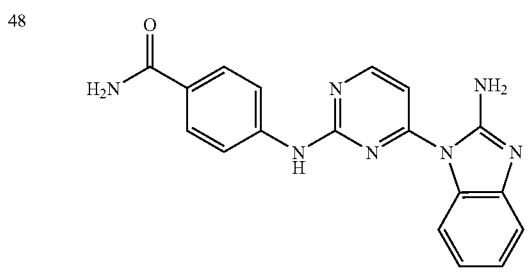 |
| 49 | 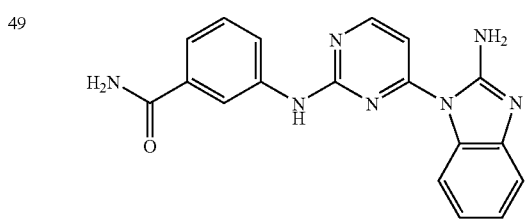 |
| 50 | 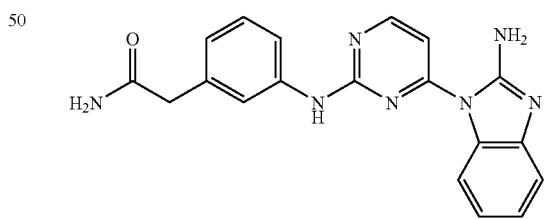 |
| 51 | 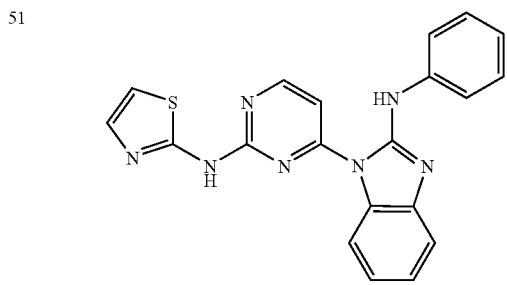 |
| 52 | 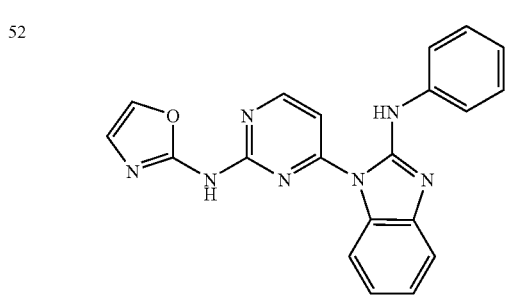 |
TABLE 1-continued
| 53 | 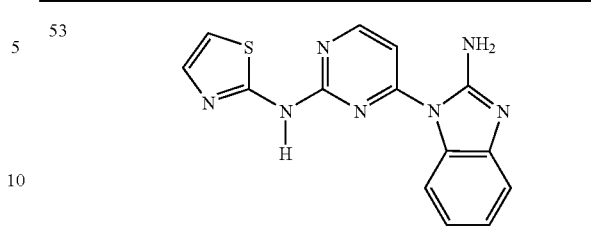 |
| --- | --- |
| 54 | 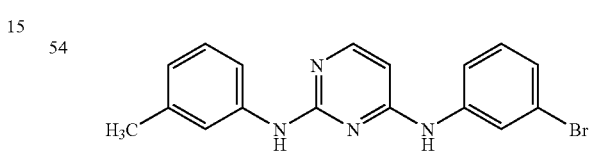 |
| 55 | 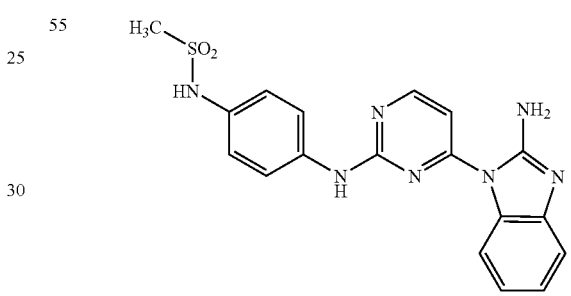 |
| 56 | 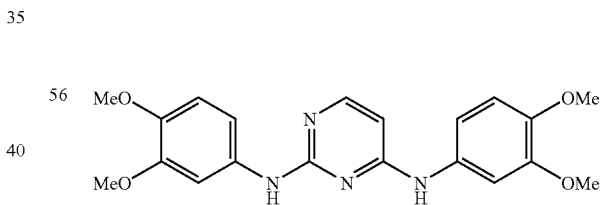 |
| 57 | 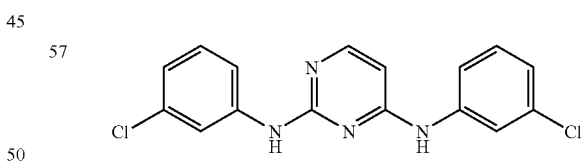 |
| 58 | 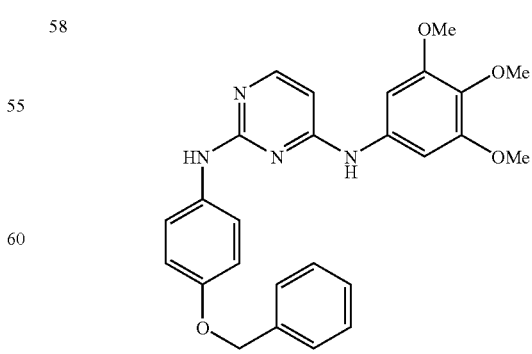 |

TABLE 1-continued

59

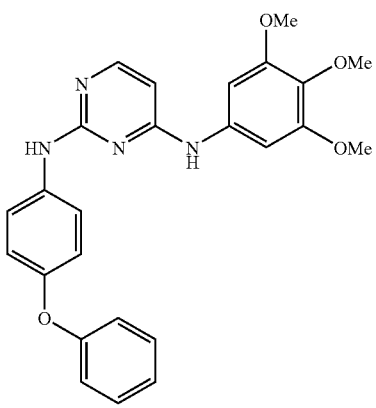

60

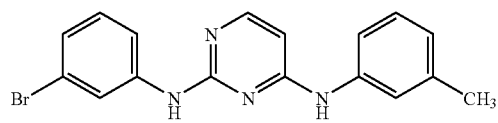

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a mammal or for use in affinity chromatography applications). Typically, such compounds are stable at a temperature of 40° C. or less, in the absence of excessive moisture for at least one week.

As used herein, the compounds of this invention, including the compounds of formulae described herein, are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group which enhances aqueous solubility or active transport through the gut membrane is appended to the structure of formulae described herein.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium), alkaline earth metal (e.g., magnesium), ammonium and N-(alkyl)$_4^+$ salts. This invention also envisions the quaternization of any basic nitrogen-containing groups of the compounds disclosed herein. Water or oil-soluble or dispersible products may be obtained by such quaternization.

The compounds of this invention may be synthesized using conventional techniques. Advantageously, these compounds are conveniently synthesized from readily available starting materials. In general, the compounds of the formulae described herein are conveniently obtained via methods illustrated in General Synthetic Schemes I-VIII and the Examples herein. These general schemes are also exemplified by the specific methods described in the Examples section below. General Synthetic Schemes I-VIII and the examples utilize general chemical group descriptors (e.g., X, $R^3$, $R^5$) that are meant to be representative of any group suitable for synthesis of the compounds delineated herein. Such groups are exemplified by and include, but are not limited to, those defined in the definitions of the groups designated $R^1$, $R^2$, $R^3$, $R^4$, $R^5$, $R^8$, $R^{12}$, $R^{16}$, $R^{17}$, and $R^{20}$, for example, in the formulae herein. Cited references are incorporated by reference in their entirety.

Thus, one embodiment relates to a method of making a compound of the formulae described herein, comprising synthesizing any one or more intermediates illustrated in the synthetic schemes herein and then converting that intermediate(s) to a compound of the formulae described herein. Another embodiment relates to a method of making a compound of the formulae described herein, comprising synthesizing any one or more intermediates illustrated in the examples herein and then converting that intermediate(s) to a compound of the formulae described herein. Another embodiment relates to a method of making a compound of the formulae described herein, comprising synthesizing any one or more intermediates illustrated in the synthetic schemes herein and then converting that intermediate(s) to a compound of the formulae described herein utilizing one or more of the chemical reactions described in the synthetic schemes or examples herein. Nucleophilic agents are known in the art and are described in the chemical texts and treatises referred to herein. The chemicals used in the aforementioned methods may include, for example, solvents, reagents, catalysts, protecting group and deprotecting group reagents and the like. The methods described above may also additionally comprise steps, either before or after the steps described specifically herein, to add or remove suitable protecting groups in order to ultimately allow synthesis of the compound of the formulae described herein.

General Synthetic Scheme I
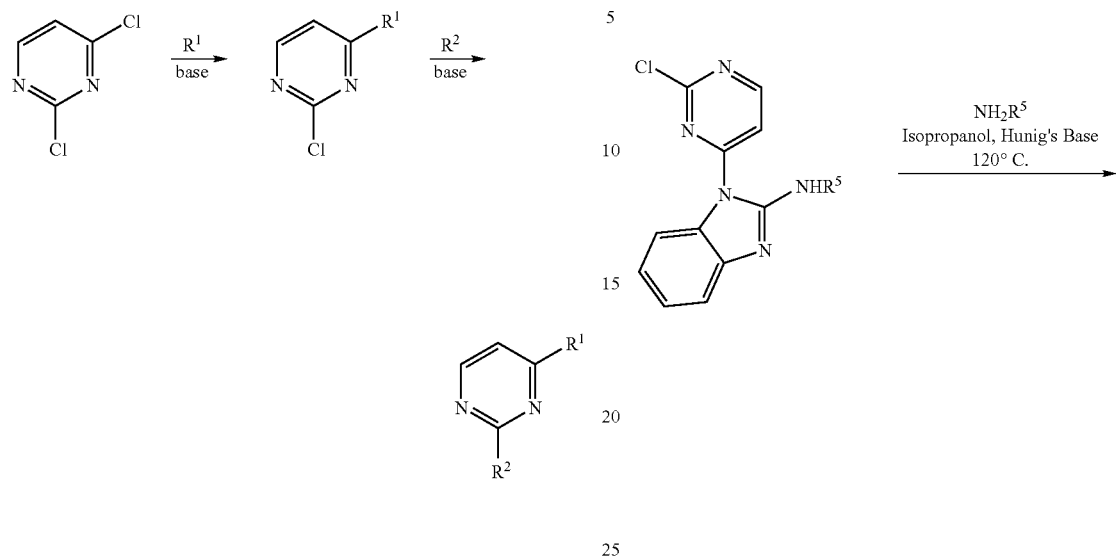
General Synthetic Scheme II
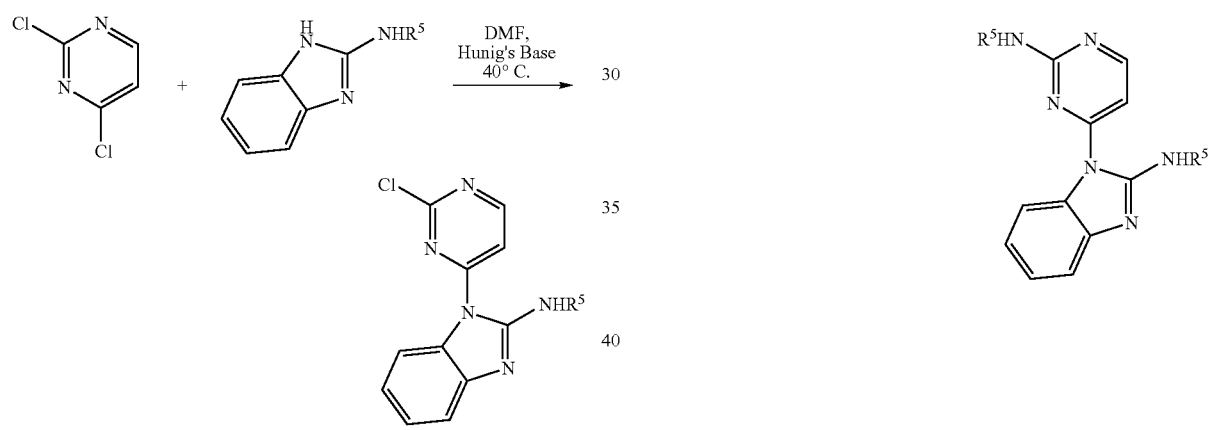
General Synthetic Scheme III
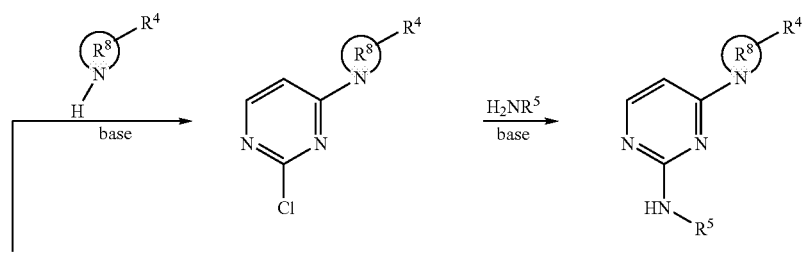

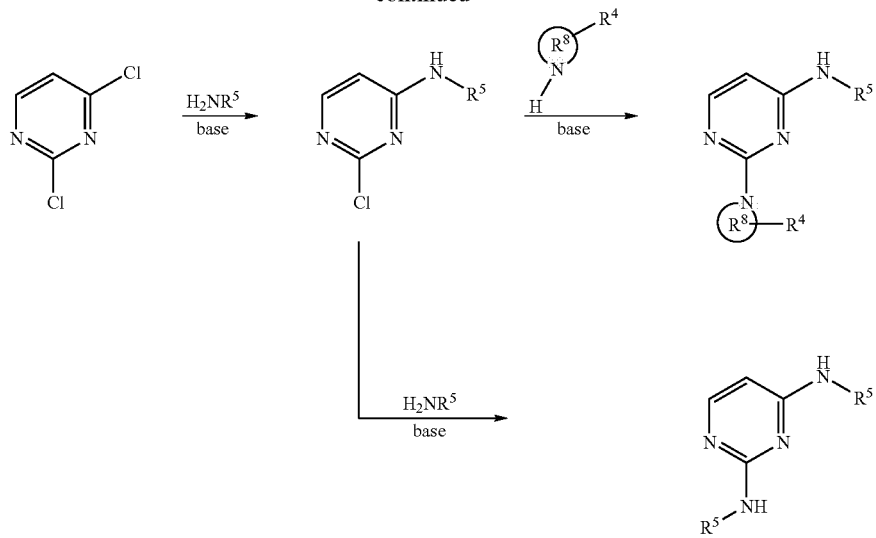
General Synthetic Scheme IV
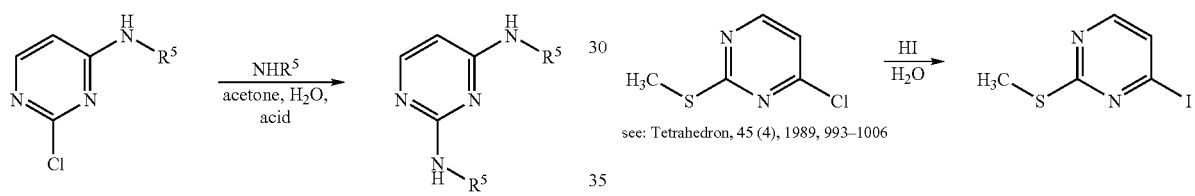
General Synthetic Scheme V
see: Tetrahedron, 45 (4), 1989, 993–1006
General Synthetic Scheme VI
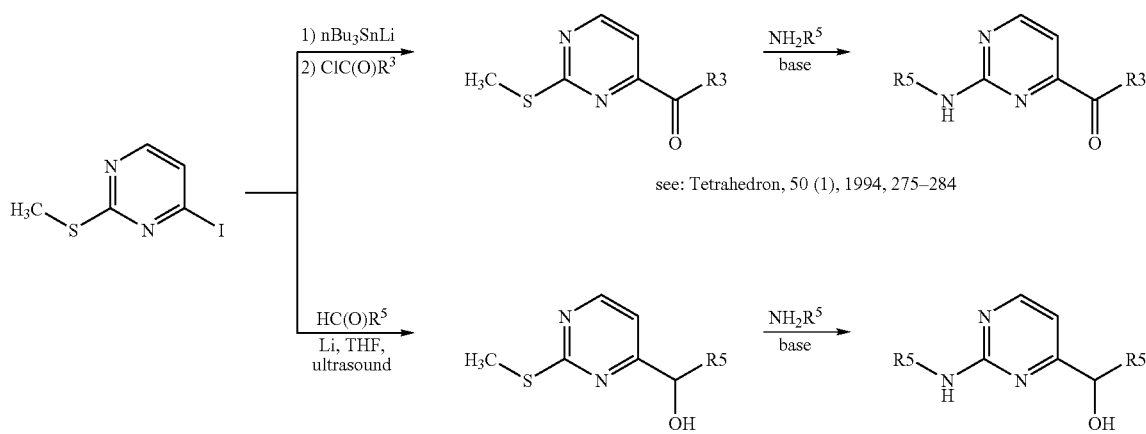
see: Tetrahedron, 50 (1), 1994, 275–284
see: Tetrahedron, 56 (23), 2000, 3709–3716

General Synthetic Scheme VII

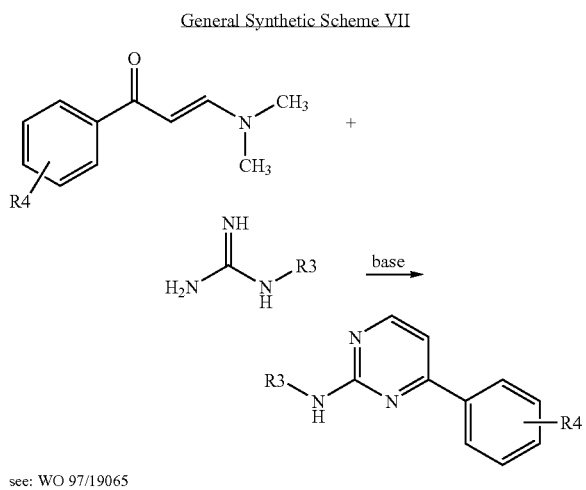

see: WO 97/19065

General Synthetic Scheme VIII

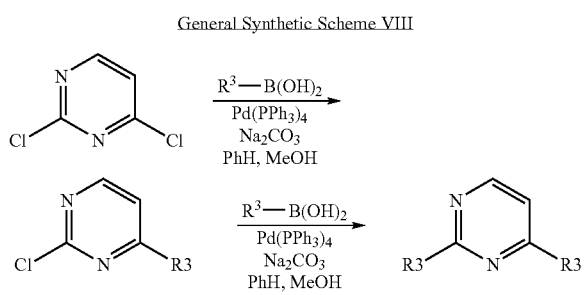

see: Heterocycles, 53 (7), 2000, 1489–1498

In General Synthetic Scheme I, commercially available dichloropyrimidine is sequentially treated, in the presence of base, with nucleophilic forms of $R^1$ and then $R^2$ to provide compounds of the invention. Appropriate nucleophiles (e.g., HNRR, HSR, HOR, or their anion equivalents, carbon anions, etc.) are known in the art.

In a similar fashion, this concept is illustrated in General Synthetic Scheme II, wherein a benzimidazolyl derivative is representative of $R^1$ and an amine derivative is representative of $R^2$.

General Synthetic Scheme III illustrates various pathways for the synthesis of various compounds of the invention wherein one of $R^1$ or $R^2$ is a nitrogen attached heterocyclyl or heteroaryl group (represented as an optionally substituted $R^8$).

General Synthetic Scheme IV illustrates an alternate method for converting a leaving group-substituted pyrimidinyl intermediate (e.g., a chloropyrimidine) to a corresponding aminopyrimidine compound using acidic conditions. This alternative may be appropriate in place of any step in a process depicted herein using basic conditions, as determined by one of ordinary skill.

General Synthetic Scheme V illustrates one method for interconversion of a leaving group on a pyrimidine core to an alternate leaving group. Such compounds are useful intermediates for synthesis of compounds of the formulae herein.

General Synthetic Scheme VI illustrates methods for conversion of leaving group substituted pyrimidines to acyl- and alkyl-substituted pyrimidines described herein.

General Synthetic Scheme VII illustrates a general method for synthesis of aryl-substituted pyrimidines described herein.

General Synthetic Scheme VIII illustrates alternate methodology for synthesis of aryl-substituted pyrimidines described herein.

Alternatively, a compound of any of the formulae delineated herein may be synthesized according to any of the processes delineated herein. In the processes delineated herein, the steps may be performed in an alternate order and may be preceded, or followed, by additional protection/deprotection steps as necesssary. The processes may further comprise use of appropriate reaction inert solvents, additional reagents, such as bases (e.g., LDA, diisopropylethylamine, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase, simulated moving bed ("SMB")), extraction, distillation, trituration, reverse phase HPLC and the like. Reactions conditions such as temperature, duration, pressure, and atmosphere (inert gas, ambient) are known in the art and may be adjusted as appropriate for the reaction.

Thus, one embodiment relates to a method of making a compound of the formulae described herein, comprising the step of reacting a mono- or di-leaving group substituted-1, 3-pyrimidine, for example, a 2-,4-dihalosubstituted-1,3-pyrimidine, with nucleophilic agents (e.g., an aniline or amine) in 1 or 2 steps to form the compound of the formulae described herein. Nucleophilic agents are known in the art and are described in the chemical texts and treatises referred to herein. Such agents may have carbon or a heteroatom (e.g, N, O, S) as the nucleophilic atom. The chemicals used in the aforementioned methods may include, for example, solvents, reagents, catalysts, protecting group and deprotecting group reagents and the like. The methods described above may also additionally comprise steps, either before or after steps 1 and 2 described above, to add or remove suitable protecting groups in order to ultimately allow synthesis of the compound of the formulae described herein.

In one embodiment, the invention relates to a process for making a compound of any of the formulae described herein, comprising reacting a pyrimidine of one or more of the formulae:

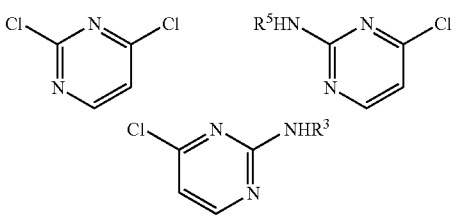

with an appropriate nucleophilic agent or agents, wherein the groups in said formulae are as defined herein.

In one embodiment, the invention relates to a process for making a compound of any of the formulae described herein, comprising reacting a pyrimidine of one or more of the formulae: with an appropriate nucleophilic agent or agents, wherein L is defined as a leaving group and the

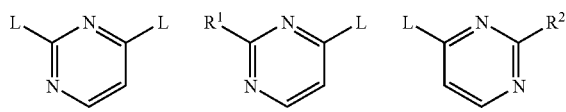

groups in said formulae are as defined herein.

In one embodiment, the invention relates to a process for making a compound of the formula:

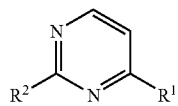

wherein

Each $R^1$ and $R^2$ is independently $R^3$; $R^8$; $NHR^3$; $NHR^5$; $NHR^6$; $NR^5R^5$; $NR^5R^6$; $SR^5$; $SR^6$; $OR^5$; $OR^6$; $C(O)R^3$; heterocyclyl optionally substituted with 1-4 independent $R^4$ on each ring; or C1-C10 alkyl substituted with 1-4 independent $R^4$;

Each $R^3$ is independently aryl; phenyl optionally substituted with 1-4 independent $R^4$; or heteroaryl optionally substituted with 1-4 independent $R^4$ on each ring; and all other substituents are as defined herein, or alternatively a compound of any one of the formulae described herein,; comprising the steps of:

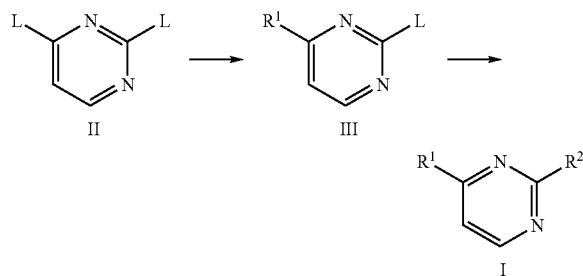

a) reacting a compound of formula (II) wherein each L is independently a leaving group as defined herein, with a nucleophile of formula H—$R^1$ (or salt thereof) to give a compound of formula (III); and b) reacting the compound of formula (III) with a nucleophile of formula H—$R^2$ (or salt thereof) to give a compound of formula (I).

In another embodiment, the process above is carried out by utilizing a nucleophile H—$R^2$ in step (a), then utilizing a nucleophile H—$R^1$ in step (b), as shown:

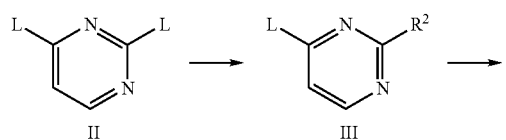

-continued

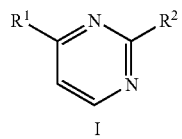

L is defined as a leaving group, and $R^1$ and $R^2$ are as defined herein.

In an alternate embodiment, the above-delineated processes are used to synthesize a compound of any of the formulae delineated herein.

As can be appreciated by the skilled artisan, the above synthetic schemes are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds. Synthetic chemistry transformations and protecting group methodologies (protection and deprotection) useful in synthesizing the inhibitor compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995).

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

The novel compounds of the present invention are excellent ligands for protein kinases, subsequences thereof, and homologous polypeptides. Accordingly, these compounds are capable of targeting and inhibiting kinase enzyme and subsequences thereof. Inhibition can be measured by various methods, including, for example, those methods illustrated in the examples below. The compounds described herein may be used in assays, including radiolabelled, antibody detection, colorimetric, and fluorometric, for the isolation, identification, or structural or functional characterization of enzymes, peptides or polypeptides. Other suitable assays include direct ATP competition displacement assays where no phosphoryl transfer is necessary. Such assays include any assay wherein a nucleoside or nucleotide are cofactors or substrates of the polypeptide of interest, and particularly any assay involving phosphotransfer in which the substrates and or cofactors are ATP, GTP, Mg, Mn, peptides, polypeptides, lipids, or polymeric amino acids.

Pharmaceutical compositions of this invention comprise a compound of the formulae described herein or a pharmaceutically acceptable salt thereof; an additional agent selected from a kinase inhibitory agent (small molecule, polypeptide, antibody, etc.), an immunosuppressant, an anti-cancer agent, an anti-viral agent, antiinflammatory agent, antifungal agent, antibiotic, or an anti-vascular hyperproliferation compound; and any pharmaceutically acceptable carrier, adjuvant or vehicle. Alternate compositions of this invention comprise a compound of the formulae described herein or a pharmaceutically acceptable salt thereof; and a pharmaceutically acceptable carrier, adjuvant or vehicle. Such compositions may optionally comprise one or more additional therapeutic agents, including, for example, kinase inhibitory agents (small molecule, polypeptide, antibody, etc.), immunosuppressants, anti-cancer agents, anti-viral agents, antiinflammatory agents, antifungal agents, antibiotics, or anti-vascular hyperproliferation compounds.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-$\alpha$-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as $\alpha$-, $\beta$-, and $\gamma$-cyclodextrin, or chemically modified derivatives such as hydroxyalkylcyclodextrins, including 2- and 3-hydroxypropyl-$\beta$-cyclodextrins, or other solubilized derivatives may also be advantageously used to enhance delivery of compounds of the formulae described herein.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may comprise formulations utilizing liposome or microencapsulation techniques. Such techniques are known in the art.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, alternatively between about 0.5 and about 75 mg/kg body weight per day of the kinase inhibitory compounds described herein are useful in a monotherapy and/or in combination therapy for the prevention and treatment of kinase mediated disease. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

When the compositions of this invention comprise a combination of a kinase inhibitor of the formulae described herein and one or more additional therapeutic or prophylactic agents, both the kinase inhibitor and the additional agent should be present at dosage levels of between about 10 to 100%, and more preferably between about 10 to 80% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

According to one embodiment, the pharmaceutical compositions of this invention may comprise an additional kinase inhibitory agent. Such additional kinase inhibitory agents are those which may modulate, regulate or otherwise affect kinase enzyme activity. Such effects may lead to modulation of disease pathology and/or symptoms. Kinase inhibitory agents include, for example, small molecules, polypeptides, antibodies (including for example, monoclonals, chimeric, humanized, single chain, immunokines, etc.), and the like. Examples of additional kinase inhibitory small molecule agents include, but are not limited to, SU-6668, SU-5416, ZD-4190, ZD-1839, STI-571, CP-358774, LY-333531 and the like.

According to one embodiment, the pharmaceutical compositions of this invention comprise an additional immunosuppression agent. Examples of additional immunosuppression agents include, but are not limited to, cyclosporin A, FK506, rapamycin, leflunomide, deoxyspergualin, prednisone, azathioprine, mycophenolate mofetil, OKT3, ATAG, interferon and mizoribine.

According to an alternate embodiment, the pharmaceutical compositions of this invention may additionally comprise antibodies (including for example, monoclonals, chimeric, humanized, single chain, immunokines, etc.), cytotoxic or hormonal anti-cancer agents or combinations thereof. Examples of anti-cancer agents include, but are not limited to, cis-platin, actinomycin D, doxorubicin, vincristine, vinblastine, etoposide, amsacrine, mitoxantrone, tenipaside, taxol, taxotere, colchicine, phenothiazines, interferons, thioxantheres, anti-estrogens (e.g., tamoxifen), aromatase inhibitors, anti-androgens, LHRH antagonists, progetins, and GnRH antagonists.

According to another alternate embodiment, the pharmaceutical compositions of this invention may additionally comprise an anti-viral agent. Examples of anti-viral agents include, but are not limited to, Cytovene, Ganciclovir, trisodium phosphonoformate, Ribavirin, d4T, ddI, AZT, amprenavir and acyclovir.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

In an alternate embodiment, this invention provides methods of treating, preventing, or relieving symptoms of disease in a mammal comprising the step of administrating to said mammal any of the pharmaceutical compositions and combinations described above. Preferably, the mammal is a human. If the pharmaceutical composition only comprises the inhibitor of this invention as the active component, such methods may additionally comprise the step of administering to said mammal an additional therapeutic agent, such as an antiinflammatory agent, immunosuppressant, an anti-cancer agent, an anti-viral agent, or an anti-vascular hyperproliferation compound. Such additional agent may be administered to the mammal prior to, concurrently with, or following the administration of the inhibitor composition.

The compounds of this invention may contain one or more asymmetric centers and thus occur as racemates and racemic mixtures, scalemic mixtures, single enantiomers, individual diastereomers and diastereomeric mixtures. All such isomeric forms of these compounds are expressly included in the present invention. The compounds of this invention may also be represented in multiple tautomeric forms, for example, as illustrated below:

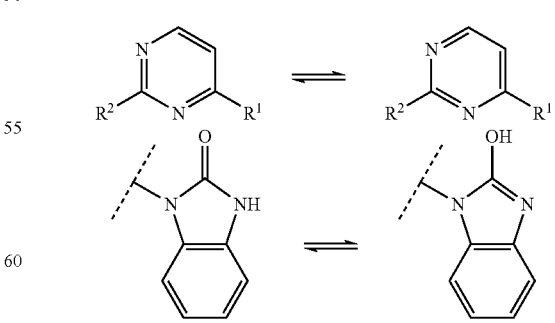

in such instances, the invention expressly includes all tautomeric forms of the compounds described herein. The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom (see below), whereby they are intended to be attached at any available atom that is not already substituted by an atom other than H (hydrogen). For example, a structure drawn as:

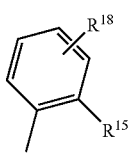

is intended to encompass all of the following structures:

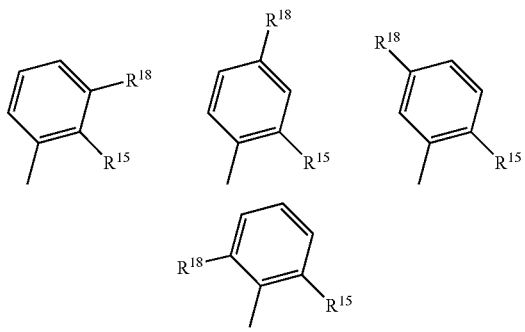

The compounds of this invention may contain heterocyclic ring systems attached to another ring system (e.g., a pyrimidinyl core ring, an $R^8$ substituent as defined herein, or a heteroaryl group). Such heterocyclic ring systems may be attached through a carbon atom or a heteroatom in the ring system. In instances wherein a heterocyclic or heteroaryl ring system is stated to be attached at a heteroatom (e.g., nitrogen atom), this refers to the heterocyclic or heteroaryl ring system being attached to the designated functional group at said nitrogen heteroatom. To illustrate, for example, when an $R^1$ or $R^2$ substituent on a pyrimidinyl core is a heteroaryl defined as being attached at a nitrogen atom, this definition includes, but is not limited to, structures such as those exemplified below:

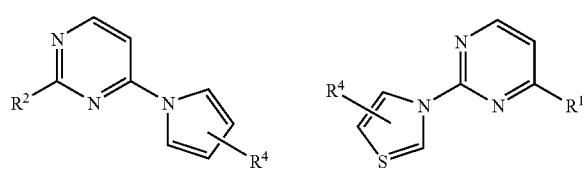

-continued

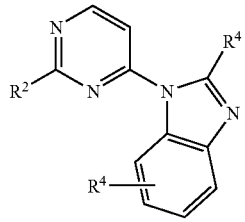

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

In order that the invention described herein may be more readily understood, the following examples are set forth. It should be understood that these examples are for illustrative purposes only and are not to be construed as limiting this invention in any manner. NMR and MS spectra obtained for compounds described in the examples below and those described herein were consistent with that of the compounds of the formulae herein.

Analytical Methods:

Unless otherwise indicated all HPLC analyses are run on a HP-1050 system with an HP Zorbax SB-C18 (5μ) reverse phase column (4.6×150 mm) run at 30° C. with a flow rate of 1.00 ml/minute.

The mobile phase used solvent A (water/0.1% trifluoroacetic acid) and solvent B (acetonitrile/0.1% trifluoroacetic acid) with a 20-minute gradient from 10% to 90% acetonitrile. The gradient is followed by a 2-minute return to 10% acetonitrile and a 3 minute flush.

The peaks of interest eluted on the LC profiles at the times indicated.

LC-MS Method:

1. Samples are run on a HP-1100 MSD system with a HP Zorbax SB-C8 (5, reverse phase column (4.6×50 mm) run at 30° C. with a flow rate of 0.75 ml/minute.
2. The mobile phase used solvent A (water/0.1% acetic acid) and solvent B (acetonitrile/0.1% acetic acid) with a 10-minute gradient from 10% to 90% acetonitrile. The gradient is followed by a 1-minute return to 10% acetonitrile and a 2 minute flush.

Proton NMR Spectra:

Unless otherwise indicated, all $^1$H NMR spectra are run on a Varian series Mercury 300 MHz instrument. All observed protons are reported as parts-per-million (ppm) downfield from Tetramethylsilane (TMS) or other internal reference in the appropriate solvent indicated.

EXAMPLE 1

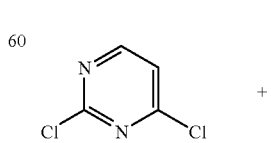

+

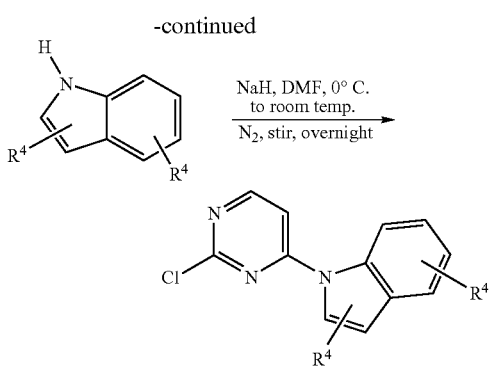

The indole (10 mmole) is dissolved into DMF (20 mL) under nitrogen at room temperature, in a round bottom flask fitted with a magnetic stir bar and rubber septum. This solution is cooled to 0° C. with an ice-water bath. NaH (10 mmole, as the 60% suspension in mineral oil) is then added. Once gas evolution ceases, 2,4-dichloropyrimidine (10 mmole) is added as the solid. The reaction is then left to stir overnight with gradual warming to room temperature. Mass spectral analysis of the crude reaction mixture shows complete reaction. The reaction is quenched with saturated $NH_4Cl_{(aq)}$. This mixture is then diluted with water and extracted with EtOAc (100 mL). The EtOAc extracts are then washed with water and brine, combined, dried over anhydrous $Na_2SO_4$, filtered, and concentrated under reduced pressure. The recovered waxey solid is then purified by flash silica gel column chromatography (5% and 10% EtOAc:Hexane step gradient) giving approximately 35% yield.

EXAMPLE 2

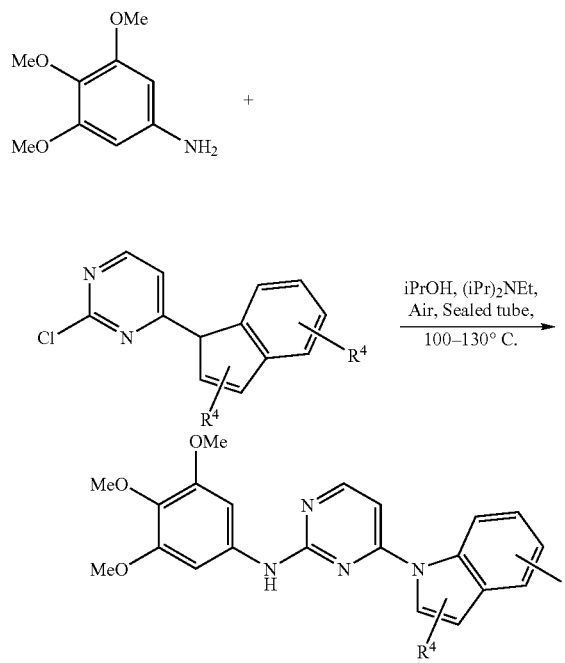

The pyrimidine-indole substrate (0.5 mmol) is suspended into isopropanol (6 mL) under air at room temperature in an open tube. Diisopropylethylamine (0.5 mmol) is added followed by addition of the 3,4,5-trimethoxyaniline (0.5 mmol). The tube is then sealed and heated to 100° C. overnight. The temperature of the reaction is gradually increased to 130° C. over 48 hours. The reaction is quenched by cooling it to room temperature. The solvent is removed under reduced pressure and the recovered solid is partially purified by flash silica gel chromatography (20%, 40%, 60%, 80% EtOAc:Hexane step gradient) giving recovered unreacted pyrimidine-indole substrate (60%) and impure desired product. The product is further purified by applying it to 500 g prep plates and developing one time with a 7:7:7:1 MtBE:$CH_2Cl_2$:Hexane:MeOH eluant, followed by a methanol trituration of the recovered solid, giving an approximate 25% yield of an off-white solid.

EXAMPLE 3

Preparation of 3:

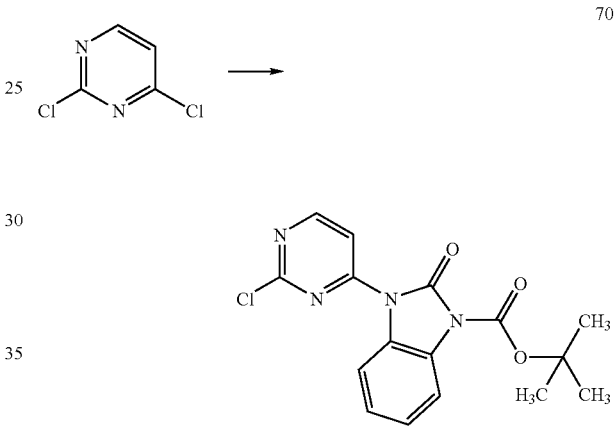

A solution of 0.36 g (2.0 mmol) of 3-t-butylacetate (prepared as in JOC, 1995, 60, 1565-1582) in 10 mL of DMF is cooled to 0° C., and to this is added 0.075 g (2.2 mmol) of NaH (60% dispersion oil). The reaction is stirred for 30 minutes, and then 0.3 g (2.0 mmol) of 2,4-dichloropyrimidine is added as a solid. The ice bath is removed and the reaction is stirred overnight at room temperature. The reaction is quenched with water, and the aqueous is extracted with 3×25 mL EtOAc. The combined organic layers are washed with brine and dried over $MgSO_4$. The crude product is purified by silica chromatography (hexane/ethyl acetate, 4:1) to afford 0.06 g of 70: MS m/z=369 (M+Na).

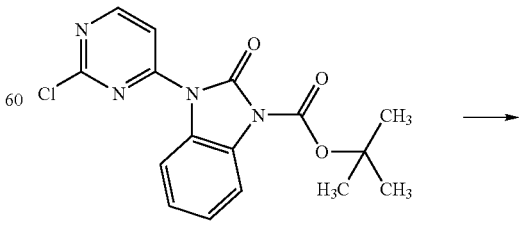

70

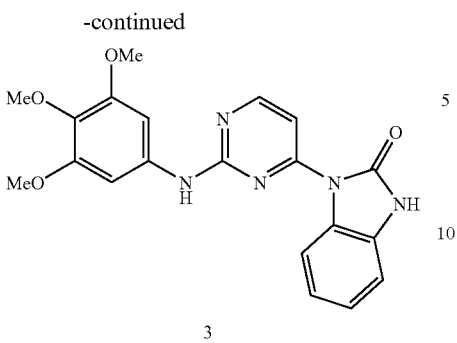

3

To a solution of 0.032 g (0.2 mmol) of 3,4,5-trimethoxyaniline in 5 mL of acetone is added 0.06 g (0.2 mmol) of 70, 5 drops of conc. HCl and 0.5 mL of water. The reaction is heated to reflux and stirred for 12 h. The reaction is then cooled. The resulting white precipitate is filtered, washed with Et$_2$O and water and dried to afford 0.19 g of 3: MS m/z=394 (M+H); HPLC ret time=11.62 minutes.

EXAMPLE 4

Preparation of 11:

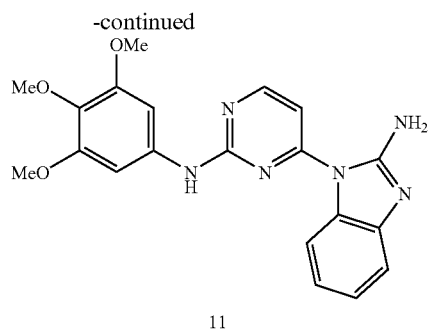

11

Intermediate 71 (264 mg=1.077 mmol) is combined with 197 mg (1.077 mmol) of 3,4,5-trimethoxyaniline and 0.188 ml (1.077 mmol) of diisopropylethylamine in 2 mL isopropyl alcohol. The mixture is heated at about 120° C. overnight. The crude mixture is concentrated down under reduced pressure and purified on 2×1.0 mm silica gel prep plates with 5% methanol/dichloromethane as eluent to yield 81.7 mg (19%) of 11; MS m/z=393 (M+H); HPLC ret time: 10.37 minutes; $^1$H NMR (DMSO-d$_6$) □d 9.8 (s, 1H), 8.3 (m, 2H), 7.7 (s, 2H), 7.0 (m, 3H), 6.7 (m, 2H), 6.6 (m, 1H), 3.7 (s, 6H), 3.5 (s, 3H).

EXAMPLE 5

Preparation of 25:

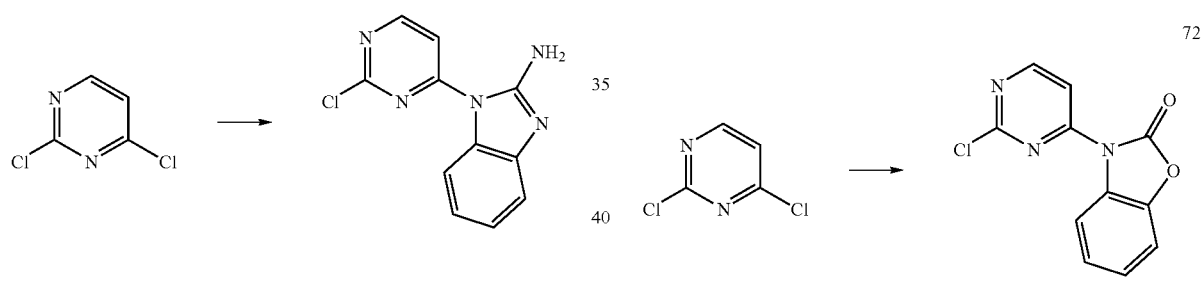

To a solution of 1.738 g (11.665 mmol) of 2,4-dichloropyrimidine in 30 ml DMF at 0° C. is added 2.03 ml (11.665 mmol) of diisopropylethylamine and 1.553 g (11.665 mmol) of 2-aminobenzimidazole. The reaction mixture is stirred at 40° C. for 4 days. The reaction is then cooled to room temperature and diluted into water and ethyl acetate. The layers are separated, and the organic layer is then washed three times with brine, dried over sodium sulfate, and concentrated under reduced pressure to yield 1.837 g of 71.

To a solution of 0.2 g (1.5 mmol) of 2-benzoxazolinone in 5 mL of DMF is added 0.050 g of NaH (60% dispersion oil). The reaction is stirred at room temperature for 30 min, and then a solution of 0.22 g of 2,4-dichloropyrimidine in 1 ml of DMF is added. The reaction is stirred overnight and then quenched with water. The aqueous is extracted with 3×25 ml of EtOAc, and combined organic extracts are washed with brine and dried over MgSO$_4$. The crude product is purified by silica gel chromotagraphy (hexane/EtOAc 4:1) to afford 0.046 g of 72 as an orange solid; MS m/z=248 (M+H).

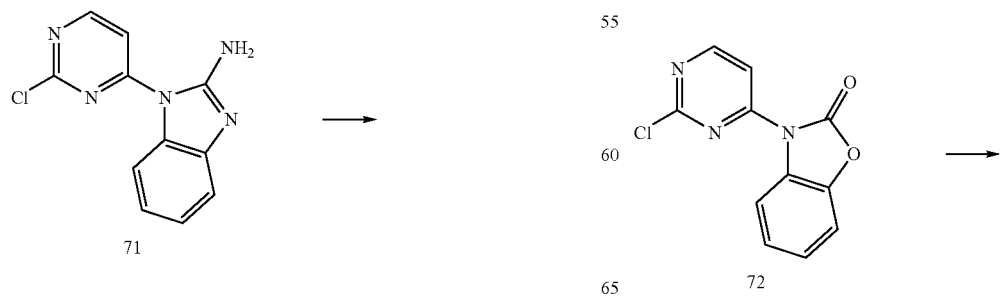

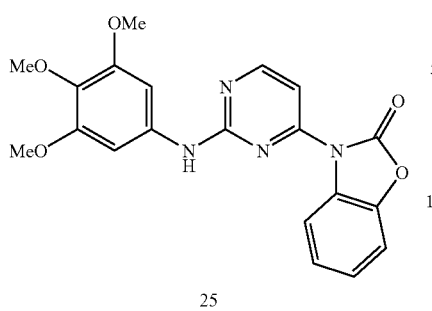

25

To a solution of 0.030 g (0.16 mmol) of 3,4,5-trimethoxyaniline in 10 mL of acetone is added 0.04 g (0.16 mmol) of 72, 3 drops of conc. HCl and 0.5 ml of water. The reaction is heated to reflux and stirred for 14 h. The reaction is then cooled and evaporated. The orange residue is triturated with EtOAc and MeOH, and the resulting white precipitate is filtered, washed with MeOH and dried to afford 0.026 g of 25; MS m/z=395 (M+H).

EXAMPLE 6

Preparation of 31:

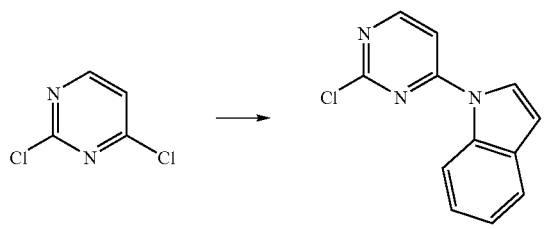

73

Indole (1.15 g, 9.9 mmol) is dissolved into DMF (20 ml) under N$_2$ and cooled to 0° C. NaH (404 mg of a 60% dispersion in mineral oil, 10.1 mmol) is added, which produces a vigorous gas evolution. Once the gas evolution subsides 2,4-dichloropyrimidine (1.5 g, 10.1 mmol) is added and the reaction is allowed to gradually warm to room temperature overnight. The reaction is then quenched with saturated NH$_4$Cl$_{(aq)}$, diluted with water, and extracted three times with ethyl acetate. The ethyl acetate extracts are then washed with brine, combined, dried over anhydrous Na$_2$SO$_4$, filtered and concentrated under reduced pressure. The recovered material is then purified by elution through a 17×2.5 cm column of silica gel (5% and 10% ethyl acetate: hexane step gradient) giving 793 mg (34%) of 73 as a white solid: MS m/z 230=[M+H]$^+$; $^1$H NMR (300 MHz, DMSO-d$_6$) δ 8.72 (d, J=5.9 Hz, 1 H) Hz, 1H), 8.62 (d, J=8.0 Hz, 1H), 8.21 (d, J=3.7 Hz, 1H), 7.95 (d, J=5.9 Hz, 1 H), 7.68 (dd, J=7.7,1.0 Hz, 1 H), 7.39 (m, 1H), 7.28 (t, J=7.7 Hz, 1H), 6.93 (d, J=3.7 Hz, 1 H

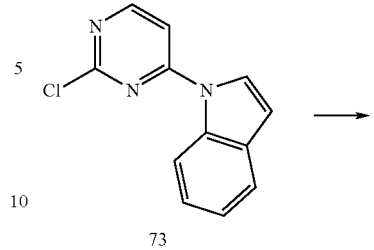

73

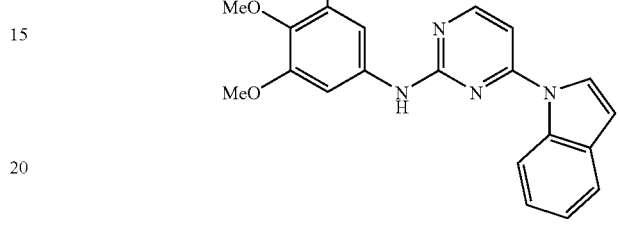

31

2-Chloro-4-(1-indolyl)pyrimidine, 73, (121 mg, 0.53 mmol) is suspended into isopropanol (6 ml), under air at room temperature in a tube. N,N-Diisopropylethylamine (68 mg, 0.53 mmol) is added, followed by the addition of 3,4,5-trimethoxyaniline (97 mg, 0.53 mmol). The tube is then sealed, and the reaction heated to 120° C. for 3 days. The reaction is then cooled to room temperature and concentrated under reduced pressure. The recovered material is then purified by elution through a 17×2.5 cm column of silica gel (20%, 40%, 60% and 80% EtOAc:Hexane step gradient) giving an impure brown solid that is then applied to two 500μ preparative TLC plates and developed one time with 7:7:7:1 MtBE:CH$_2$Cl$_2$:hexane:MeOH. The recovered material is then triturated with methanol giving 50 mg (25%) of 31: MS m/z 377=[M+H]$^+$; $^1$H NMR (300 MHz, DMSO-d$_6$) δ 9.60 (s, 1 H), 876 (br d, J=8.1 Hz, 1 H), 8.49 (d, J=5.7 Hz, 1 H), 8.14 ( d, J=3.4 Hz, 1 H),7.64 (d, J=7.4 Hz, 1 H), 7.24 (m, 2 H),7.17 (s,2 H), 6.82 (d, J=3.7 Hz, 1 H), 5.76 (d, J=1.0 Hz, 1 H), 3.74 (s, 6H), 3.65 (s, 3H); HPLC Rt=11.54 min.

EXAMPLE 7

Preparation of 32:

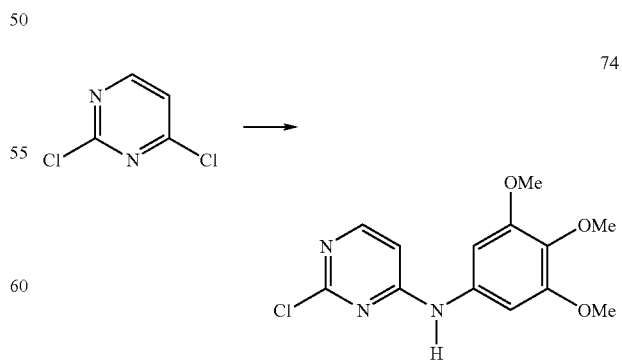

To a solution of 2.0 g (13.4 mmol) of 2,4-dichloropyrimidine in 25 ml of DMF is added 2.4 g (13.4 mmol) of 3,4,5-trimethoxyaniline and 2.6 mL (14.7 mmol) of diisopropylethylamine. The mixture is heated to 50° C. and stirred overnight. The reaction is quenched with water, sat. NH₄Cl and EtOAc, and the resulting precipitate is filtered and dried to afford 2.5 g of 74; MS m/z=296 (M+H); HPLC ret time=8.5 minutes; ¹H NMR (DMSO-d6) δ10.0 (s, 1H), 8.1 (d, 1H), 6.9 (s, 2H), 6.7 (d, 1H), 3.7 (s, 6H), 3.5 (s, 3H).

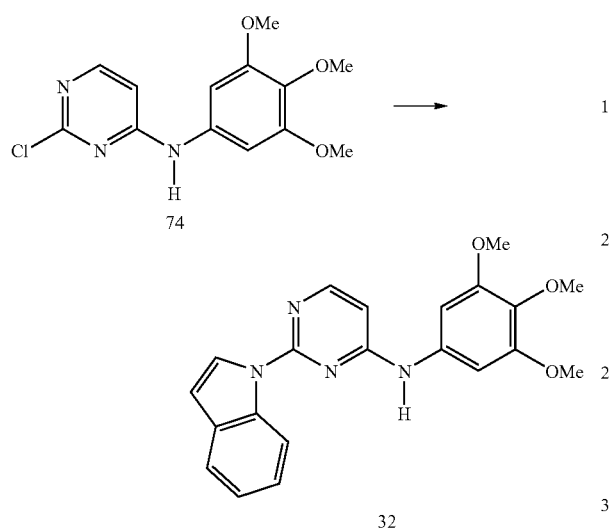

Indole (88 mg, 0.75 mmol) is dissolved into a 1:1 mixture of DMF:THF (5 mL). NaH (60 mg of a 60% dispersion in mineral oil, 1.5 mmol) is added, which produces a vigorous gas evolution. Once the gas evolution subsides, 2-chloro-4-(3',4',5'-trimethoxyanilino)pyrimidine 74 (150 mg, 0.5 mmol is added, the tube is capped, and heated to 100° C. for two weeks. The reaction is then cooled to room temperature and quenched with saturated NH₄Cl$_{(aq)}$. This mixture is then diluted with water and extracted three times with ethyl acetate. The ethyl acetate extracts are then washed with brine, combined, dried over anhydrous Na₂SO₄, filtered and concentrated under reduced pressure. The recovered material is then purified by elution through a 17×2.5 cm column of silica gel (20%, 40%, 60% and 80% EtOAc:Hexane step gradient) giving an impure brown solid that is then applied to two 500μ preperative TLC plates and developed one time with 7:7:7:1 MtBE:CH₂Cl₂:hexane:MeOH giving 20 mg (10%) of 32: MS m/z 377=[M+H]⁺; ¹H NMR (300 MHz, DMSO-d₆) δ 9.78 (s, 1 H), 870 (br d, J=7.7 Hz, 1H), 8.31 (d, J=6.0 Hz, 1H), 8.23 (d, J=3.4 Hz, 1H), 7.62 (dd, J=5.9, 2.5 Hz, 1H), 7.19 (m, 2H), 6.97 (s, 2H), 6.74 (d, J=3.7 Hz, 1H), 6.60 (d, J=6.0 Hz, 1 H), 3.79 (s, 6 H), 3.68 (s, 3H); HPLC Rt=13.72 min.

EXAMPLE 8

Preparation of 33:

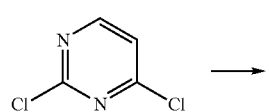

-continued

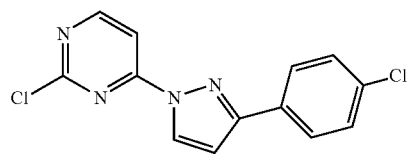

To a mixture of 0.20 g (1.1 mmol) of 3-(4-chlorophenyl) pyrazole in 5 ml of DMF is added 0.042 g of NaH (60% dispersion oil). The reaction is stirred for 30 minutes at room temperature, and then a solution of 0.17 g (1.1 mmol) of 2,4-dichloropyrimidine in 1 ml of DMF is added. The reaction is stirred overnight, and then quenched with water. The aqueous layer is extracted with 3×15 ml EtOAc, and the combined organic layers are washed with brine and dried over MgSO₄. The resulting precipitate is filtered and dried to afford 0.075 g of 75; ¹H NMR (DMSO-d6) δ 8.7 (d, 1H), 8.5 (d, 1H), 7.8 (m, 3H), 7.3 (m, 2H), 7.05 (d, 1H).

To a solution of 0.037 g (0.25 mmol) of 3,4,5-trimethoxyaniline in 7 ml of acetone is added 0.073 g (0.25 mmol) of 75, 3 drops of conc. HCl and 2.0 ml of water. The reaction is heated to reflux and stirred for 24 h. An additional 0.025 g of 3,4,5-trimethoxyaniline is added, along with 2 drops of conc HCl. The reaction is transferred to a sealed tube and is heated to 80° C. for 5 days. The reaction is then cooled and the resulting precipitate is filtered, washed with water and dried to afford 0.011 g of 33; MS m/z=438 (M+H); HPLC ret time=17.2 minutes; ¹H NMR (DMSO-d6) δ 9.6 (s, 1H), 8.4 (m, 2H), 7.8 (m, 2H), 7.4 (m, 2H), 7.2 (t, 1H), 7.05 (m, 1H), 7.0 (d, 2H) 3.7 (s, 6H) 3.5 (s, 3H).

EXAMPLE 9

Preparation of 34:

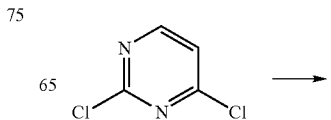

-continued

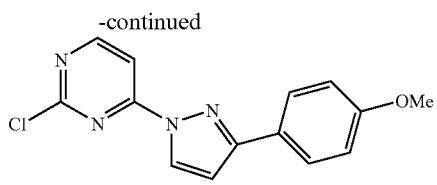

To a mixture of 0.20 g (1.1 mmol) of 3-(4-methoxyphenyl)pyrazole in 5 ml of DMF is added 0.042 g of NaH (60% dispersion oil). The reaction is stirred for 30 minutes at room temperature, and then a solution of 0.17 g (1.1 mmol) of 2,4-dichloropyrimidine in 1 ml of DMF is added. The reaction is stirred overnight, and then quenched with water. The aqueous layer is extracted with 3×15 mL EtOAc, and the combined organic layers are washed with brine and dried over MgSO$_4$. The resulting precipitate is filtered and dried to afford 0.13 g of 76; $^1$H NMR (DMSO-d6) d 8.6 (t, 1H), 8.5 (m, 1H), 7.7 (m, 3H), 7.0 (t, 1H), 6.9 (m, 2H), 3.6 (s, 3H).

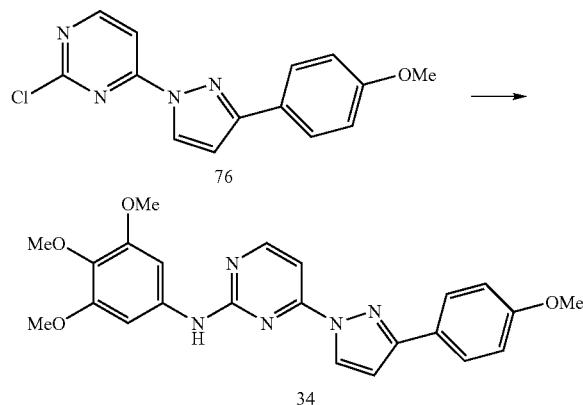

To a solution of 0.097 g (0.65 mmol) of 3,4,5-trimethoxyaniline in 15 mL of acetone is added 0.124 g (0.4 mmol) of 76, 5 drops of conc. HCl and 2.0 ml of water. The reaction is heated to 120° C. in a sealed tube for 18 h. The reaction is then cooled and the resulting precipitate is filtered, washed with water and dried to afford 0.031 g of 34; MS m/z=434 (M+H); HPLC ret time=14.9 minutes; $^1$H NMR (DMSO-d6) δ 9.5 (s, 1H), 8.4 (d, 2H), 7.7 (m, 2H), 7.1 (m, 1H), 7.0 (d, 2H), 6.9 (s, 1H), 6.8 (m, 2H), 3.5 (bs, 12H).

EXAMPLE 10

Preparation of 35:

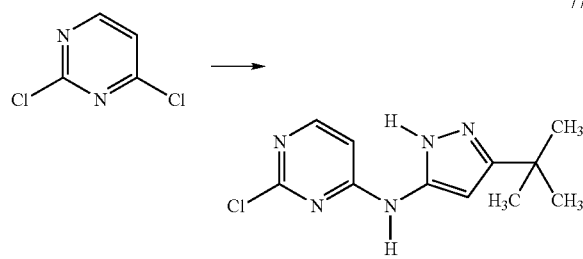

To a solution of 0.20 g (1.3 mmol) of 2,4-dichloropyrimidine in 5 mL of iPrOH is added 0.19 g (1.3 mmol) of 3-amino-5-t-butylpyrazole and 0.25 ml (1.5 mmol) of diisopropylethylamine. The reaction is heated to reflux and is stirred for 10 h. The reaction is cooled and evaporated. The crude residue is purified by silica gel chromatography (5% MeOH/CH$_2$Cl$_2$) to afford 0.25 g of 77.

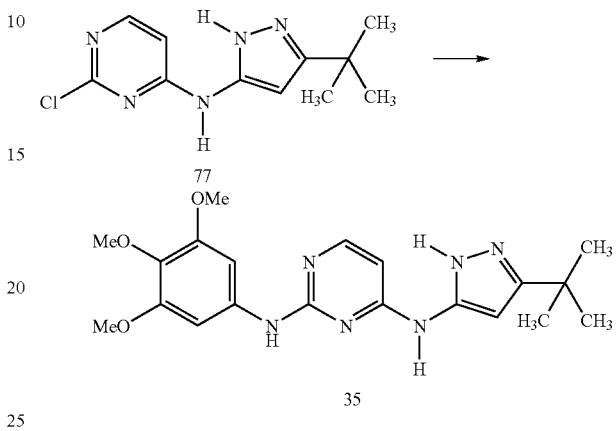

To a solution of 0.25 g (1.0 mmol) of 77 in 15 mL of acetone is added 0.182 g (1.0 mmol) of 3,4,5-trimethoxyaniline, 3 drops of conc. HCl and 2.0 ml of water. The reaction is heated to reflux for 18 h. The reaction is then cooled and the acetone is evaporated in vacuo. The aqueous residue is extracted with EtOAc, and the organic layer is washed with brine and dried over MgSO$_4$. The crude product is purified by silica gel chromatography (5% MeOH/CH$_2$Cl$_2$) to afford 0.29 g of 35: MS m/z=399 (M+H); HPLC ret time=9.3 minutes; $^1$H NMR (DMSO-d6) δ 11.8 (s, 1H), 9.3 (s, 1H), 8.7 (s, 1H), 7.8 (d, 1H), 6.9 (s, 2H), 6.3 (s, 1H), 6.1 (s, 1H), 3.6 (s, 6H), 3.4 (s 3H).

EXAMPLE 11

Preparation of 36:

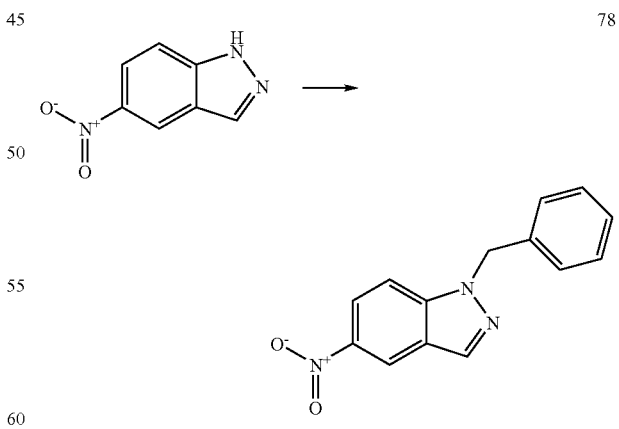

To a solution of 10 g (61.3 mmol) of 5-nitroindazole in 100 ml of DMF is added 12.7 g (91.9 mmol) of K$_2$CO$_3$ and 7.29 mL (61.3 mmol) of PhCH$_2$Br. The resulting mixture is stirred at RT for 3.5 days, and then poured into 400 ml of water. The resulting slurry is filtered, rinsed once with water and dried in vacuo giving a beige solid. A 2.5 g portion of this crude material is purified by chromatography (SiO$_2$, elution with 1:2 EtOAc-hexanes) giving 906.4 mg of 78.

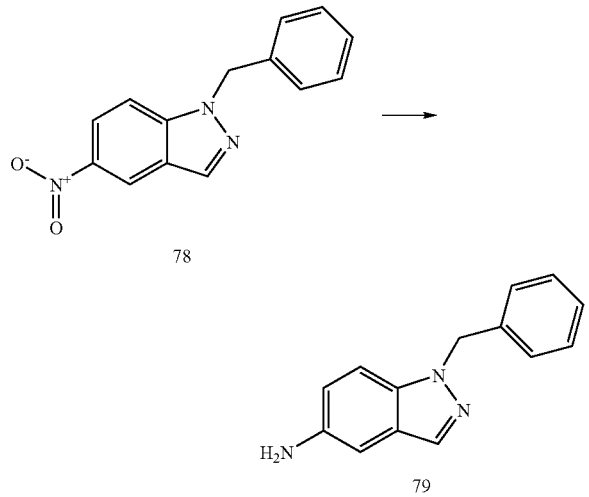

To 906.4 mg (3.58 mmol) of 78 in 20 mL of MeOH and 5 mL of EtOAc at RT is added a slurry of 150 mg of 10% Pd—C in 5 mL of MeOH. The resulting slurry is then stirred under a balloon of H$_2$ for 1.2 h, and filtered through Celite®, rinsing with MeOH and EtOAc. Concentration of the filtrate gives 790.3 mg (98.9%) of 79 as a pinkish solid: MS m/z=224 [M+H]$^+$.

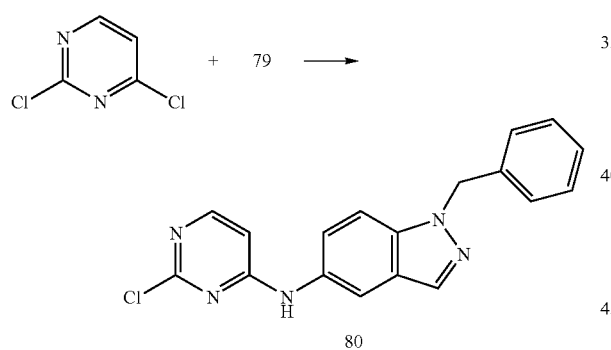

To a solution of 0.056 g (0.37 mmol) of 2,4-dichloropyrimidine in 10 ml of isopropanol is added 0.084 g (0.37 mmol) of 79 and 0.07 ml of diisopropylethylamine (0.41 mmol). The reaction is heated to reflux and is stirred overnight. The organics are then removed in vacuo, and the crude product is purified by silica chromatography (5% MeOH/CH$_2$Cl$_2$) to afford 0.12 g of 80.

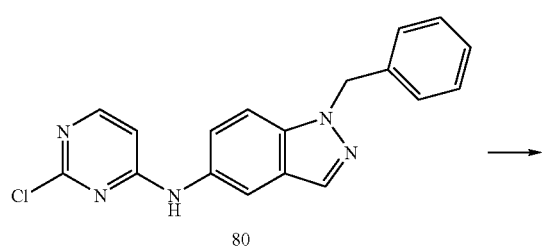

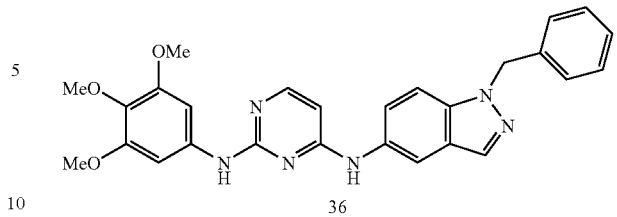

To a solution of 0.12 g (0.36 mmol) of 80 in 10 mL of acetone is added 0.066 g (0.036 mmol) of 3,4,5-trimethoxyaniline, 3 drops of conc. HCl and 1 mL of H$_2$O. The mixture is brought to reflux and is stirred overnight. The reaction is cooled and the acetone is evaporated. The resulting oil is partitioned between EtOAc and water. The organic extracts are washed with brine and sat. NaHCO$_3$ and dried over MgSO$_4$. The crude product is purified by silica chromatography (5% MeOH/CH$_2$Cl$_2$) to afford 0.086 g of 36: MS m/z=483 (M+H); HPLC ret time=11.03 minutes; $^1$H NMR (DMSO-d6) δ 9.1 (s, 1H), 8.7 (s, 1H), 8.05 (s, 1H), 7.7 (m, 2H), 7.4 (d, 1H), 7.0 (m, 4H), 6.9 (s, 1H), 6.7 (d, 1H), 5.95 (d, 1H), 5.4 (s, 2H), 3.4 (bs, 9H).

EXAMPLE 12

Preparation of 37:

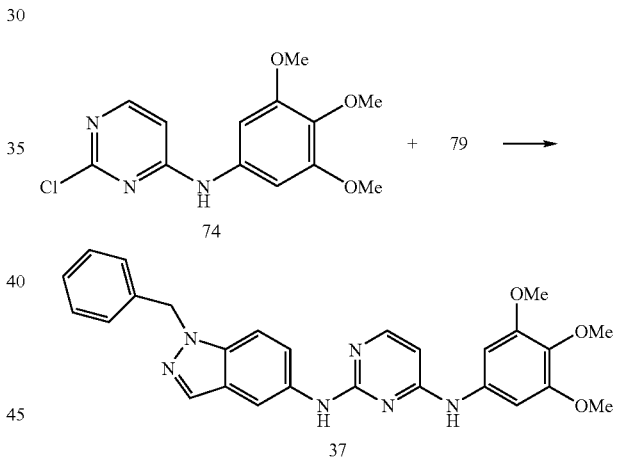

To a solution of 0.071 g (0.24 mmol) of 74 in 10 mL of acetone is added 0.054 g (0.24 mmol) of 79, 3 drops of HCl and 2 mL of H$_2$O. The reaction is heated to reflux and is stirred for 30 h. The reaction is then evaporated, and the resulting oil is partitioned between EtOAc and sat. NaHCO$_3$. The organic extracts are then washed with water, brine and dried over MgSO$_4$. The crude product is purified by silica chromatography (5% MeOH/CH$_2$Cl$_2$) to afford 0.053 g of 37: MS m/z=483 (M+H); HPLC ret time=11.4 minutes; $^1$H NMR (DMSO-d6) δ 9.05 (s, 1H), 8.9 (s, 1H), 8.03 (s, 1H), 7.79 (m, 1H), 7.7 (d, 1H), 7.3 (d, 2H), 7.1 (m, 2H), 7.0 (d, 3H), 6.7 (s, 2H), 5.95 (d, 1H), 5.4 (s, 2H), 3.4 (bs, 9H).

EXAMPLE 13

Preparation of 54:

Compound 54 was prepared essentially by the method described in WO 97/19065 using the appropriate aniline reagents.

HPLC ret time=12.48 minutes; ¹H NMR (DMSO-d6) δ 9.31 (s, 1H), 9.0 (s, 1H), 7.9 (m, 1H), 7.75 (s, 1H), 7.55 (d, 1H), 7.32 (s, 2H), 7.07 (m, 1H), 7.0 (d, 2H), 6.6 (d, 1H), 6.0 (d, 1H). 2.07 (s, 3H).

EXAMPLE 14

Preparation of 56:
Compound 56 was prepared essentially by the method described in WO 97/19065 using the appropriate aniline reagents.
MS m/z=383 (M+H); ¹H NMR (DMSO-d6) δ 9.05 (s, 1H), 8.8 (s, 1H), 7.9 (d, 1H), 7.5 (s, 1H), 7.15 (m, 2H), 6.85 (d, 1H), 6.75 (d, 1H), 6.05 (d, 1H), 3.7 (2, 3H), 3.67 (s, 3H), 3.62 (s, 3H), 3.58 (s, 3H).

EXAMPLE 15

Preparation of 57:
Compound 57 was prepared essentially by the method described in WO 97/19065 using the appropriate aniline reagents.
MS m/z=331 (M+H); ¹H NMR (DMSO-d6) δ 10.9 (s, 1H), 10.53 (s, 1H), 8.0 (d, 1H) 7.72 (s, 1H), 7.65 (s, 1H), 7.52 (d, 1H), 7.39 (m, 3H), 7.19 (m, 2H), 6.48 (d, 1H).

EXAMPLE 16

Preparation of 58:
Compound 58 was prepared essentially by the method described in WO 97/19065 using the appropriate aniline reagents.
HPLC ret time=12.70 minutes; ¹H NMR (DMSO-d6) δ 9.12 (s, 1H), 8.83 (s, 1H), 7.9 (d, 1H), 7.50 (d, 1H), 7.37 (m, 5H), 7.85 (m, 3H), 7.81 (s, 1H), 6.1 (d, 1H), 5.0 (s, 2H), 3.65 (s, 2H), 3.65 (s, 6H), 3.58 (s, 3H).

EXAMPLE 17

Preparation of 59:
Compound 59 was prepared essentially by the method described in WO 97/19065 using the appropriate aniline reagents.
¹H NMR (DMSO-d6) δ 9.2 (s, 1H), 9.11 (s, 1H), 7.92 (d, 1H), 6.68 (d, 2H), 7.3 (t, 2H), 7.04 (t, 1H), 6.9 (m, 6H), 6.14 (d, 1H), 3.65 (s, 6H), 3.56 (s, 3H).

EXAMPLE 18

Preparation of 60:
Compound 60 was prepared essentially by the method described in WO 97/19065 using the appropriate aniline reagents.
HPLC ret time=12.63 minutes; ¹H NMR (DMSO-d6) δ 9.14 (s, 2H), 7.85 (m, 2H), 7.5 (d, 1H), 733 (d, 1H), 7.23 (s, 1H), 7.0 (m, 2H), 6.85 (d, 1H), 6.63 (d, 1H), 6.09 (d, 1H), 2.1 (s, 3H).

EXAMPLE 19

The inhibitor compounds described herein are screened in the following manner. Kinases suitable for use in the following protocol to determine kinase activity of the compounds described herein include, but are not limited to: Lck, Lyn, Src, Fyn, Syk, Zap-70, Itk, Tec, Btk, EGFR, ErbB2, Kdr, Flt-1, Flt-3, Tek, c-Met, InsR, and AKT.

Kinases are expressed as either kinase domains or full-length constructs fused to glutathione S-transferase (GST) or polyHistidine tagged fusion proteins in either *E. coli* or Baculovirus-High Five expression systems. They are purified to near homogeneity by affinity chromatography essentially as previously described (Lehr et al., 1996; Gish et al., 1995). In some instances, kinases are co-expressed or mixed with purified or partially purified regulatory polypeptides prior to measurement of activity.

Kinase activity and inhibition are measured essentially by established protocols (Braunwalder et al., 1996). Briefly, The transfer of $^{33}PO_4$ from ATP to the synthetic substrates poly(Glu, Tyr) 4:1 or poly(Arg, Ser) 3:1 attached to the bioactive surface of microtiter plates serves as the basis to evaluate enzyme activity. After an incubation period, the amount of phosphate transferred is measured by first washing the plate with 0.5% phosphoric acid, adding liquid scintillant, and then counting in a liquid scintillation detector. The $IC_{50}$ is determined by the concentration of compound that causes a 50% reduction in the amount of $^{33}P$ incorporated onto the substrate bound to the plate.

Other similar methods whereby phosphate is transferred to peptide or polypeptide substrate containing tyrosine, serine, threonine, or histidine, either alone, in combination, or in combination with other amino acids, in solution or immobilized (i.e., solid phase) are also useful. For example, transfer of phosphate to a peptide or polypeptide can also be detected using scintillation proximity (Wu et al., 2000), ELISA (Cleaveland et al., 1990), Fluorescence Polarization (Seethala and Menzel, 1998), and homogeneous time-resolved fluorescence (HTRF, Kolb et al., 1998). Alternatively, kinase activity can be measured using antibody-based methods whereby an antibody or polypeptide is used as a reagent to detect phosphorylated target polypeptide. The compounds of the invention described herein are potent and selective kinase inhibitors as demonstrated by representative compounds described herein that inhibit kinases with $IC_{50}$ values at between about 10 nM and about 5 μM or greater. Representative results are summarized in the tables below.

REFERENCES

Braunwalder A F, Yarwood D R, Hall T, Missbach M, Lipson K E, Sills M A. (1996). A solid-phase assay for the determination of protein tyrosine kinase activity of c-src using scintillating microtitration plates. *Anal. Biochem.* 234(1):23-26.

Cleaveland J S, Kiener P A, Hammond D J, Schacter B Z. (1990). A microtiter-based assay for the detection of protein tyrosine kinase activity. *Anal Biochem.* 190(2): 249-53.

Gish G, McGlone M L, Pawson T, Adams J A. (1995). Bacterial expression, purification and preliminary kinetic description of the kinase domain of v-fps. *Protein Eng.* 8(6):609-614.

Kolb, A. J., Kaplita, P. V., Hayes, D. J., Park, Y.-W., Pernell, C., Major, J. S., Mathis, G. (1998). Tyrosine kinase assays adapted to homogeneous time-resolved fluorescence. *Drug Discov. Today.* 3:333-342.

Lehr R V, Ma Y G, Kratz D, Brake P G, Wang S, Faltynek C R, Wang X M, Stevis P E (1996). Production, purification and characterization of non-myristylated human T-cell protein tyrosine kinase in a baculovirus expression system. *Gene* 169(2):27527-9.

Seethala R, Menzel R. (1998). A fluorescence polarization competition immunoassay for tyrosine kinases. *Anal Biochem.* 255(2):257-62.

Wu J J, Yarwood D R, Sills M A, Chaudhuri B, Muller L, Zurini M, Sills M A. (2000). Measurement of cdk4 kinase activity using an affinity peptide-tagging technology. *Comb Chem High Throughput Screen.* 3(1):27-36.

EXAMPLE 20

The cellular activities of the inhibitor compounds described herein may be assessed in a number of assays known to those skilled in the art, some of which are exemplified as described below. Typical sources for cells include, but are not limited to, human bone marrow or peripheral blood lymphocytes, fibroblasts, tumors, immortalized cell lines, in-vitro transformed cell lines, rodent spleen cells, or their equivalents. Tumor cells and transformed cell lines that have been reported as cytokine- and growth factor-dependent cells are available from standard cell banks such as The American Type Culture Collection (Bethesda, Md.). Cells genetically manipulated to express a particular kinase or kinases are also suitable for use in assaying cellular activity and can be made using standard molecular biology methods. These cells are grown in various standard tissue culture media available from suppliers such as GIBCO/BRL (Grand Island, N.Y.) supplemented with fetal bovine serum. Cellular activity may also be measured using bacterial, yeast, or virally infected mammalian cells. Standard inhibitors (or reference compounds) of cellular activities measured in cellular assays, include mycophenolic acid (SIGMA, St. Louis, Mo.), staurosporine (Calbiochem, San Diego, Calif.), wortmannin (Calbiochem), cyclosporine, FK-506, and steroids (e.g., corticosteroids).

The compound(s) are tested for activity in cellular assays of T or B cell activation. For example, the receptor-induced production of cytokines and/or cell proliferation is a useful measure. This assay is performed similarly to techniques described in the literature (1,2), and involves antibody-, antigen-, mitogen-, or antigen presenting cell-mediated crosslinking of the T cell or B cell receptor with or without engagement of co-stimulatory receptors.

The compound(s) are tested for activity in cellular assays of allergic mediator release. For example, the receptor-induced degranulation in mast cells or basophils leading to histamine release and the production of cytokines is a useful measure. This assay is performed similarly to techniques described in the literature (3), and involves signalling via specific cell surface receptors for I, E, or other immunoglobulin (e.g., IgG) following crosslinking of antigen-specific IgE on cells or immune complex binding leading to degranulation and or cytokine production.

The compound(s) are tested for activity in cellular assays of growth factor effects. For example, growth factor receptor-induced signaling in a cell leading to intracellular signaling events such as kinase autophosphorylation, phosphorylation of relevant kinase substrates, phosphorylation of MAP kinases, induction of gene expression, or protein expression. Also, for example, growth factor-induced functional events in cells such as DNA synthesis, proliferation, migration, or apoptosis. These assays are performed similarly to techniques described in the literature (4-7), and involve addition of growth factor to responsive cells followed by monitoring of signaling or functional events.

The compound(s) are tested for activity in cellular assays of lymphokine, chemokine, cytokine, growth factor, or hormone, activation. For example, cytokine-induced intracellular signaling events and/or DNA synthesis and/or cell proliferation and/or cytokine or chemokine production are a useful measure. These assays are performed similarly to techniques described in the literature (8), and involves addition of cytokine to responsive cells followed by monitoring intracellular signaling events and/or cell proliferation and/or cytokine production.

REFERENCES

1. Shuji, K., et al. Activation of p21-CDC42/Rac-activated kinases by CD28 signaling: p21-activated kinase (PAK) and MEK kinase 1 (MEKK1) may mediate the interplay between CD3 and CD28 signals. *J. Immunol.* 160: 4182-4189 (1998).
2. Satterthwaite, A. B., et al., Independent and opposing roles for Btk and Lyn in B cell and myeloid signaling pathways. *J. Exp. Med.* 188: 833-844 (1998).
3. Stephan, V., et al. FcεR1-induced protein tyrosine phosphorylation of pp72 in rat basophilic leukemia cells (RBL-2H3). *J. Biol. Chem.* 267 (8): 5434-5441 (1992).
4. Olayioye, M. A., et al. ErbB-1 and ErbB-2 acquire distinct signaling properties dependent upon their dimerization partner. *Molecular and Cellular Biology.* 18(9): 5042-5051 (1998).
5. Buchdunger, E., et al. Inhibition of the Abl protein-tyrosine kinase in vitro and in vivo by a 2-phenylaminopyrimidine derivative. *Cancer Res.* 56; 101-104 (1996).
6. Yoshida, A. et al., Differential endothelial migration and proliferation to basic fibroblast growth factor and vascular endothelial growth factor. *Growth Factors.* 13:57-64 (1996).
7. Brunet, A., et al., Akt promotes cell survival by phosphorylating and inhibiting a forkhead transcription factor. *Cell.* 96:857-868 (1999).
8. Liu, K. D., et al. Janus kinases in interleukin-2-mediated signaling: JAK1 and JAK3 are differentially regulated by tyrosine phosphorylation. *Current Biology.* 7 (11): 817-826 (1997).

Representative compounds tested under the following example protocols exhibit cellular activities consistent with their observed enzyme inhibition activities.

EXAMPLE 21

Vascular endothelial growth factor (VEGF)-induced Kdr auto-phosphorylation. Human umbilical vein endothelial cells (HUVEC) are plated out in flat-well plates in complete media and allowed to adhere overnight. The cells are then starved in medium containing 0.1% fetal calf serum (FCS), pre-incubated with or without dilutions of compound, then activated for 15 minutes with 50 ng/ml VEGF. The cells are lysed and Kdr is immunoprecipitated using an anti-Kdr antibody. The immunoprecipitated Kdr protein is separated by sodium dodecyl sulfate-polyacrylamide gel electrophoresis (SDS-PAGE) and the level of phosphotyrosine is determined by western blotting with an anti-phosphotyrosine-specific antibody. $IC_{50}$'s are determined by comparing the level of phosphotyrosine found in the presence of compound compared to controls.

EXAMPLE 22

Vascular Endothelial Growth Factor (VEGF)-Induced Extra-Cellular Signal Regulated Kinase (Erk) 1/2-phosphorylation. Human umbilical vein endothelial cells (HUVEC) are plated out in flat-well plates in complete media and allowed to adhere overnight. The cells are then starved in medium containing 0.1% fetal calf serum (FCS), pre-incubated with or without dilutions of compound, then activated for 15 minutes with 50 ng/ml VEGF. The cells are lysed and proteins are separated by SDS-PAGE. The level of phosphotyrosine on Erk1/2 is determined by western blotting with an anti-phospho-Erk1/2-specific antibody. $IC_{50}$'s are determined by comparing the level of phosphotyrosine found in the presence of compound compared to controls.

EXAMPLE 23

Vascular endothelial growth factor (VEGF)-induced proliferation. Human umbilical vein endothelial cells (HUVEC) are plated out in flat-well plates in complete media and allowed to adhere overnight. The cells are then starved in medium containing 0.1% fetal calf serum (FCS), pre-incubated with or without dilutions of compound, then activated for 72 hours with 50 ng/ml VEGF. Proliferation is determined by the level of $^3$H-thymidine incorporation into DNA. $IC_{50}$'s are determined by comparing the level of thymidine incorporation found in the presence of compound compared to controls.

EXAMPLE 24

Growth factor-induced DNA synthesis. A rat fibroblast cell line is plated out in flat-well plates in complete medium and allowed to adhere overnight. The cells are then starved in medium containing 0.1% bovine serum albumin (BSA), pre-incubated with or without dilutions of compound, then activated overnight with 50 ng/ml platelet derived growth factor (PDGF), 1 ng/ml epidermal growth factor (EGF), 3 ng/ml fibroblast growth factor (FGF), or 10 ng/ml insulin-like growth factor-1 (IGF-1). Proliferation is determined by the level of $^3$H-thymidine incorporation into DNA. $IC_{50}$'s are determined by comparing the level of thymidine incorporation found in the presence of compound compared to controls.

EXAMPLE 25

Platelet-derived growth factor (PDGF)-induced PDGF receptor (PDGF-R) auto-phosphorylation. A mouse fibroblast cell line is plated out in flat-well plates in complete medium and allowed to adhere overnight. The cells are then starved in medium containing 0.1% bovine serum albumin (BSA), pre-incubated with or without dilutions of compound, then activated with 50 ng/ml platelet derived growth factor (PDGF) for 5 minutes. The cells are lysed and proteins are separated by SDS-PAGE. The level of phosphotyrosine on PDGF-R is determined by western blotting with an anti-phospho-tyrosine-specific antibody. $IC_{50}$'s are determined by comparing the level of phosphotyrosine found in the presence of compound compared to controls.

EXAMPLE 26

Epidermal growth factor (EGF)-induced EGF receptor (EGF-R) auto-phosphorylation. Human epidermoid carcinoma cells (A431) are plated out in flat-well plates in complete media and allowed to adhere overnight. The cells are then starved in medium containing 0.5% fetal calf serum (FCS), pre-incubated with or without dilutions of compound, then activated for 3 minutes with 50 ng/ml EGF. The cells are lysed and proteins are separated by SDS-PAGE. The level of phosphotyrosine on EGF-R is determined by western blotting with an anti-phospho-EGF-R-specific antibody. $IC_{50}$'s are determined by comparing the level of phosphotyrosine found in the presence of compound compared to controls.

EXAMPLE 27

Heregulin-β1 (HRG)-induced ErbB2 auto-phosphorylation. Human breast carcinoma cells (ZR-75) are plated out in flat-well plates in complete media and allowed to adhere overnight. The cells are then starved in medium containing 0.5% fetal calf serum (FCS), pre-incubated with or without dilutions of compound, then activated for 5 minutes with 50 ng/ml HRG. The cells are lysed and proteins are separated by SDS-PAGE. The level of phosphotyrosine on ErbB2 is determined by western blotting with an anti-phospho-ErbB2-specific antibody. $IC_{50}$'s are determined by comparing the level of phosphotyrosine found in the presence of compound compared to controls.

EXAMPLE 28

Hepatocyte growth factor (HGF) receptor (Met) auto-phosphorylation. Human gastric carcinoma cells (MKN-45), which overexpress and constitutively auto-phosphorylate Met, are plated out in flat-well plates in complete media and allowed to adhere overnight. The cells are then incubated with or without dilutions of compound for 1 hour. The cells are lysed and proteins are separated by SDS-PAGE. The level of phosphotyrosine on Met is determined by western blotting with an anti-phospho-tyrosine-specific antibody. $IC_{50}$'s are determined by comparing the level of phosphotyrosine found in the presence of compound compared to controls.

EXAMPLE 29

Anti-CD3/CD28-induced IL-2 secretion and proliferation. Purified T cells are obtained from human peripheral blood lymphocytes. T cells are pre-incubated incubated with or without dilutions of compound for 30 minutes. The T cells and compounds are then transferred to a plate containing captured anti-CD3-specific antibody. Anti-CD28-specific antibody is then added and the cells are incubated for 20 hours. T cell supernatants are measured for the presence of interleukin-2 by commercially available ELISA. $IC_{50}$'s are determined by comparing the level of IL-2 secretion found in the presence of compound compared to controls. The cells are then pulsed with $^3$H-thymidine and incubated for an additional 24 hours to determine cellular proliferation. $IC_{50}$'s are determined by comparing the level of thymidine incorporation found in the presence of compound compared to controls.

EXAMPLE 30

Anti-CD3-induced T receptor ζ-chain (TCRζ) phosphorylation. The human T cell line, Jurkat, is pre-incubated with or without compounds, then incubated with anti-CD3-specific antibody at 4° C. Cells are washed, then incubated at 4° C. with a secondary anti-immunoglobulin antibody for crosslinking. Cells are activated by transfer to a 37° C. water bath for 1 minute. The cells are lysed and proteins are separated by SDS-PAGE. The level of phosphotyrosine on TCRC is determined by western blotting with an anti-phospho-tyrosine-specific antibody. $IC_{50}$'s are determined by comparing the level of phosphotyrosine found in the presence of compound compared to controls.

The following tables summarize results ($IC_{50}$) of representative compounds of the formulae described herein in assay protocols described in Example 19.

TABLE 2

| Compound number | Akt3-1 | EGFR-1 | ErbB2-1 | ErbB4-1 | FGFR1-1 |
|---|---|---|---|---|---|
| 3  | D  | D | D  | D  | A  |
| 11 | C  | D | ND | ND | ND |
| 25 | D  | D | D  | ND | ND |
| 31 | D  | D | ND | B  | A  |
| 32 | D  | D | ND | ND | ND |
| 33 | D  | D | D  | ND | ND |
| 34 | D  | C | D  | ND | ND |
| 35 | D  | C | D  | C  | C  |
| 36 | D  | A | A  | ND | ND |
| 37 | D  | B | A  | ND | ND |
| 54 | D  | D | D  | ND | ND |
| 56 | D  | D | D  | ND | B  |
| 57 | D  | D | D  | ND | C  |
| 58 | ND | D | ND | ND | ND |
| 59 | ND | C | ND | ND | ND |
| 60 | D  | D | ND | ND | ND |

TABLE 3

| Compound number | Flt1-1 | Fyn-1 | Hck-1 | IGFR-1 | InsR-1 |
|---|---|---|---|---|---|
| 3  | A  | C  | D  | A  | B  |
| 11 | ND | ND | ND | ND | ND |
| 25 | ND | ND | ND | D  | ND |
| 31 | A  | A  | D  | ND | ND |
| 32 | ND | ND | ND | ND | ND |
| 33 | ND | ND | ND | D  | ND |
| 34 | ND | ND | ND | D  | ND |
| 35 | C  | B  | ND | A  | A  |
| 36 | ND | ND | ND | A  | ND |
| 37 | ND | ND | ND | A  | ND |
| 54 | ND | ND | ND | A  | ND |
| 56 | B  | C  | ND | A  | D  |
| 57 | C  | ND | ND | A  | C  |
| 58 | ND | ND | ND | ND | ND |
| 59 | ND | ND | ND | ND | ND |
| 60 | ND | ND | ND | A  | ND |

TABLE 4

| Compound number | Itk-1 | KDR-1 | Lck-1 | Lck-2 | Lyn-1 |
|---|---|---|---|---|---|
| 3  | D  | A | B | B | B  |
| 11 | C  | C | C | B | ND |
| 25 | D  | D | D | D | ND |
| 31 | B  | A | A | A | A  |
| 32 | ND | C | D | D | ND |
| 33 | D  | D | D | D | ND |
| 34 | D  | D | D | D | ND |
| 35 | B  | B | A | A | A  |
| 36 | A  | A | A | A | ND |
| 37 | B  | B | A | A | ND |
| 54 | D  | C | D | D | ND |
| 56 | D  | A | C | A | ND |
| 57 | C  | A | D | A | ND |
| 58 | C  | C | C | A | ND |
| 59 | C  | C | C | A | ND |
| 60 | B  | B | D | A | ND |

TABLE 5

| Compound number | Met-1 | PDGFRB | Ret-1 | Src-1 | Tek-1 | Zap-1 |
|---|---|---|---|---|---|---|
| 3  | B  | A  | A  | C  | C  | B  |
| 11 | C  | ND | ND | ND | D  | D  |
| 25 | D  | D  | ND | ND | D  | D  |
| 31 | B  | A  | ND | A  | C  | D  |
| 32 | D  | ND | ND | ND | D  | D  |
| 33 | D  | D  | ND | ND | ND | C  |
| 34 | D  | D  | ND | ND | ND | C  |
| 35 | A  | B  | B  | A  | ND | D  |
| 36 | B  | A  | ND | ND | ND | C  |
| 37 | B  | A  | ND | ND | ND | D  |
| 54 | D  | C  | ND | ND | ND | ND |
| 56 | D  | A  | B  | B  | ND | D  |
| 57 | B  | C  | A  | ND | ND | D  |
| 58 | C  | ND | ND | ND | ND | ND |
| 59 | C  | ND | ND | ND | ND | ND |
| 60 | C  | B  | ND | ND | ND | ND |

The tables herein utilize the following designations:
A < 1.5 μM
B ≥ 1.5 and < 5.0 μM
C ≥ 5.0 and < 10.0 μM
D ≥ 10.0 μM
ND = Not Determined While we have described a number of embodiments of this invention, it is apparent that our basic examples may be altered to provide other embodiments that utilize the products and processes of this invention. Therefore, it will be appreciated that the scope of this invention is to be defined by the claims rather than by the specific embodiments that have been represented by way of example.

What is claimed is:

1. A compound of the formula:

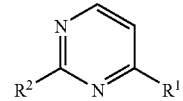

wherein
$R^1$ is of the formula

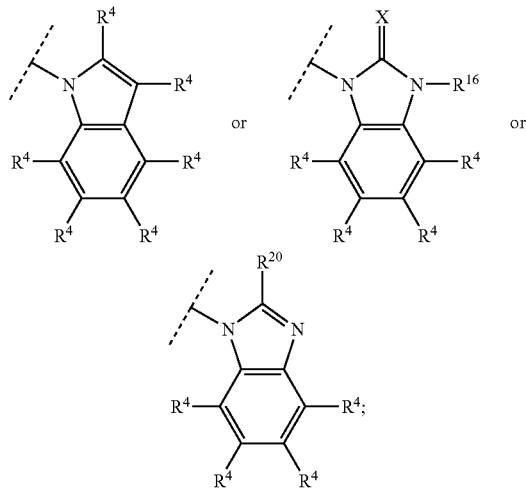

$R^2$ is $NHR^3$;

Each $R^3$ is independently phenyl substituted with 1-4 independent $R^4$; or heteroaryl optionally substituted with 1-4 independent $R^4$ on each ring;

Each n is independently 1 or 2;

Each X is O or S;

Each $R^4$ is independently selected from H, C1-C10 alkyl; C2-C10 alkenyl; C2-C10 alkynyl; C3-C10 cycloalkyl; C4-C10 cycloalkenyl; aryl; $R^8$; halo; haloalkyl; $SR^5$; $OR^5$; $OC(O)R^5$; $NR^5R^5$; $NR^5R^6$; $COOR^5$; $NO_2$; CN; $C(O)R^5$; $C(O)C(O)R^5$; $C(O)NR^5R^5$; $S(O)_nR^5$; $S(O)_n NR^5R^5$; $NR^5C(O)NR^5R^5$; $NR^5 C(O)C(O)R^5$; $NR^5C(O)R^5$; $NR^5(COOR^5)$; $NR^5C(O)R^8$; $NR^5S(O)_n NR^5R^5$; $NR^5S(O)_n R^5$; $NR^5S(O)_n R^8$; $NR^5C(O)C(O)NR^5R^5$; $NR^5C(O)C(O)NR^5R^6$; C1-C10 alkyl substituted with 1-3 independent aryl, $R^7$ or $R^8$; or C2-C10 alkenyl substituted with 1-3 independent aryl, $R^7$ or $R^8$;

Each $R^5$ is independently H; C1-C10 alkyl; C2-C10 alkenyl; C2-C10 alkynyl; C3-C10 cycloalkyl; C4-C10 cycloalkenyl; aryl; $R^9$; haloalkyl; C1-C10 alkyl substituted with 1-3 independent aryl, $R^7$, or $R^9$ groups; C3-C10 cycloalkyl substituted with 1-3 independent aryl, $R^7$ or $R^9$ groups; or C2-C10 alkenyl substituted with 1-3 independent aryl, $R^7$, or $R^9$;

Each $R^6$ is independently $C(O)R^5$, $COOR^5$, $C(O)NR^5R^5$, or $S(O)_n R^5$;

Each $R^7$ is independently halo, $CF_3$, $SR^{10}$, $OR^{10}$, $OC(O)R^{10}$, $NR^{10}R^{10}$, $NR^{10}R^{11}$, $NR^{11}R^{11}$, $COOR^{10}$, $NO_2$, CN, $C(O)R^{10}$, $OC(O)NR^{10}R^{10}$, $C(O)NR^{10}R^{10}$, $N(R^{10})C(O)R^{10}$, $N(R^{10})(COOR^{10})$, $S(O)_n NR^{10}R^{10}$;

Each $R^8$ is independently a 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms independently selected from O, N, or S, which may be saturated or unsaturated, and wherein 0, 1, 2, 3 or 4 atoms of each ring may be substituted by a substituent independently selected from C1-C10 alkyl; C2-C10 alkenyl; C2-C10 alkynyl; C3-C10 cycloalkyl; C4-C10 cycloalkenyl; aryl; $R^9$; halo; sulfur; oxygen; $CF_3$; $SR^5$; $OR^5$; $OC(O)R^5$; $NR^5R^5$; $NR^5R^6$; $NR^6R^6$; $COOR^5$; $NO_2$; CN; $C(O)R^5$; $C(O)NR^5R^5$; $S(O)_n NR^5R^5$; $NR^5C(O)NR^5R^5$; $NR^5C(O)R^9$; $NR^5 S(O)_n NR^5R^5$; $NR^5S(O)_n R^9$; C1-C10 alkyl substituted with 1-3 independent $R^7$, $R^9$ or aryl; or C2-C10 alkenyl substituted with 1-3 independent $R^7$, $R^9$ or aryl;

Each $R^9$ is independently a 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms independently selected from O, N, or S, which may be saturated or unsaturated, and wherein 0, 1, 2 or 3 atoms of each ring may be substituted by a substituent independently selected from C1-C10 alkyl; C2-C10 alkenyl; C2-C10 alkynyl; C3-C10 cycloalkyl; C4-C10 cycloalkenyl; halo; sulfur; oxygen; $CF_3$; $SR^{10}$; $OR^{10}$; $NR^{10}R^{10}$; $NR^{10}R^{11}$; $NR^{11}R^{11}$; $COOR^{10}$; $NO_2$; CN; $S(O)_n R^{10}$; $S(O)_n NR^{10}R^{10}$; $C(O)R^{10}$; or $C(O)NR^{10}R^{10}$;

Each $R^{10}$ is independently H; C1-C10 alkyl; C2-C10 alkenyl; C2-C10 alkynyl; C3-C10 cycloalkyl; C4-C10 cycloalkenyl; haloalkyl; C1-C10 alkyl optionally substituted with 1-3 independent C1-C10 alkyl, C2-C10 alkenyl, C2-C10 alkynyl, C3-C10 cycloalkyl, C4-C10 cycloalkenyl, halo, $CF_3$, $OR^{12}$, $SR^{12}$, $NR^{12}R^{12}$, $COOR^{12}$, $NO_2$, CN, $C(O)R^{12}$, $C(O)NR^{12}R^{12}$, $NR^{12}C(O)R^{12}$, $N(R^{12})(COOR^{12})$, $S(O)_n NR^{12}R^{12}$, or $OC(O)R^{12}$; or phenyl optionally substituted with 1-3 independent C1-C10 alkyl, C2-C10 alkenyl, C2-C10 alkynyl, C3-C10 cycloalkyl, C4-C10 cycloalkenyl, halo, $CF_3$, $OR^{12}$, $SR^{12}$, $NR^{12}R^{12}$, $COOR^{12}$, $NO_2$, CN, $C(O)R^{12}$, $C(O)NR^{12}R^{12}$, $NR^{12}C(O)R^{12}$, $N(R^{12})(COOR^{12})$, $S(O)_n NR^{12}R^{12}$, or $OC(O)R^{12}$;

Each $R^{11}$ is independently $C(O)R^{10}$, $COOR^{10}$, $C(O)NR^{10}R^{10}$ or $S(O)_n R^{10}$;

Each $R^{12}$ is independently H; C1-C10 alkyl; C2-C10 alkenyl; C2-C10 alkynyl; C3-C10 cycloalkyl; C4-C10 cycloalkenyl; C1-C10 alkyl substituted with 1-3 independent C2-C10 alkenyl, C2-C10 alkynyl, C3-C10 cycloalkyl, C4-C10 cycloalkenyl, halo, $CF_3$, $OR^{13}$, $SR^{13}$, $NR^{13}R^{13}$, $COOR^{13}$, $NO_2$, CN, $C(O)R^{13}$, $C(O)NR^{13}R^{13}$, $NR^{13}C(O)R^{13}$, or $OC(O)R^{13}$; or phenyl optionally substituted with 1-3 independent C1-C10 alkyl, C2-C10 alkenyl, C2-C10 alkynyl, C3-C10 cycloalkyl, C4-C10 cycloalkenyl, halo, $CF_3$, $OR^{13}$, $SR^{13}$, $NR^{13}R^{13}$, $COOR^{13}$, $NO_2$, CN, $C(O)R^{13}$, $C(O)NR^{13}R^{13}$, $NR^{13}C(O)R^{13}$, or $O(O)R^{13}$;

Each $R^{13}$ is independently H; C1-C10 alkyl; C2-C10 alkenyl; C2-C10 alkynyl; C3-C10 cycloalkyl; C4-C10 cycloalkenyl; C1-C10 alkyl optionally substituted with halo, $CF_3$, $OR^{14}$, $SR^{14}$, $NR^{14}R^{14}$, $COOR^{14}$, $NO_2$, CN; or phenyl optionally substituted with halo, $CF_3$, $OR^{14}$, $SR^{14}$, $NR^{14}R^{14}$, $COOR^{14}$, $NO_2$, CN;

Each $R^{14}$ is independently H; C1-C10 alkyl; C3-C10 cycloalkyl or phenyl;

Each $R^{16}$ is independently H, C1-C10 alkyl; C2-C10 alkenyl; C2-C10 alkynyl; C3-C10 cycloalkyl; C4-C10 cycloalkenyl; aryl; $R^8$; halo; haloalkyl; $COOR^5$; $C(O)R^5$; $C(O)C(O)R^5$; $C(O)NR^5R^5$; $S(O)_n R^5$; $S(O)_n NR^5R^5$; C1-C10 alkyl substituted with 1-3 independent aryl, $R^7$ or $R^8$; or C2-C10 alkenyl substituted with 1-3 independent aryl, $R^7$ or $R^8$;

Each $R^{20}$ is independently $NR^5R^{16}$; $OR^5$; $SR^5$; or halo;

Each haloalkyl is independently a C1-C10 alkyl substituted with one or more halogen atoms, selected from F, Cl, Br, or I, wherein the number of halogen atoms may not exceed that number that results in a perhaloalkyl group;

Each aryl is independently a 6-carbon monocyclic, 10-carbon bicyclic or 14-carbon tricyclic aromatic ring system optionally substituted with 1-3 independent C1-C10 alkyl; C2-C10 alkenyl; C2-C10 alkynyl; C3-C10 cycloalkyl; C4-C10 cycloalkenyl; $R^9$; halo; haloalkyl; $OR^{10}$; $SR^{10}$; $NR^{10}R^{10}$; $NR^{10}R^{11}$; $COOR^{10}$; $NO_2$; CN; $C(O)R^{10}$; $C(O)C(O)R^{10}$; $C(O)NR^{10}R^{10}$; $N(R^{10})C(O)NR^{10}R^{10}$; $N(R^{10})C(O)R^{10}$; $N(R^{10})S(O)_n R^{10}$; $N(R^{10})(COOR^{10})$; $NR^{10}C(O)C(O)R^{10}$; $NR^{10}C(O)R^9$; $NR^{10}S(O)_n NR^{10}R^{10}$; $NR^{10}S(O)_n R^9$; $NR^{12}C(O)C(O)NR^{12}R^{12}$; $S(O)_n R^{10}$; $S(O)_n NR^{10}R^{10}$; $OC(O)R^{10}$; C1-C10 alkyl substituted with 1-3 independent $R^9$, halo, $CF_3$, $OR^{10}$, $SR^{10}$, $OC(O)R^{10}$, $NR^{11}R^{11}$, $NR^{10}R^{10}$, $NR^{10}R^{11}$, $COOR^{10}$, $NO_2$, CN, $C(O)R^{10}$, $OC(O)NR^{10}R^{10}$, $C(O)NR^{10}R^{10}$, $N(R^{10})C(O)R^{10}$, $N(R^{10})(COOR^{10})$, $S(O)_n NR^{10}R^{10}$; $R^{10}$; or C2-10 alkenyl substituted with 1-3 independent $R^9$, halo, $CF_3$, $OR^{10}$, $SR^{10}$, $OC(O)R^{10}$, $NR^{11}R^{11}$, $NR^{10}R^{10}$, $NR^{10}R^{11}$, $COOR^{10}$, $NO_2$, CN, $C(O)R^{10}$, $OC(O)NR^{10}R^{10}$, $C(O)NR^{10}R^{10}$, $N(R^{10})C(O)R^{10}$, $N(R^{10})(COOR^{10})$, $S(O)_n NR^{10}R^{10}$;

Each heterocyclyl is independently a 5-8 membered non-aromatic monocyclic, 8-12 membered nonaromatic bicyclic, or 11-14 membered nonaromatic tricyclic, ring system comprising 1-4 heteroatoms if monocyclic, 1-8 heteroatoms if bicyclic, or 1-10 heteroatoms if tricyclic, said heteroatoms independently selected from O, N, or S;

Each heteroaryl is independently a 5-8 membered aromatic monocyclic, 8-12 membered aromatic bicyclic, or 11-14 membered aromatic tricyclic ring system having 1-4 heteroatoms if monocyclic, 1-8 heteroatoms if bicyclic, or 1-10 heteroatoms if tricyclic, said heteroatoms independently selected from O, N, or S;

and a pharmaceutically acceptable salt thereof;
provided when $R^4$ is $OR^5$, R5 is selected from
  H;
  C1-C10 alkyl;
  C2-C10 alkenyl;
  C2-C10 alkynyl;
  C3-C10 cycloalkyl;
  C4-C10 cycloalkenyl;
  aryl;
  $R^9$;
  haloalkyl;
  C1-C10 alkyl substituted with 1-3 independent aryl, $R^7$ or $R^9$ groups;
  C3-C10 cycloalkyl substituted with 1-3 independent aryl, $R^7$ or $R^9$ groups; and
  C2-C10 alkenyl substituted with 1-3 independent aryl, $R^7$ or $R^9$.

2. The compound of claim 1, wherein:
$R^2$ is one of the formulae;

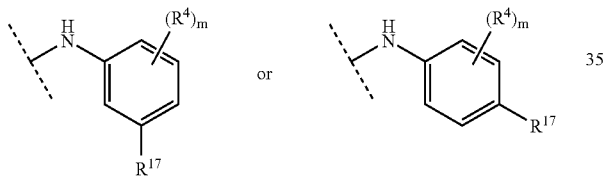

wherein $R^{17}$ is independently H; C1-C10 alkyl; C2-C10 alkenyl; C2-C10 alkynyl; C3-C10 cycloalkyl; C4-C10 cycloalkenyl; aryl; $R^8$; halo; haloalkyl; $SR^5$; $OR^{18}$; $OC(O)R^5$; $NR^5R^5$; $NR^5R^8$; $COOR^5$; $NO_2$; CN; $C(O)R^5$; $C(O)C(O)R^5$; $C(O)NR^5R^5$; $S(O)_nR^5$; $S(O)_nNR^5R^5$; $NR^5C(O)NR^5R^5$; $NR^5C(O)C(O)R^5$; $NR^5C(O)R^5$; $NR^5(COOR^5)$; $NR^5C(O)R^8$; $NR^5S(O)_nNR^5R^5$; $NR^5S(O)_nR^5$; $NR^5S(O)_nR^8$; $NR^5C(O)C(O)NR^5R^5$; $NR^5C(O)C(O)NR^5R^6$; C1-C10 alkyl substituted with 1-3 independent aryl, $R^7$ or $R^8$; or C2-C10 alkenyl substituted with 1-3 independent aryl, $R^7$ or $R^8$;

wherein $R^{18}$ is independently aryl; $R^8$; C1-C10 alkyl substituted with 1-3 independent aryl, $CF_3$, $OC(O)R^{10}$, $NHR^{19}$, $NR^{10}R^{11}$, $NR^{11}R^{11}$, $COOR^{10}$, $NO_2$, CN, $C(O)R^{10}$, $OC(O)NR^{10}R^{10}$, $C(O)NR^{10}R^{10}$, $N(R^{10})C(O)R^{10}$, $N(R^{10})(COOR^{10})$, $S(O)_nNR^{10}R^{10}$, or $R^8$; or C2-C10 alkenyl substituted with 1-3 independent aryl, $CF_3$, $OC(O)R^{10}$, $NHR^{19}$, $NR^{10}R^{11}$, $NR^{11}R^{11}$, $COOR^{10}$, $NO_2$, CN, $C(O)R^{10}$, $OC(O)NR^{10}R^{10}$, $C(O)NR^{10}R^{10}$, $N(R^{10})C(O)R^{10}$, $N(R^{10})(COOR^{10})$, $S(O)_nNR^{10}R^{10}$, or $R^8$;

wherein $R^{19}$ is independently C2-C10 alkenyl; C2-C10 alkynyl; C3-C10 cycloalkyl; C4-C10 cycloalkenyl; phenyl; or haloalkyl;

wherein m is independently 0, 1, 2 or 3;
or a pharmaceutically acceptable salt thereof.

3. The compound of claim 1, wherein:
$R^1$ is of the formula:

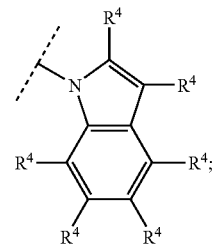

or a pharmaceutically acceptable salt thereof.

4. The compound of claim 1, wherein:
$R^1$ is independently of the formula:

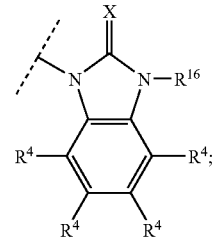

or a pharmaceutically acceptable salt thereof.

5. The compound of claim 1, wherein:
$R^1$ is of the formula:

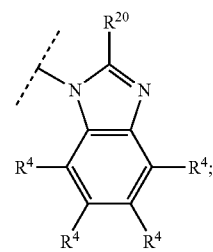

or a pharmaceutically acceptable salt thereof.

6. Compound of claim 1 selected from
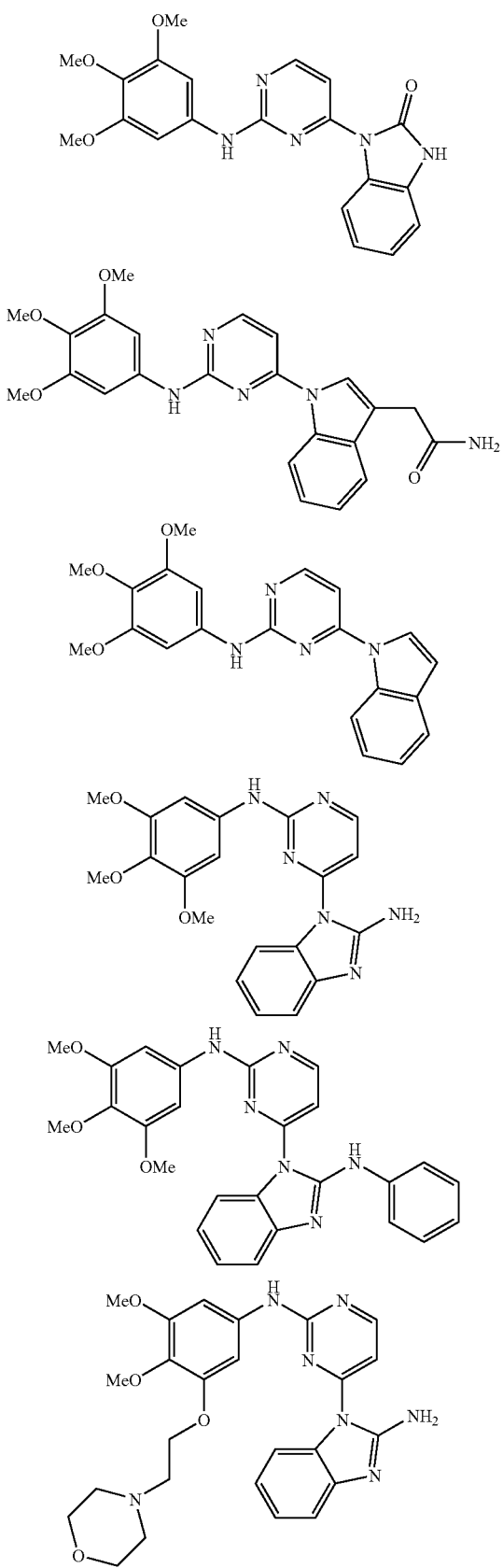
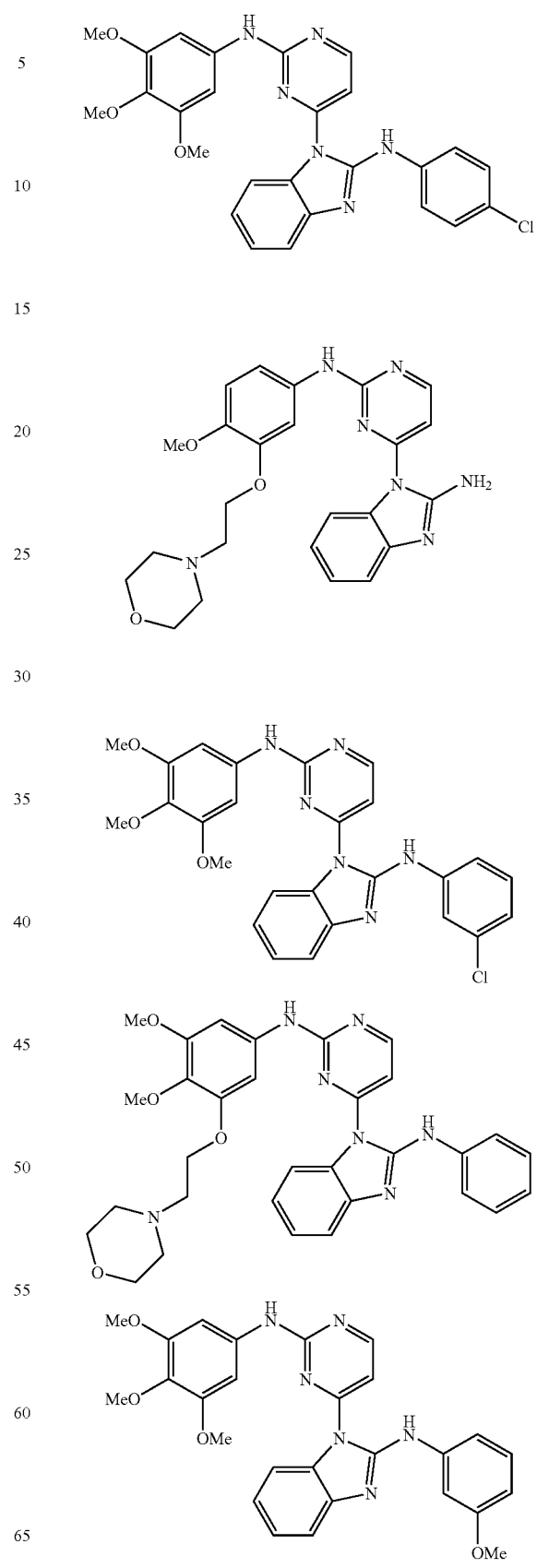

-continued
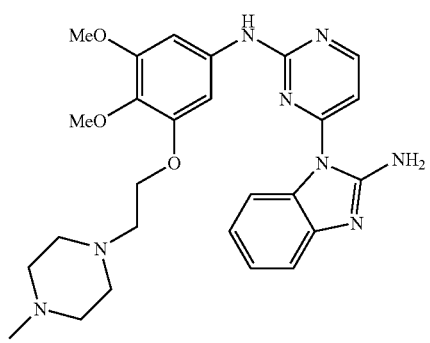
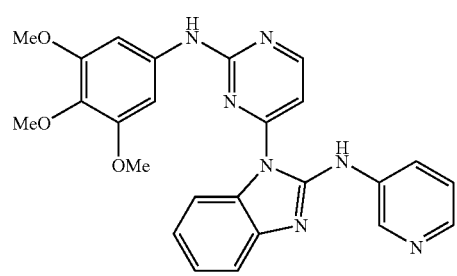
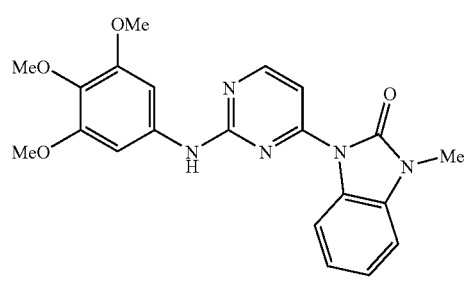
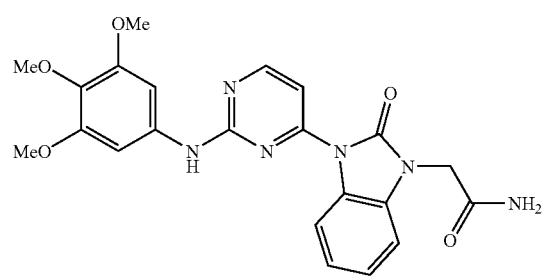
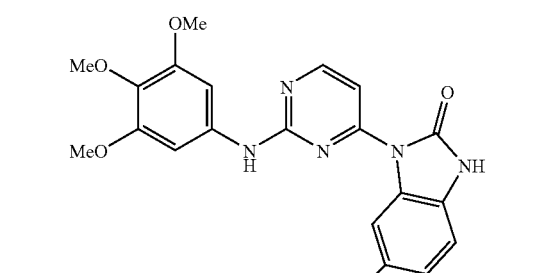
-continued
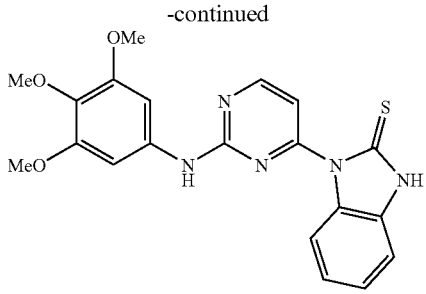
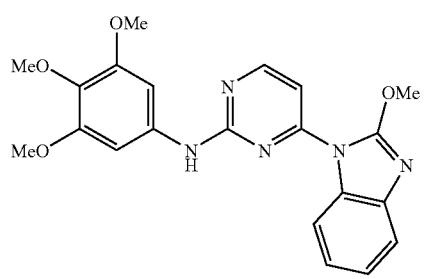
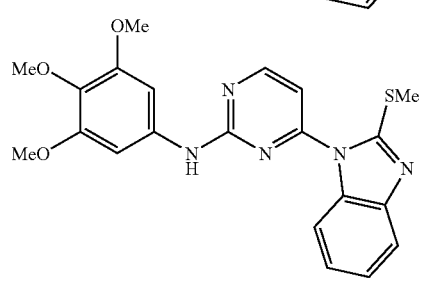
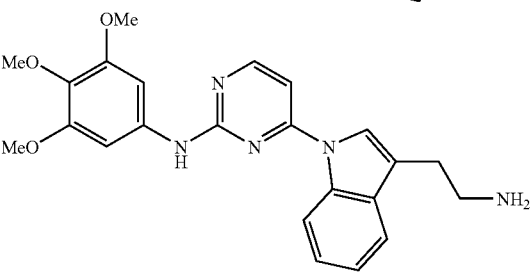
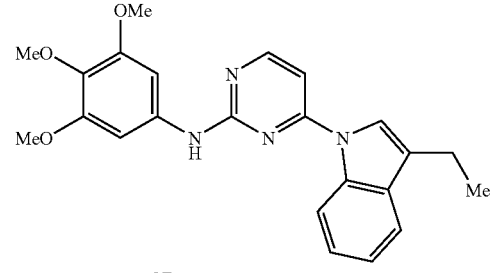
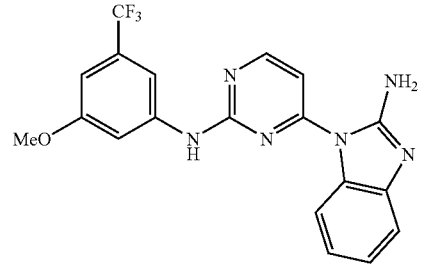

-continued

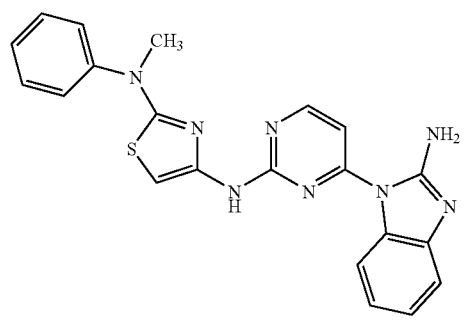

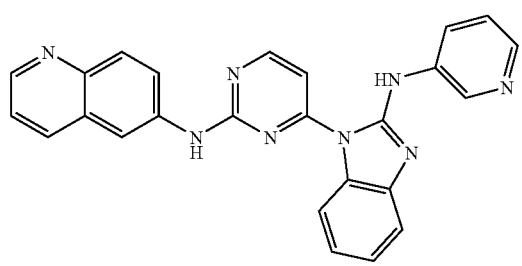

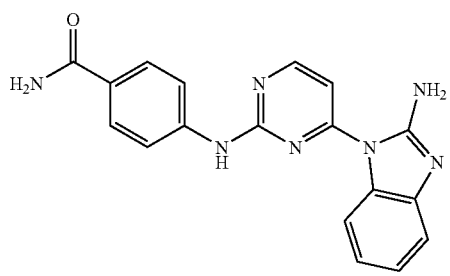

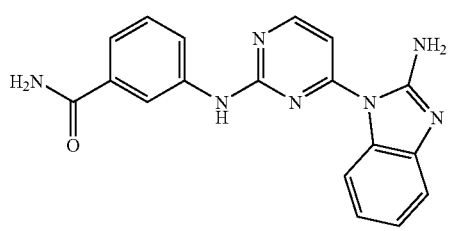

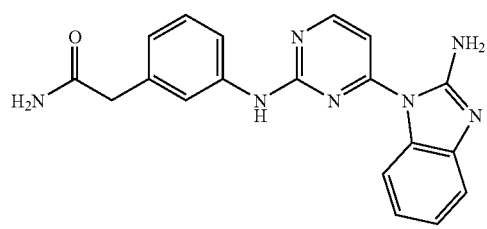

-continued

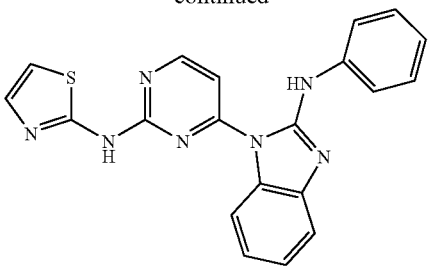

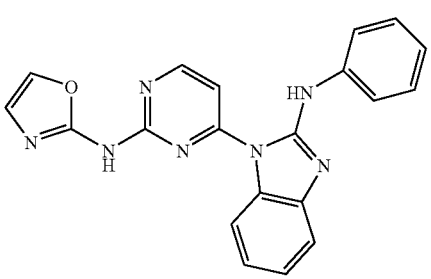

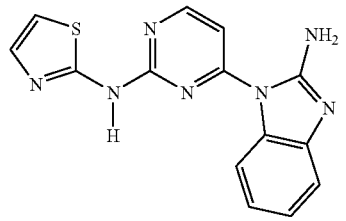

and

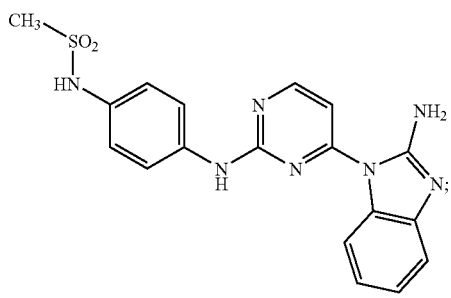

or a pharmaceutically acceptable salt thereof.

7. The compound of claim 1 wherein $R^3$ is phenyl substituted with 1-4 independent $R^4$, wherein at least one $R^4$ is not H; or a pharmaceutically acceptable salt thereof.

8. The compound of claim 1 wherein $R^3$ is heteroaryl substituted with 1-4 independent $R^4$, wherein at least one $R^4$ is not H; or a pharmaceutically acceptable salt thereof.

9. The compound of claim 2 wherein each $R^{18}$ is independently

C1-C6 alkyl substituted with 1-3 substituents independently selected from aryl, $CF_3$, $OC(O)R^{10}$, $NHR^{19}$, $NR^{10}R^{11}$, $NR^{11}R^{11}$, $COOR^{10}$, $NO_2$, CN, $C(O)R^{10}$, $OC(O)NR^{10}R^{10}$, $C(O)NR^{10}R^{10}$, $N(R^{10})C(O)R^{10}$, $N(R^{10})(COOR^{10})$, $S(O)_nNR^{10}R^{10}$, or $R^8$;

or a pharmaceutically acceptable salt thereof.

10. The compound of claim 1 of the formula
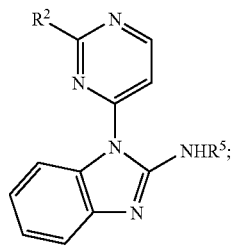
or a pharmaceutically acceptable salt thereof.
11. The compound of claim 1 of the formula
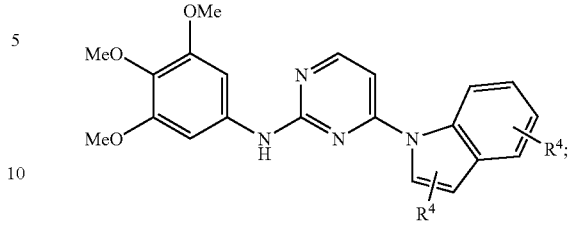
or a pharmaceutically acceptable salt thereof.
* * * * *